(12) United States Patent
Teichberg

(10) Patent No.: US 7,404,951 B2
(45) Date of Patent: Jul. 29, 2008

(54) METHOD AND COMPOSITION FOR PROTECTING NEURONAL TISSUE FROM DAMAGE INDUCED BY ELEVATED GLUTAMATE LEVELS

(75) Inventor: Vivian I. Teichberg, Savyon (IL)

(73) Assignee: Yeda Research And Development Co. Ltd., Rechovot (IL)

( * ) Notice: Subject to any disclaimer, the term of this patent is extended or adjusted under 35 U.S.C. 154(b) by 95 days.

(21) Appl. No.: 10/522,415

(22) PCT Filed: Jul. 31, 2003

(86) PCT No.: PCT/IL03/00634

§ 371 (c)(1),
(2), (4) Date: Jan. 26, 2005

(87) PCT Pub. No.: WO2004/012762

PCT Pub. Date: Feb. 12, 2004

(65) Prior Publication Data

US 2006/0024284 A1    Feb. 2, 2006

Related U.S. Application Data

(60) Provisional application No. 60/399,708, filed on Aug. 1, 2002, provisional application No. 60/430,689, filed on Dec. 4, 2002.

(51) Int. Cl.
*A61K 38/00* (2006.01)
(52) U.S. Cl. .................. 424/94.5; 435/6; 424/9.1
(58) Field of Classification Search ............. 424/94.5; 435/7.6, 16
See application file for complete search history.

(56) References Cited

FOREIGN PATENT DOCUMENTS

WO    WO 99/21565    6/1999

OTHER PUBLICATIONS

Rumigny et al, Biochemical Pharmacology, vol. 30, pp. 305-312, 1981.*
Geng et al, Journal of Neurochemistry, vol. 68, No. 6, 1997, p. 2500-06.*
BL4820 Biochemistry Techiniques□□http://www.bio.mtu.edu/campbell/bl4820/lectures/lec4/gotw41.htm, 1996.*
EC2.6.1.1 to EC2.6.1.50□□http://www.chem.qmul.ac.uk/iubmb/enzyme/EC2/0601a.html,1976.*
Haring et al, Protein Engineering, vol. 15, 2002, p. 603-610.*
Matthews et al. "Enzymatic Degradation Protects Neurons From Glutamate Excitotoxicity", Journal of Neurochemistry, 75(3): 1045-1052, 2000.
Jiang et al. "Glutamate Is A Principal Mediator of HIV-1-Infected Immune Competent Human Macrophage Neurotoxicity", Society for Neuroscience Abstracts, 26(1-2), Abstract No. 136.17, 30th Annual Meeting of the Society of Neuroscience, New Orleans, USA, 2000.
Di Giorgio et al. "Gabaergic Systems in Brain Regions of Glutamate-Lesioned Rats", Italien Journal of Biochemistry, 34(1): 19-28, 1985. p. 19, Line 15.
Engelhardt et al. "The Diagnostic Value of Enzyme Determination in Cerebrospinal Fluid", Medizinische Klinik, München, 71(17): 699-702, 1976. p. 701.
Andrae et al. "Pyruvate and Related α-Ketoacids Protect Mammalian Cells in Culture Against Hydrogen Peroxide-Induced Cytotoxicity", Toxicology Letters, 28: 93-98, 1985.
Avramis et al. "A Randomized Comparison of Native *Escherichia coli* Asparaginase and Polyethelyne Glycol Conjugated Asparaginase for Treatment of Children With Newly Diagnosed Standard-Risk Acute Lymphoblastic Leukemia: A Children's Cancer Group Study", Blood, 99(6): 1986-1994, 2002.
Cavallini et al. "The Protective Action of Pyruvate on Recovery of Ischemic Rat Heart: Comparison With Other Oxidizable Substrates", Journal of Molecular Cell Cardiology, 22: 143-154, 1990.
Desagher et al. "Pyruvate Protects Neurons Against Hydrogen Peroxide-Induced Toxicity", The Journal of Neuroscience, 17(23): 9060-9067, 1997.
Gramsbergen et al. "Pyruvate Protects Against 3-Nitropropionic Acid Neurotoxicity in Corticostriatal Slice Cultures", Neuropharmacology, 11(21): 2743-2747, 2000.
Hosoya et al. "Blood-Brain Barrier Produces Significant Efflux of L-Aspartic Acid But Not D-Aspartic Acid: In Vivo Evidence Using the Brain Efflux Index Method", Journal of Neurochemistry, 73: 1206-1211, 1999.
Lee et al. "Protection by Pyruvate Against Transient Forebrain Ischemia in Rats", The Journal of Neuroscience, 21(RC171): 1-6, 2001.
Liu et al. "P-Glycoprotein Regulated Transport of Glutamate at Blood-Brain Barrier", Acta Pharmacol Sin, 22(2): 111-116, 2001.
Matsumoto et al. "Role of Pyruvate in Ischemia-Like Conditions on Cultured Neurons", Neurological Research, 16: 460-464, 1994.
Matthews et al. "Glutamate-Pyruvate Transaminase Protects Against Glutamate Toxicity in Hippocampal Slices", Brain Research, 978: 59-64, 2003.
Matthews et al. "Enzymatic Degradation Protects Neurons From Glutamate Excitotoxicity", Journal of Neurochemistry, 75: 1045-1052, 2000.
Maus et al. "Pyruvate and Lactate Protect Striatal Neurons Against N-Methyl-D-Aspartate-Induced Neurotoxicity", European Journal of Neuroscience, 11: 3215-3224, 1999.
Mongan et al. "Pyruvate Improves Cerebral Metabolism During Hemorrhagic Shock", AJP—Heart and Circulatory Physiology, 281: 854-864, 2001.
Mongan et al. "Intravenous Pyruvate Prolongs Survival During Hemorrhagic Shock in Swine", AJP—Heart and Circulatory Physiology, 277(46): H2253-H2263, 1999.

(Continued)

*Primary Examiner*—Ruth A. Davis
*Assistant Examiner*—Tiffany M Gough

(57) ABSTRACT

A method of reducing extracellular brain glutamate levels. The method comprises administering to a subject in need thereof a therapeutically effective amount of an agent capable of reducing blood glutamate levels thereby reducing extracellular brain glutamate levels.

17 Claims, 22 Drawing Sheets

OTHER PUBLICATIONS

O'Kane et al. "Na+-Independent Glutamate Transporters (EAAT1, EAAT2, and EAAT3) of the Blood-Brain Barrier", The Journal of Biological Chemistry, 274(45): 31891-31895, 1999.

Ruiz et al. "Protection by Pyruvate and Malate Against Glutamate-Mediated Neurotoxicity", NeuroReport, 9: 1277-1282, 1998.

Ryu et al. "Neuroprotective Effects of Pyruvate in the Quinolinic Acid Rat Model of Huntington's Disease", Experimental Neurology, 183: 700-704, 2003.

Steele "Blood-Brain Barrier Transport of the α-Keto Acid Analogs of Amino Acids", Federation Proceedings, 45(7): 2060-2064, 1986.

Stover et al. "Neurotransmitters in Cerebrospinal Fluid Reflect Pathological Activity", European Journal of Clinical Investigation, 27: 1038-1043, 1997.

Wolff et al. "The Effectiveness of Benzoate in the Management of Seizures in Nonketotic Hyperglycinemia", AJDC, 140: 596-602, 1986.

* cited by examiner

METHOD AND COMPOSITION FOR PROTECTING NEURONAL TISSUE FROM DAMAGE INDUCED BY ELEVATED GLUTAMATE LEVELS

RELATED PATENT APPLICATION

This application is a National Phase Application of PCT/IL03/00634 having International Filing Date of 31 Jul. 2003, which claims priority from U.S. Provisional Patent Application No. 60/399,708 filed 1 Aug. 2002, and U.S. Provisional Patent Application No. 60/430,689 filed 4 Dec. 2002.

FIELD AND BACKGROUND OF THE INVENTION

The present invention relates to a method and composition for protecting the central nervous system (CNS) from damage induced by abnormal levels of glutamate, which may result from, for example, a stroke.

The central nervous system is composed of trillions of nerve cells (neurons) that form networks capable of performing exceedingly complex functions.

The amino acid L-glutamic acid (Glutamate), mediates many of the excitatory transactions between neurons in the central nervous system. Under normal conditions, accumulation of glutamate in the extracellular space is prevented by the operation of a recycling mechanism that serves to maintain neuronal glutamate levels despite continual loss through transmitter release (Van der Berg and Garfinkel, 1971; Kennedy et al., 1974). Glutamate, released by glutamatergic neurons, is taken up into glial cells where it is converted into glutamine by the enzyme glutamine synthetase. Glutamine reenters the neurons and is hydrolyzed by glutaminase to form glutamate, thus replenishing the neurotransmitter pool.

This biochemical pathway also serves as an endogenous neuroprotective mechanism, which functions by removing the synaptically released glutamate from the extracellular space and converting it to the nontoxic amino acid glutamine before toxicity occurs. The excitotoxic potential of glutamate (i.e., defined as the ability of excess glutamate to overexcite neurons and cause their death) is held in check as long as the transport process is functioning properly. However, failure or reduction in the transport process such as under ischemic conditions, results in accumulation of glutamate in the extracellular synaptic fluid and excessive stimulation of excitatory receptors, a situation that leads to neuronal death.

Two additional factors complicate and make matters worse: (i) overstimulated neurons begin to release excessive quantities of glutamate at additional synaptic junctions; this causes even more neurons to become overstimulated, drawing them into a neurotoxic cascade that reaches beyond the initial zone of ischemia; and, (ii) overstimulated neurons begin utilizing any available supplies of glucose or oxygen even faster than normal, which leads to accelerated depletion of these limited energy resources and further impairment of the glutamate transport process. This biochemical cascade of induction and progression may continue for hours or days and causes delayed neuronal death.

Abnormally high glutamate (Glutamate) levels in brain interstitial and cerebrospinal fluids are the hallmark of several neurodegenerative conditions. These include acute brain anoxia/ischemia i.e stroke (Graham et al., 1993; Castillo et al., 1996), perinatal brain damage (Hagberg et al., 1993; Johnston, 1997), traumatic brain injury (Baker et al., 1993; Zauner et al., 1996), bacterial meningitis (Spranger et al, 1996), subarachnoid hemorrhage, open heart and aneurysm surgery (Persson et al., 1996; Saveland et al., 1996), hemorrhagic shock (Mongan et al. 1999, 2001), newly diagnosed epilepsy (Kalviainen et al., 1993), acute liver failure (Rose et al. 2000), migraine [Martinez F, Castillo J, Rodriguez J R, Leira R, Noya M, Cephalalgia. 1993 April; 13(2):89-93], stress [Abraham I, Juhasz G, Kekesi K A, Kovacs K J, Stress. 1998 July; 2(3):171-81 and De Cristobal J, Madrigal J L, Lizasoain I, Lorenzo P, Leza J C, Moro M A, Neuroreport. 2002 Feb. 11; 13(2):217-21] and various chronic neurodegenerative diseases such as glaucoma (Dreyer et al., 1996), amyotrophic lateral sclerosis (Rothstein et al., 1990; Shaw et al., 1995), HIV dementia (Ferrarese et al. 2001) and Alzheimer's disease (Pomara et al., 1992).

Thus, one object of medical therapy is to break or eliminate the above described cascade process and thus prevent glutamate associated neuronal damage.

Since glutamate excitotoxicity is mediated by the glutamate receptors, a potential therapeutic approach has been to develop and apply various selective glutamate receptor antagonists in animal models of neurodegeneration. Though displaying powerful neuroprotective effects in experimental stroke and head trauma, the glutamate receptor antagonists failed in clinical trials mainly because of their adverse or even lethal effects (Birmingham, 2002; Lutsep and Clark, 2001; Palmer, 2001).

Attempts have also been made to increase the activity of the various glutamate transporters, present on glia and neurons, which take up Glutamate from the brain interstitial fluid and thereby limit glutamate excitatory action and excitotoxicity. However, none of the above-described approaches have been successful in providing a viable therapeutic approach for lowering glutamate levels.

In light of these failures and the need of alternative approaches to the treatment of neurodegenerative disorders involving glutamate excitotoxicity, the present inventor has hypothesized that excess glutamate in brain interstitial (ISF) and cerebrospinal (CSF) fluids could be eliminated by increasing the relatively poorly studied brain-to-blood glutamate efflux mechanism. Increasing the efflux can be achieved by lowering the glutamate levels in blood thereby increasing glutamate transport from brain ISF/CSF to blood.

While reducing the present invention to practice, the present inventor has uncovered that by maximally activating two enzymes, glutamate-pyruvate transaminase (GPT) and glutamate-oxaloacetate transaminase (GOT), glutamate degradation in the blood is increased. These two enzymes are two examples of a wider group of enzymes that use glutamate as a substrate in the general formula:

A +GLUTAMATE ←(enzyme)→ C+D whereby A represents the co-substrate, ←(enzyme)→ symbolizes a reversible enzyme and C and D are metabolites of the enzyme. Examples illustrated by this formula include: Glutamate+oxaloacetate ←(GOT)→ 2-keto-glutarate+aspartate, Glutamate+pyruvate ←(GPT)→ 2-keto-glutarate+alanine or Glutamate+4-methyl-2-oxopentoate ←(branched-chain-amino-acid transaminase)→2-ketoglutarate+Valine.

Examples for different substrates that work on the same enzyme include: Glutamate+2-oxohexanedioic acid ←(GOT)→ 2-keto-glutarate+2-aminohexanedioic acid. Glutamate+2-oxo-3-phenylpropionic acid ←(GOT)→2-keto-glutarate+phenylalanine. Glutamate+3-hydroxy-2-oxopropionic acid ←(GOT)→2-keto-glutarate+serine. Glutamate+5-oxopentanoate ←(GPT)→2-keto-glutarate+5-aminopentanoate. Glutamate+4-oxobutanoate ←(GPT)→2-keto-glutarate+4-aminobutanoate. Glutamate+glyoxalate ←(GPT)→2-keto-glutarate+glycine.

Another common feature that these enzymes share is that they use pyridoxal phosphate as a cofactor.

As stated, these enzymes reversibly convert glutamate into 2-keto glutarate. This causes blood glutamate levels to decrease below basal levels thereby creating a far steeper gradient of glutamate levels between the brain ISF/CSF and blood, than normally exists. In order to reach a novel equilibrium, glutamate is transported from the brain to the blood thus lowering the elevated levels of glutamate in the brain. As long as the glutamate levels are low in the blood, this brain-to-blood efflux will continue. In order to keep GOT and GPT working at their maximum levels for the conversion of glutamate into 2-ketoglutarate ($V_{max}$) their respective substrates, oxaloacetate and pyruvate have to be administered at doses at least twice their Km values.

As stated above both glutamate-oxaloacetate transaminase and glutamate-pyruvate transaminase metabolize glutamate, while using oxaloacetate and pyruvate as their respective co-substrates. There are however many other transaminases in the body that can metabolize glutamate such as glutamate, branched-chain-amino-acid transaminase, GABA aminotransferases and many others. For each enzyme according to its reaction, a specific substrate such as succinate semialdehyde for 4-aminobutyrate transaminase should be used.

Conversely, although pyruvate and oxaloacetate are possibly the best substrates for the glutamate transaminases, other substrates such as 2-oxohexanedioic acid, 2-oxo-3-sulfopropionate, 2-oxo-3-sulfinopropionic acid, 2-oxo-3-phenylpropionic acid or 3-indole-2-oxopropionic acid instead of oxaloacetate and 5-oxopentanoate, 6-oxo-hexanoate or glyoxalate instead of pyruvate can be used.

The conversion of glutamate to 2-ketoglutarate is reversible. Thus, upon glutamate transformation via an enzymatic reaction into 2-ketoglutarate, there is a buildup of 2-ketoglutarate which can cause the enzyme to work in the reverse direction and convert 2-ketoglutarate into glutamate. It is therefore beneficial to further break down 2-ketoglutarate and in this way insure the continual metabolism of glutamate. One such enzyme that metabolizes 2-ketoglutarate is 2-ketoglutarate dehydrogenase through the general reaction—2-ketoglutarate+lipoamide←(2-ketoglutarate dehydrogenase)→ S-succinyldihydrolipoamide+$CO_2$.

Thus, the present inventor provides a novel approach for protecting neural tissue from damage induced by elevated glutamate levels.

SUMMARY OF THE INVENTION

According to one aspect of the present invention there is provided a method of reducing extracellular brain glutamate levels, the method comprising administering to a subject in need thereof a therapeutically effective amount of an agent capable of reducing blood glutamate levels thereby reducing extracellular brain glutamate levels.

According to another aspect of the present invention there is provided a pharmaceutical composition for reducing extracellular brain glutamate levels, the pharmaceutical composition comprising, as an active ingredient, an agent capable of reducing blood glutamate levels and a pharmaceutically acceptable carrier.

According to yet another aspect of the present invention there is provided a pharmaceutical composition for reducing extracellular brain glutamate levels, the pharmaceutical composition comprising, as an active ingredient, pyruvate and oxaloacetate in a concentration suitable for reducing blood glutamate levels and a pharmaceutically acceptable carrier.

According to still another aspect of the present invention there is provided an article-of-manufacture comprising packaging material and a pharmaceutical composition identified for reducing extracellular brain glutamate levels being contained within the packaging material, the pharmaceutical composition including, as an active ingredient, an agent capable of reducing blood glutamate levels and a pharmaceutically acceptable carrier.

According to an additional aspect of the present invention there is provided a method of reducing extracellular brain glutamate levels in a subject in need thereof, the method comprising: (a) obtaining a blood sample; (b) contacting the blood sample with an agent capable of reducing glutamate levels of cells present in the blood sample to thereby obtain glutamate depleted blood cells; and (c) introducing the glutamate depleted blood cells into the subject, thereby reducing extracellular brain glutamate levels thereof.

According to yet an additional aspect of the present invention there is provided a pharmaceutical composition for reducing extracellular brain glutamate levels, the pharmaceutical composition comprising, as an active ingredient, oxaloacetate diethylester capable of reducing blood glutamate levels and a pharmaceutically acceptable carrier Alternative active ingredients of the pharmaceutical composition include, but are not limited to, oxaloacetate, pyruvate, $NAD^+$, $NADP^+$, 2-oxohexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxo-hexanoate, glyoxalate, 4-oxobutanoate, α-ketoisocaproate, α-ketoisovalerate, α-keto-β-methylvalerate, succinic semialdehyde-(-4-oxobutyrate), pyridoxal phosphate, pyridoxal phosphate precursors and 3-oxoisobutanoate.

According to further features in preferred embodiments of the invention described below, the agent is at least one glutamate modifying enzyme and/or a modification thereof (e.g. an ester thereof).

According to still further features in the described preferred embodiments the at least one glutamate modifying enzyme is selected from the group consisting of a transaminase, a dehydrogenase, a decarboxylase, a ligase, an aminomutase, a racemase and a transferase.

According to still further features in the described preferred embodiments the transaminase is selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, (s)-3-amino-2-methylpropionate transaminase, 4-hydroxyglutamate transaminase, diiodotyrosine transaminase, thyroid-hormone transaminase, tryptophan transaminase, diamine transaminase, cysteine transaminase, L-Lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, and udp-2-acetamido-4-amino-2,4,6-trideoxyglucose transaminase.

According to still further features in the described preferred embodiments the dehydrogenase is a glutamate dehydrogenase.

According to still further features in the described preferred embodiments the decarboxylase is a glutamate decarboxylase.

According to still further features in the described preferred embodiments the ligase is a glutamate-ethylamine ligase.

According to still further features in the described preferred embodiments the transferase is selected from the group consisting of glutamate N-acetyltransferase and adenylyltransferase.

According to still further features in the described preferred embodiments the aminomutase is a glutamate-1-semialdehyde 2,1-aminomutase.

According to still further features in the described preferred embodiments the agent is at least one co-factor of a glutamate modifying enzyme.

According to still further features in the described preferred embodiments the co-factor is selected from the group consisting of oxaloacetate, pyruvate, $NAD^+$, $NADP^+$, 2-oxo-hexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxo-hexanoate, glyoxalate, 4-oxobutanoate, α-ketoisocaproate, α-ketoisovalerate, α-keto-β-methylvalerate, succinic semialdehyde-(−4-oxobutyrate), pyridoxal phosphate, pyridoxal phosphate precursors and 3-oxoisobutanoate.

According to still further features in the described preferred embodiments the agent is a modified glutamate converting enzyme being selected incapable of converting the modified glutamate into glutamate and/or a modification thereof.

According to still further features in the described preferred embodiments the modified glutamate converting enzyme is a modified glutarriate oxaloacetate transaminase (GOT).

Such a modified enzyme can be obtained via in vitro evolution of, for example, a human GOT sequence. For example, chemical or molecular mutagenesis can be used to generate mutated GOT sequences which exhibit enhanced activity in transforming glutamate into α-ketoglutarate and preferably little or no reverse activity [strategies for in vitro enzyme evolution is described by, for example, Moore et al., in J Mol. Biol. 1997 Sep. 26; 272(3):336-47, additional references are provided hereinbelow].

According to still further features in the described preferred embodiments the agent is a co-factor of a modified glutamate converting enzyme being selected incapable of converting the modified glutamate into glutamate.

According to still further features in the described preferred embodiments the agent is selected from the group consisting of lipoic acid, lipoic acid precursor, pyridoxal phosphate, pyridoxal phosphate precursor, thiamine pyrophosphate and thiamine pyrophosphate precursor.

According to still further features in the described preferred embodiments the agent includes a glutamate modifying enzyme and a co-factor thereof.

According to still further features in the described preferred embodiments the agent includes a glutamate modifying enzyme and a modified glutamate converting enzyme being selected incapable of converting the modified glutamate into glutamate.

According to still further features in the described preferred embodiments the agent includes a co-factor of a glutamate modifying enzyme and a modified glutamate converting enzyme being selected incapable of converting the modified glutamate into glutamate.

According to still further features in the described preferred embodiments the agent includes a co-factor of a glutamate modifying enzyme, a modified glutamate converting enzyme being selected incapable of converting the modified glutamate into glutamate and a co-factor thereof.

According to still further features in the described preferred embodiments the agent includes a glutamate modifying enzyme, a co-factor thereof, a modified glutamate converting enzyme being selected incapable of converting the modified glutamate into glutamate and a co-factor thereof.

According to still further features in the described preferred embodiments the agent includes a glutamate modifying enzyme, a co-factor thereof, and a modified glutamate converting enzyme being selected incapable of converting the modified glutamate into glutamate.

According to still further features in the described preferred embodiments the agent includes a glutamate modifying enzyme, a modified glutamate converting enzyme being selected incapable of converting the modified glutamate into glutamate and a co-factor thereof.

According to still further features in the described preferred embodiments the agent includes a glutamate modifying enzyme and a co-factor of a modified glutamate converting enzyme being selected incapable of converting the modified glutamate into glutamate.

According to still further features in the described preferred embodiments the agent includes a modified glutamate converting enzyme being selected incapable of converting the modified glutamate into glutamate and a co-factor thereof.

According to still further features in the described preferred embodiments the agent includes a co-factor of a glutamate modifying enzyme and a co-factor of a modified glutamate converting enzyme being selected incapable of converting the modified glutamate into glutamate.

According to still further features in the described preferred embodiments the administering is effected at a concentration of the agent not exceeding 1 g/Kg body weight/hour.

According to still further features in the described preferred embodiments the agent is at least one inhibitor of a glutamate synthesizing enzyme.

According to still further features in the described preferred embodiments wherein the inhibitor is selected from the group consisting of gamma-Acetylenic GABA, GABAculine, L-canaline, 2-amino-4-(aminooxy)-n-butanoic acid, 3-Chloro-4-aminobutanoate, 3-Phenyl-4-aminobutanoate, Isonicotinic hydrazide;(S)-3-Amino-2-methylpropanoate, Phenylhydrazine; 4-Fluorophenyl)alanine, Adipate, Azaleic acid, Caproate, 3-Methylglutarate, Dimethylglutarate, Diethylglutarate, Pimelate, 2-Oxoglutamate, 3-Methyl-2-benzothiazolone hydrazone hydrochloride, Phenylpyruvate, 4-hydroxyphanylpyruvate, Prephenate and Indole pyruvate.

The present invention successfully addresses the shortcomings of the presently known configurations by providing methods and compositions for protecting neuronal tissue from damage induced by elevated glutamate levels Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
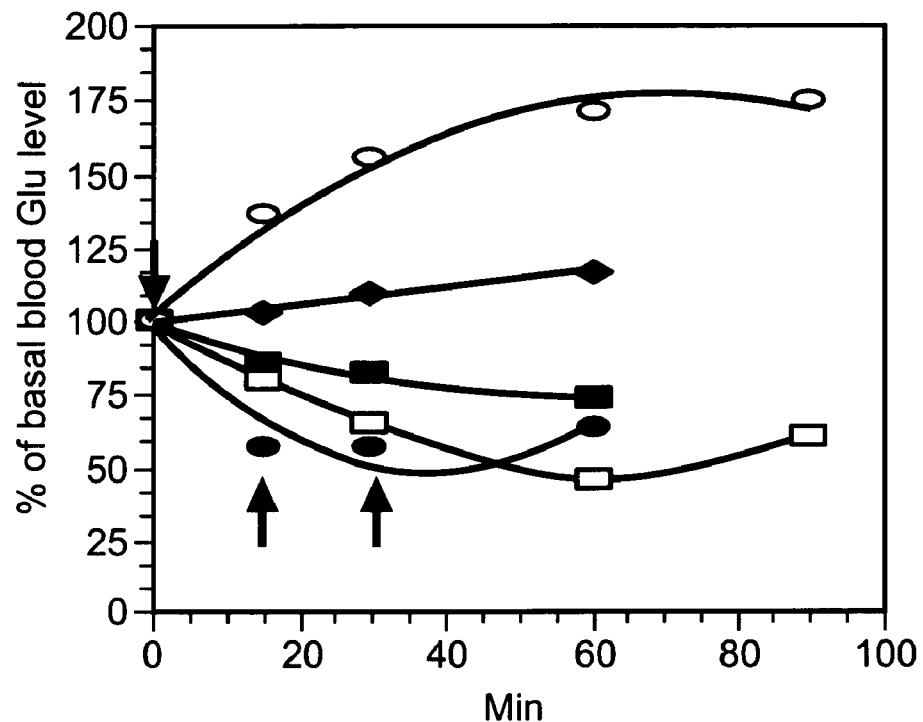
FIG. 1A is a graphic representation of glutamate levels over time as a function of different in-vitro incubation conditions. Untreated controls (filled diamonds) reveal fairly constant glutamate levels. The black downward arrow indicates the beginning of treatment with 2.5 units/ml of GPT, resulting in a precipitous increase in glutamate levels (white circles). The addition of 1 mM of pyruvate (indicated by black arrows) results in the reverse effect, a decline in glutamate concentration (filled squares). Addition of 1 mM of pyruvate and 2.5 units/ml of GPT (filled circles) at t=0 results in a greater decline than when administering pyruvate alone. The addition of 1 mM of pyruvate at t=0 and of 2.5 units/ml of GPT at t=0, 15 and 30 (white squares) and similarly results in a marked decline in glutamate concentration, exceeding that of either supplied individually. All incubations were done at 37° C. and each point represents the average of at least two Glutamate determinations.

The present invention is of compositions and methods using same for reducing the levels of extracellular glutamate in the brain of a subject. Specifically, the present invention can be used to treat acute and chronic brain diseases in which elevated levels of glutamate are detrimental to the subject, such as in ischemic conditions.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Abnormally high glutamate levels in brain interstitial and cerebrospinal fluids are the hallmark of several neurodegenerative conditions. Numerous approaches to reduce glutamate excitotoxicity include development of glutamate receptor antagonists, and up-regulation of glutamate transporters. While the first are limited by adverse and even lethal effects probably due to poor selectivity, none of the latter have been successful in providing a viable therapeutic approach for lowering glutamate levels.

While reducing the present invention to practice and while searching for a novel therapeutic modality to clinical conditions associated with elevated extracellular brain glutamate levels, the present inventor has uncovered that excess extracellular brain glutamate can be eliminated by increasing the brain to blood glutamate efflux.

These findings enable to generate highly efficient therapeutic compositions which can be utilized to treat clinical conditions characterized by elevated extracellular brain glutamate levels.

Thus, according to one aspect of the present invention, there is provided a method of reducing extracellular brain glutamate levels.

The method is effected by administering to a subject in need thereof, a therapeutically effective amount of an agent capable of reducing blood glutamate levels, thereby increasing brain to blood glutamate efflux and consequently reducing extracellular brain glutamate levels.

Preferred individual subjects according to the present invention are mammals such as canines, felines, ovines, porcines, equines, bovines, humans and the like.

An agent, which is capable of reducing blood glutamate according to this aspect of the present invention includes any glutamate modifying enzyme and/or a co-factor thereof or any artificially modified derivatives (e.g. esters).

As used herein "a glutamate modifying enzyme" is an enzyme, which utilizes glutamate as a substrate and produces a glutamate reaction product. A glutamate modifying enzyme can be a natural occurring enzyme or an enzyme which has been modified to obtain improved features, such as higher affinity to glutamate than to a modified glutamate, stability under physiological conditions, solubility, enhanced enantioselectivity, increased thermostability and the like as is further described hereinunder.

Numerous glutamate modifying enzymes are known in the art. For example, transaminases, which play a central role in amino acid metabolism and generally funnel α-amino groups from a variety of amino acids via the coupled conversion of glutamate into α-ketoglutarate or of α-ketoglutarate into glutamate.

Examples of transaminases include but are not limited to glutamate oxaloacetate transaminases, glutamate pyruvate transaminases, acetylornithine transaminases, ornithine-oxo-acid transaminases, succinyldiaminopimelate transaminases, 4-aminobutyrate transaminases, alanine transaminases (note: same as glutamate pyruvate transaminases, (s)-3-amino-2-methylpropionate transaminases, 4-hydroxyglutamate transaminases, diiodotyrosine transaminases, thyroid-hormone transaminases, tryptophan transaminases, diamine transaminases, cysteine transaminases, L-Lysine 6-transaminases, histidine transaminases, 2-aminoadipate transaminases, glycine transaminases, branched-chain-amino-acid transaminases, 5-aminovalerate transaminases, dihydroxyphenylalanine transaminases, tyrosine transaminases, phosphoserine transaminases, taurine transaminases, aromatic-amino-acid transaminases, aromatic-amino-acid-glyoxylate transaminases, leucine transaminases, 2-aminohexanoate transaminases, ornithine (lysine) transaminases, kynurenine-oxoglutarate transaminases, D-4-hydroxyphenylglycine transaminases, cysteine-conjugate transaminases, 2,5-diaminovalerate transaminases, histidinol-phosphate transaminases, diaminobutyrate-2-oxoglutarate transaminases, UDP-2-acetamido-4-amino-2,4,6-trideoxyglucose transaminases and aspartate transaminases (please note: same as glutamate oxaloacetate transaminases).

Other examples of glutamate modifying enzymes include but are not limited to glutamate dehydrogenases, which generate ammonium ion from glutamate by oxidative deamination; decarboxylases such as glutamate decarboxylase; ligases such as glutamate-ethylamine ligase, glutamate-cysteine ligase; transferases such as glutamate N-acetyltransferase and N2-acetyl-L-ornithine, adenylyltransferase; aminomutases such as glutamate-1-semialdehyde 2,1-aminomutase and glutamate racemase [Glavas and Tanner (2001) Biochemistry 40(21):6199-204)].

It will be appreciated that artificially modified enzymes can also be used according to this aspect of the present invention.

Modification of enzymes can be effected using numerous protein directed evolution technologies known in the art [for review see Kuchner and Arnold (1997) TIBTECH 15:523-530].

Typically, directed enzyme evolution begins with the creation of a library of mutated genes. Gene products that show improvement with respect to the desired property or set of properties are identified by selection or screening, and the gene(s) encoding those enzymes are subjected to further cycles of mutation and screening in-order to accumulate beneficial mutations. This evolution can involve few or many generations, depending on the progress observed in each generation.

Preferably, for successful directed evolution a number of requirements are met; the functional expression of the enzyme in a suitable microbial host; the availability of a screen (or selection) sensitive to the desired properties; and the identification of a workable evolution strategy.

Examples of mutagenesis methods which can be used in enzyme directed evolution according to this aspect of the present invention include but are not limited to UV irradiation, chemical mutagenesis, poisoned nucleotides, mutator strains [Liao (1986) Proc. Natl. Acad. Sci. U.S.A 83:576-80], error prone PCR [Chen (1993) Proc. Natl. Acad. Sci. U.S.A 90:5618-5622], DNA shuffling [Stemmer (1994) Nature 370: 389-91], cassette [Strausberg (1995) Biotechnology 13:669-73], and a combination thereof [Moore (1996) Nat. Biotechnol. 14:458-467; Moore (1997) J. Mol. Biol. 272:336-347].

Screening and selection methods are well known in the art [for review see Zhao and Arnold (1997) Curr. Opin. Struct. Biol. 7:480-485; Hilvert and Kast (1997) Curr. Opin. Struct. Biol. 7:470-479]. Typically, selections are attractive for searching larger libraries of variants, but are difficult to device for enzymes that are not critical to the survival of the host organism. Further more, organisms may evade imposed selective pressure by unexpected mechanisms. Less stringent functional complementation can be useful in identifying variants which retain biological activity in libraries generated using relatively high mutagenic rates [Suzuki (1996) Mol. Diversity 2:111-118; Shafikhani (1997) Biol. Techniques 23:304-310; Zhao and Arnold (1997) Curr. Opin. Struct. Biol. 7:480-485].

As described hereinabove, the agent according to this aspect of the present invention, can include one or more co-factors of glutamate modifying enzymes, which can accelerate activity of the latter ($V_{max}$). These can be administered in order to enhance the rate of endogenous glutamate modifying enzymes or in conjunction with glutamate modifying enzymes (described hereinabove).

Co-factors of glutamate-modifying enzymes include but are not limited to oxaloacetate, pyruvate, NAD+, NADP+, 2-oxohexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxo-hexanoate, glyoxalate, 4-oxobutanoate, α-ketoisocaproate, α-ketoisovalerate, α-keto-β-methylvalerate, succinic semialdehyde-(–4-oxobutyrate), 3-oxoisobutanoate, pyridoxal phosphate, 5-oxopentanoate, 6-oxohexanoate and their artificially modified derivatives (e.g., esters).

Since modified glutamate (i.e., glutamate reaction product) can be reversibly modified (i.e., interconverted) to glutamate, the agent, according to this aspect of the present invention, preferably includes a modified glutamate converting enzyme which is incapable of converting the modified glutamate back into glutamate to thereby insuring continual metabolism of glutamate.

Examples of modified or modifiable glutamate converting enzymes include but are not limited to GPT and GOT, and the like.

Modified glutamate converting enzymes can also include glutamate modifying enzymes artificially modified to possess lower affinity for glutamate reaction product than for glutamate. For example, the E. coli GOT (GenBank Accession No. D90731.1) is characterized by an affinity for glutamate of about 8 mM and an affinity for 2-ketoglutarate of about 0.2 mM. A human enzyme or a humanized enzyme characterized by such affinities is preferably used according to this aspect of the present invention such as described by Doyle et al. in Biochem J. 1990 270(3):651-7.

Optionally, co-factors of modified glutamate converting enzymes can be included in the agent according to this aspect of the present invention. Examples of co-factors of modified glutamate converting enzymes include but are not limited to lipoic acid and its precursors, thiamine pyrophosphate and its precursors, pyridoxal phosphate and its precursors and the like.

It will be appreciated that the agent according to this aspect of the present invention may also include inhibitors of glutamate synthesizing enzymes (e.g., phosphate activated glutaminase). Numerous inhibitors of glutamate producing enzymes are known in the art. Examples include but are not limited gabapentin which has been shown to modulate the activity of branched chain aminotransferases [Taylor (1997) Rev. Neurol. 153(1):S39-45] and aspirin at high doses (i.e., 4-6 g/day) a neuroprotective drug against glutamate excitotoxicity [Gomes (1998) Med. J. India 11:14-17]. Other inhibitors may be identified in the publicly available BRENDA, a comprehensive enzyme information system [www-.brenda.uni-koeln.de/]. Examples include but are not limited to, gamma-Acetylenic GABA, GABAculine, L-canaline, 2-amino-4-(aminooxy)-n-butanoic acid; 3-Chloro-4-aminobutanoate; 3-Phenyl-4-aminobutanoate; Isonicotinic hydrazide;(S)-3-Amino-2-methylpropanoate; Phenylhydrazine; 4-Fluorophenyl)alanine; Adipate, Azelaic acid, Caproate, 3-Methylglutarate, Dimethylglutarate, Diethylglutarate, Pimelate, 2-Oxoglutamate; 3-Methyl-2-benzothiazolone hydrazone hydrochloride; Phenylpyruvate, 4-Hydroxyphenylpyruvate, Prephenate, Indole pyruvate and their artificially modified derivatives (e.g., esters). Although each of the components described hereinabove may comprise the agent of the present invention, it will be appreciated that for optimal blood-glutamate reducing activity, the agent may include a combination of the above described components (i.e., glutamate modified enzyme, co-factor thereof, modified glutamate converting enzyme and co-factor thereof).

As further illustrated in the Examples section which follows, for optimal brain-to-blood glutamate efflux the agent is preferably selected capable of reducing plasma glutamate levels rather than blood cell glutamate levels.

Thus, according to preferred embodiments of this aspect of the present invention the agent includes oxaloacetate and pyruvate. Preferably, the agent is administered at a dose not exceeding 1 g/kg×hour.

Figure 27A:
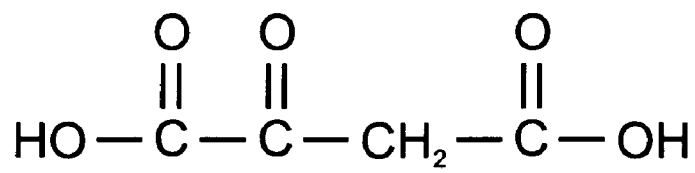
FIGS. 27A-B are schematic illustrations of the chemical structure of oxaloacetate (FIG. 27A) and diethyloxaloacetate (FIG. 27B).
Figure 27B:
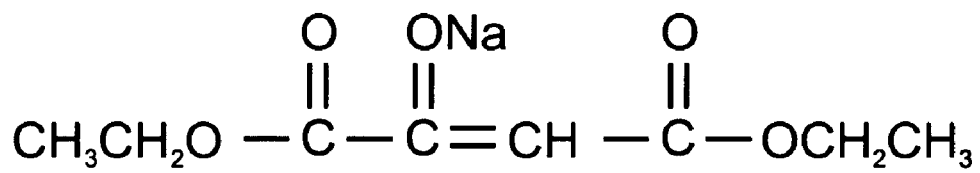
Figure 32:
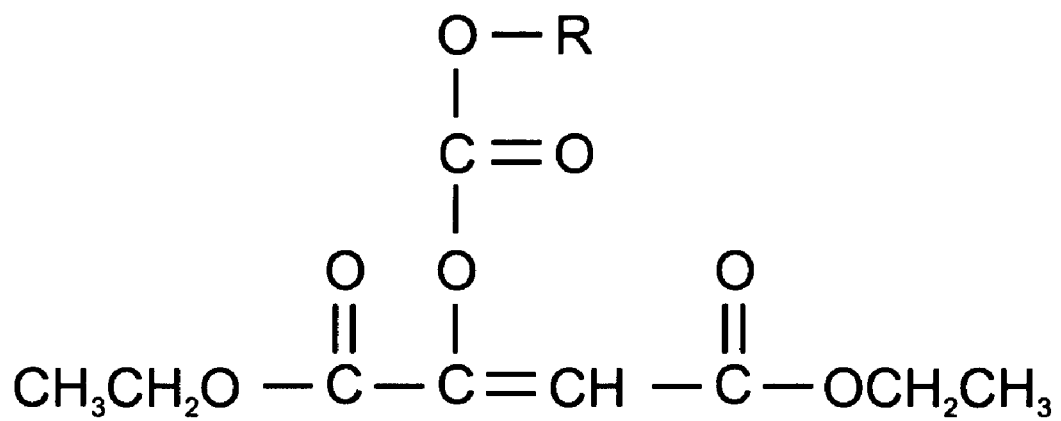
FIG. 32 shows the chemical structure of a modified diethyloxaloacetate that does not form a salt with sodium ions.

In some cases, the agent administered is modified in order to increase the therapeutic effect or reduce unwanted side effects. For example, administration of oxaloacetate diethylester is favorable over administration of oxaloacetate alone since oxaloacetate exerts its therapeutic potential at relatively high concentrations (see Example 21, FIGS. 27A-B and FIG. 32) and requires full titration of its carboxyl moieties with sodium hydroxide at 3:1 stoichiometric ratio which presents unacceptable electrolyte load above safe levels.

The agent can be administered to a subject using any one of several suitable administration modes which are further described hereinbelow with respect to the pharmaceutical compositions of the present invention.

Although the administration route is selected so as to enable provision of the agent to the blood stream of the individual in some cases, such as brain surgery, administering can be effected by direct application of the agent to exposed brain tissue.

It is well known that glutamate levels increase significantly during brain surgery involving for instance brain retraction [Xu W, Mellergard P, Ungerstedt U, Nordstrom CH, Acta Neurochir (Wien) 2002 July; 144(7):679-83)], aneurysm surgery [Kett-White R, Hutchinson P J, Al-Rawi P G, Czosnyka M, Gupta A K, Pickard J D, Kirkpatrick P J, J. Neurosurg. 2002 June; 96(6):1013-9)] or surgery of benign lesions of the posterior fossa [Reinstrup P, Stahl N, Mellergard P, Uski T, Ungerstedt U, Nordstrom CH, Neurosurgery. 2000 September; 47(3):701-9; discussion 709-10]. In such cases, topical administration of the agent described above can be utilized to substantially reduce brain glutamate levels thereby substantially reducing the risk of its deleterious effects on brain tissue, including brain tissue edema and overall excitotoxicity.

The agent utilized by the method of the present invention can be administered to an individual subject per se, or as part of a pharmaceutical composition where it is mixed with a pharmaceutically acceptable carrier (see Example 21 of the Examples section).

As used herein a "pharmaceutical composition" refers to a preparation of one or more of the active ingredients described hereinabove along with other components such as physiologically suitable carriers and excipients, penetrants etc. The purpose of a pharmaceutical composition is to facilitate administration of a compound to an organism.

Herein the term "active ingredient" refers to the preparation accountable for the biological effect (e.g., the glutamate modifying enzyme, and/or cofactors thereof).

Hereinafter, the phrases "physiologically acceptable carrier" and "pharmaceutically acceptable carrier" are interchangeably used refer to a carrier or a diluent that does not cause significant irritation to an organism and does not abrogate the biological activity and properties of the administered compound. An adjuvant is included under these phrases. One of the ingredients included in the pharmaceutically acceptable career can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration of the pharmaceutical composition of the present invention may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal and intraocular injections.

Alternately, one may administer a preparation in a local rather than systemic manner, for example, via injection of the preparation directly into a specific region of a patient's body or by direct administration to brain tissues (e.g. topical) during, for example, open brain surgery.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those-skilled in the art.

For any pharmaceutical composition used by the treatment method of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

The Examples section, which follows provides further guidance as to suitable dosages.

Depending on the severity and responsiveness of the condition to be treated, dosing can be of a single or a plurality of administrations, with course of treatment lasting from several days to several weeks or until cure is effected or diminution of the disease state or symptoms is achieved.

The amount of the pharmaceutical composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The agents of the present invention can be utilized in treating (i.e., reducing or preventing or substantially decreasing elevated concentrations of extracellular brain glutamate) of a variety of clinical conditions associated with elevated levels of extracellular brain glutamate such as brain anoxia, brain ischemia, stroke, perinatal brain damage, traumatic brain injury, bacterial meningitis, subarachnoid haemorrhage, migraine, stress, hemorrhagic shock, epilepsy, acute liver failure, glaucoma, amyotrophic lateral sclerosis, HIV, dementia, amyotrophic lateral sclerosis (ALS), spastic conditions, open heart surgery, aneurism surgery, coronary artery bypass grafting and Alzheimer's disease.

It will be appreciated that fast acting pharmaceutical compositions and administration routes described hereinabove are preferably used in treating brain anoxia, brain ischemia, stroke, perinatal brain damage, traumatic head injury, bacterial meningitis, subarachoid haemorhage, migraine, stress, hemorrhagic shock, epilepsy, acute liver failure, open heart surgery, aneurysm surgery, coronary artery bypass grafting. When continuous administration is required a continuous drug release is preferred provided that endogenous production in the depleted organ does not occur.

While reducing the present invention to practice, the present inventor has also uncovered that blood cells which are isolated from the body, depleted of glutamate and returned to the body are capable of inducing a decrease in blood glutamate levels and thereby a decrease of extracellular brain glutamate levels.

Thus according to another aspect of the present invention there is provided an additional method of reducing extracellular bran glutamate levels.

The method according to this aspect of the present invention is based upon the rational that glutamate depleted blood cells, upon transfusion into a host subject, are capable of rapidly pumping plasma glutamate towards the original cell/plasma glutamate concentration ratio (i.e., substantially 4:1), thereby promoting brain-to-blood (i.e., brain-to-plasma) glutamate efflux and reducing extracellular brain glutamate concentration (see Example 15).

The method according to this aspect of the present invention is effected by treating blood samples derived from a subject with glutamate reducing agents such as those described hereinabove, isolating cells from the blood sample and returning the cells to the subject.

Preferably the blood sample according to this aspect of the present invention is obtained from the subject for further autologous transfusion. This reduces the risk of infectious diseases such as hepatitis, which can be transferred by blood transfusions.

It will be appreciated that matching blood type (i.e., matching blood group) samples from syngeneic donors can be used for homologous transfusion although non-matching blood type samples from allogeneic donors may also be used in conjunction with a deantigenation procedure. A number of methods of deantigenation of blood group epitopes on erythrocytes (i.e., seroconversion) are known in the art such as disclosed in U.S. Pat. Nos. 5,731,426 and 5,633,130.

Blood samples are contacted with the agent of the present invention under conditions suitable for reducing blood glutamate levels to thereby obtain glutamate depleted blood cells (as described herein above and further in Examples 14-15 of the Examples section which follows).

Glutamate depleted blood cells are then separated from plasma by well known separation methods known in the art, such as by centrifugation (see Example 14 of the Examples section).

Once glutamate depleted cells are obtained they are suspended to preferably reach the original blood volume (i.e., concentration).

Suspension of glutamate depleted cells is effected using a blood substitute. "A blood substitute" refers to a blood volume expander which includes an aqueous solution of electrolytes at physiological concentration, a macromolecular oncotic agent, a biological buffer having a buffering capacity in the range of physiological pH, simple nutritive sugar or sugars, magnesium ion in a concentration sufficient to substitute for the flux of calcium across cell membranes. A blood substitute also includes a cardioplegia agent such as potassium ion in a concentration sufficient to prevent or arrest cardiac fibrillation. Numerous blood substitutes are known in the art. Examples include but are not limited to Hespan.RTM. (6% hetastarch 0.9% Sodium chloride Injection [Dupont Pharmaceuticals, Wilmington Del.]), Pentaspan (10% pentastarch in 0.9% Sodium chloride Injection [Dupont Pharmaceuticals, Wilmington Del.]) and Macrodex (6% Dextran 70 in 5% Dextrose Injection or 6% Dextran 70 in 0.9% Sodium chloride Injection [Pharmacia, Inc. Piscataway, N.J.]) and Rheomacrodex (10% Dextran 40 in 5% Dextrose Injection or 10% Dextran 40 in 0.9% Sodium chloride Injection [Pharmacia, Inc. Piscataway, N.J.]). These products are known to the medical community for particular FDA approved indications and are extensively described in the volume entitled Physicians' Desk Reference, published annually by Medical Economics Company Inc.

It will be appreciated that treated blood samples may be stored for future use. In this case, however, a sterile preservative anticoagulant such as citrate-phosphate-dextrose-adenine (CPDA) anticoagulant is preferably added to the blood substitute solution. Also added are a gram-negative antibiotic and a gram-positive antibiotic. Blood is then stored in sterile containers such as pyrogen-free containers at 4° C.

Finally, glutamate depleted blood cell solution is transfused intravenously or intravascularly as a sterile aqueous solution into the host subject, to thereby reduce extracellular brain glutamate levels.

It will be appreciated that previous studies have emphasized the relative impermeability of erythrocytes to extracellular glutamate [Young (1980) Proc. R. Soc. Lond. B. Biol. Sci. 209:355-75; Pico (1992) Int. J. Biochem. Cell Biol. 27(8):761-5 and Culliford (1995) J. Physiol. 489(Pt3):755-65]. However, these were done in the presence of an unfavorable glutamate concentration gradient.

Thus, not only does the present invention exhibits erythrocytes permeability to glutamate, thereby explaining the still unclear blood pool of intracellular glutamate, but provides with a blood exchange strategy which can be utilized in emergency conditions such as stroke and head trauma, in which a rapid reduction in CSF/ISF glutamate is desired.

The above described methodology can be effected using currently available devices such as incubators and centrifuges (see the Examples section for further detail) or a dedicated device which is designed and configured for obtaining a blood sample from the subject, processing it as described above and returning glutamate depleted blood cells to the subject or to a different individual which requires treatment.

Such a device preferably includes a blood inlet, a blood outlet and a chamber for processing blood and retrieving processed blood cells. At least one of the blood inlet and outlet is connected to blood flow tubing, which carries a connector spaced from the device for access to the vascular system of the subject.

Blood treatment devices providing an extracorporeal blood circuit to direct blood to a treatment device from the individual subject, and then to return the blood to the individual subject are well known in the art. Such treatment devices include, but are not limited to hemodialysis units, plasmapheresis units and hemofiltration units, which enable blood flow across a unit, which carries a fixed bed of enzyme or other bioactive agent.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology"; W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

In-Vitro Scavenging of Blood Glutamate by Activation of Resident Enzymes

Several intractable brain pathological conditions are characterized by the presence of excess glutamate in brain interstitial fluid. In order to increase the driving force for an enhanced brain-to-blood efflux of glutamate levels, conditions allowing decreased blood glutamate levels were determined in-vitro.

Since both glutamate pyruvate transaminase (GPT) and glutamate oxaloacetate transaminase (GOT) catalyze the degradation of glutamate (into 2-ketoglutarate—forward reaction) and its synthesis (from 2-ketoglutarate—reverse reaction) with equal efficiency, it was tested whether the administration of pyruvate and oxaloacetate to blood, results in a shifting of the equilibrium towards the degradation of glutamate i.e. the forward reaction. Materials and Experimental procedures Experimental Procedures Materials—Glutamate dehydrogenase was purchased from Roche (Roche diagnostics, GmBH, Mannheim, Germany). Unless otherwise noted all reagents and chemicals were purchased from Sigma, Rehovot, Israel.

Animals—Adult Sprague Dawley rats (SPD) (200-250 g body weight) were anaesthetized intraperitoneally with 40 mg ketamine and 5 mg xylazine/Kg body weight.

Induction of rat blood glutamate metabolism and glutamate concentration determination—Fresh rat blood samples incubated at 37° C. were supplemented every 15 minutes or as noted with oxaloacetate and/or pyruvate (final concentration of 1 mM at pH 7.4).

At indicated time intervals, 150 µl aliquots were removed and centrifuged at 1,300×g for 7 minutes. Plasma volume (i.e., supernatant) was measured and was combined with identical volume of perchloric acid (PCA) to precipitate protein content. Precipitation was allowed to proceed for 10 minutes on ice and thereafter samples were centrifuged. Cell pellet (i.e., erythrocytes, lymphocytes and platelets) was lysed by osmotic shock following resuspension in double distilled water up to a final volume of 150 µl. A second step of protein precipitation was then performed by adding 150 µl of PCA [1 mM]. Plasma and cell PCA-precipitated fractions Were centrifuged at 16,000×g for 10 minutes and pellets were discarded.

Supernatant glutamate concentration was determined according to the fluorometric procedure of Graham and Aprison [(1996) Anal. Biochem. 15(3):487-97]. In brief: 20 µl aliquot of PCA precipitated fraction was added to 480 µl HG buffer containing 15 u of glutamate dehydrogenase in 0.2 mM NAD, 0.3 M glycine, 2.4% hydrazine hydrate adjusted to pH 6.8 with $H_2SO_4$ [1 N] and incubated at room temperature for 30-45 minutes. Fluorescence was measured at 460 nm following excitation at 350 nm. All measurements were performed alongside a glutamate standard curve at a glutamate concentration range of 0-6 μM. All glutamate measurements were performed in duplicates.

Results—Glutamate levels in whole rat blood samples were determined in vitro, under various incubation conditions at 37° C. As is evident from FIG. 1A, glutamate levels in blood increased steadily upon incubation of rat blood at 37° C. (filled diamonds). A significant increase in blood glutamate was exhibited upon incubation of blood with 2.5 u/ml GPT at time zero (empty circles) indicating the presence of significant endogenous pools of 2-ketoglutarate and alanine, which caused the synthesis of glutamate (i.e., reverse reaction). A complete reversion, however, was detected following addition of pyruvate, at a final concentration of 1 mM, at t zero in the absence (closed squares and black arrow at t=0) or presence of 2.5 u/ml GPT (closed circles) or when pyruvate was added at t=0, 15, 30 minutes (empty squares and black arrows). These results showed that activation of GPT by pyruvate caused a decrease in glutamate levels. Interestingly, under these conditions glutamate reduction was transient as soon after the consumption of pyruvate (about 15-20 minutes after its last addition to blood) and the concomitant production of alanine and 2-ketoglutarate, the latter apparently was converted back into glutamate.

Supplementing blood with 1 mM Pyr (closed squares), 1 mM oxaloacetate (closed triangles) or a mixture of the two (closed diamonds), at time 0, 15 and 30 minutes resulted in a more rapid activation of GOT by oxaloacetate, resulting in greater decline in glutamate levels, unparalleled by pyruvate addition. No synergy was evident for this effect. These results suggest that GOT/GPT-mediated glutamate conversion reached a maximal extent limited by the concomitant 2-ketoglutarate concentration build-up driving GPT and GOT reverse reactions.

Altogether, these results showed that the levels of whole blood glutamate can be manipulated in-vitro by the addition of GOT and/or GPT glutamate co-substrates.

Example 2

Effects of Pyruvate and Oxaloacetate on Glutamate Levels in Different Blood Components Whole blood can be divided into two major fractions, plasma and blood cells (i.e., erythrocytes, leukocytes and platelets). Since potentially therapeutic effects are proposed herein to be mediated via decreases in plasma glutamate concentration resulting in compensatory release from brain glutamate reserves, it is essential to determine glutamate levels in plasma and cellular pools following activation of endogenous GPT and GOT.

Figure 2A:
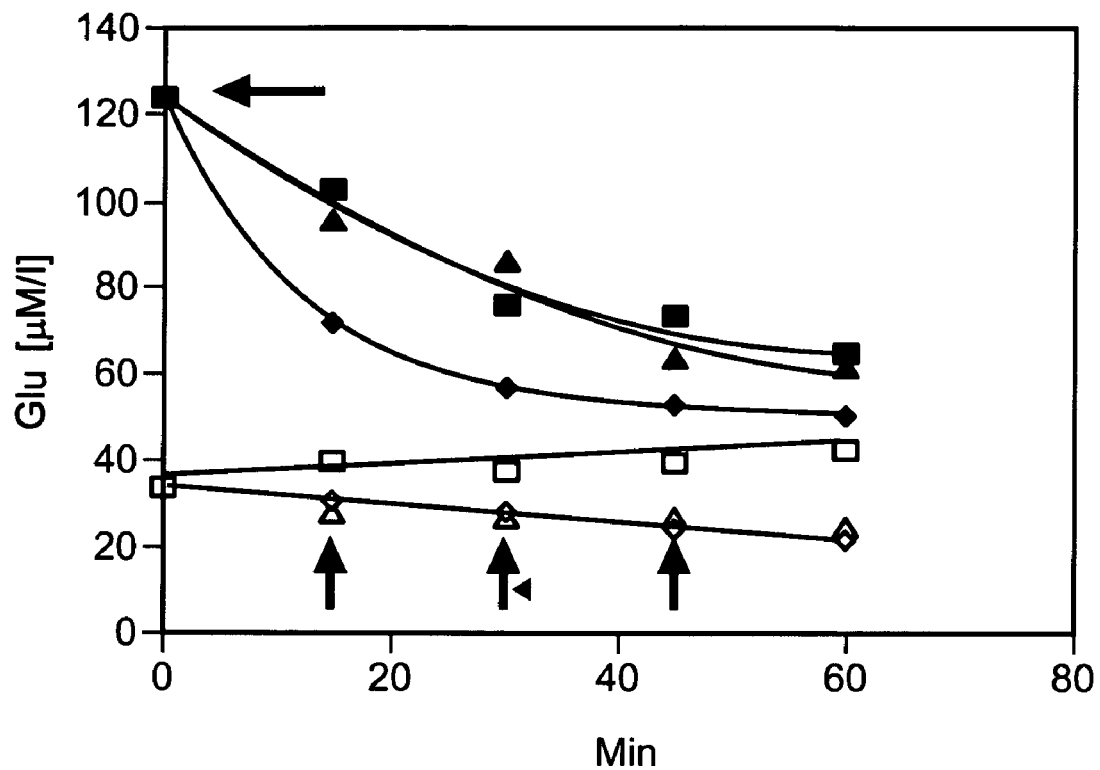
FIG. 2A is a graphic representation of glutamate levels in blood cells (closed symbols) and plasma (open symbols) as determined in-vitro. 1 mM of pyruvate (squares) or 1 mM of oxaloacetate (triangles) or the combination thereof (diamonds) to blood were added to blood samples at the indicated times (upward arrows indicate times). Glutamate levels in the different blood compartments were then followed; Closed symbols: blood cell compartment; open symbols: blood plasma). All incubations were conducted at 37° C. and each point represents the average of at least two glutamate determinations.
Figure 2B:
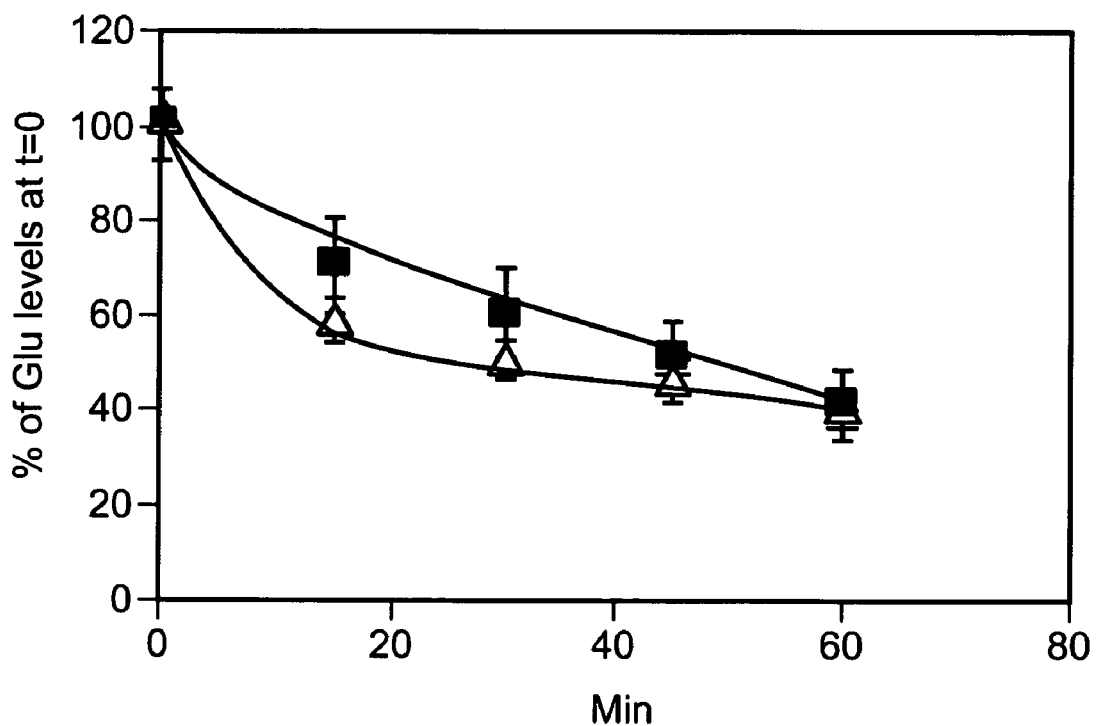
FIG. 2B is a graphic representation of glutamate conversion in blood cellular pool (open triangles) and in plasma (closed squares) following the repeated additions (at t=0, 15, 30, 45 min) to blood of Pyruvate and oxaloacetate (both at a final 1 mM concentration). Each point represents the average of 8 experiments+standard error of the mean.

Results—Glutamate levels were therefore determined individually in blood cell fractions (closed symbols) and in plasma (open symbols), following repeated additions (arrows) of 1 mM pyruvate (squares), 1 mM oxaloacetate (triangles) or of a mixture of 1 mM pyruvate and 1 mM oxaloacetate (diamonds)(FIG. 2A). Glutamate determination was conducted as described in Example 1. The addition of pyruvate or oxaloacetate caused a comparable reduction in intracellular glutamate concentration, however, while pyruvate significantly increased plasma glutamate concentration, oxaloacetate caused a significant reduction in plasma glutamate concentration.

Figure 1B:
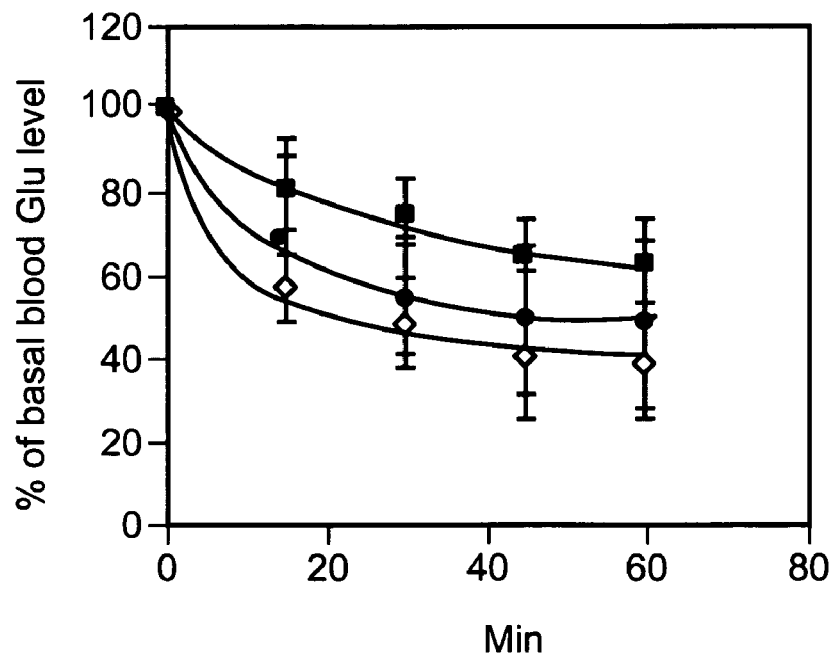
FIG. 1B is a graphic representation of glutamate levels as a function of time. Blood was combined with 1 mM Pyruvate (Pyr, closed squares), 1 mM oxaloacetate (closed circles) or a mixture of the two (open diamonds), at time 0, 15 and 30 minutes resulted in a more rapid activation of blood resident GOT by oxaloacetate, resulting in greater decline in glutamate levels, unparalleled by pyruvate addition. No synergy was evident for this effect.

When combined, pyruvate and oxaloacetate had a synergistic effect, decreasing both concentrations of glutamate. The results obtained suggested that, once taken up intracellularly, presumably via monocarboxylate transporters, pyruvate and oxaloacetate are able to activate intracellular GPT and GOT. Since the intracellular glutamate concentration (120+/−4.9 μM) is about 3 times greater than that of plasma (40.8+/−5.8 μM), the data are supportive of the interpretation that the decrease in intracellular glutamate concentrations is expected to account principally for the decrease of blood glutamate observed in FIG. 1. Analysis of the initial rates of glutamate conversion showed that the conversion rates in the cell pool (3.3 percent/minute) was about 2.5 times higher than that in plasma (1.3 percent/minute). These rates were compatible with the Glutamate concentrations observed in the respective pools and in line with the glutamate Km values of GOT/GPT in the mM range providing that enzyme levels were similar in both pools.

Example 3

Effective In Vitro Levels of Pyruvate and Oxaloacetate

Figure 3:
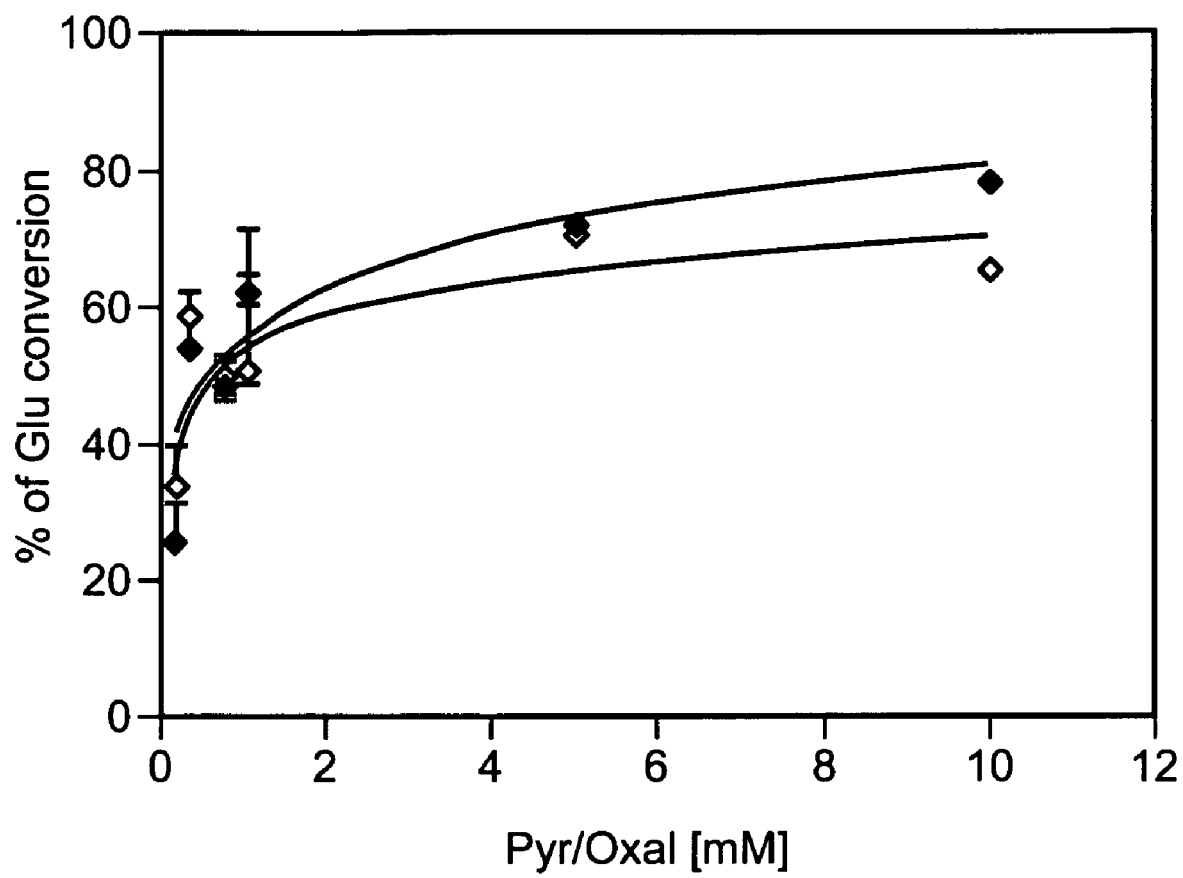
FIG. 3 is a graphic representation of glutamate conversion over the course of 60 minutes, following the addition of increasing concentrations of an equimolar mixture of Pyruvate and oxaloacetate to blood samples. Analysis of the cellular pool (filled diamonds) versus plasma (open diamonds) glutamate conversion revealed slightly greater conversion for the former. Each point represents an average of at least two glutamate determinations.

Since previous examples have indicated that combined pyruvate and oxaloacetate administration is effective in lowering plasma and blood cell intracellular glutamate concentrations, it was essential to determine optimal concentrations of pyruvate and oxaloacetate for potential therapeutic application Results—The extent of glutamate degradation reached after 60 minutes following the addition of increasing concentrations of pyruvate and oxaloacetate to plasma and blood cell fractions was determined. As shown in FIG. 3, half of the maximal effect was observed at a sub mM concentration in line with prior art Km values for pyruvate and oxaloacetate. Saturation was observed at a concentration of about 5 mM.

As both GPT and GOT utilize pyridoxal phosphate as a cofactor the addition of 15 μM pyridoxal phosphate was evaluated in terms of its ability to enhance pyruvate and oxaloacetate-mediated decreases in cellular or plasma glutamate concentration. No significant effects of pyridoxal phosphate were observed (data not shown).

Thus optimal concentrations of pyruvate and oxaloacetate for mediating blood glutamate reduction effects were determined, at a concentration likely to provide therapeutic value and application.

Example 4

Depletion of 2-ketoglutarate as a Means of Enhancing Glutamate Degradation In Vitro Glutamate is converted by the enzymes GOT and GPT into 2-ketoglutarate. Accumulation of 2-ketoglutarate, however, can drive the GOT and GPT reverse reactions, resulting in glutamate production. It is possible, for the 2-ketoglutarate product to serve as a substrate for the 2-ketoglutarate dehydrogenase enzyme, resulting in conversion of newly accumulated 2-ketoglutarate into succinyl CoA. The conversion requires the presence of the cofactors CoA and NAD. Since thiamine pyrophosphate and lipoic acid are cofactors of the enzyme 2-ketoglutarate dehydrogenase, it was hypothesized that their addition to blood samples in the presence of pyruvate and oxaloacetate results in stimulation of glutamate degradation, favoring the forward reaction.

Figure 4A:
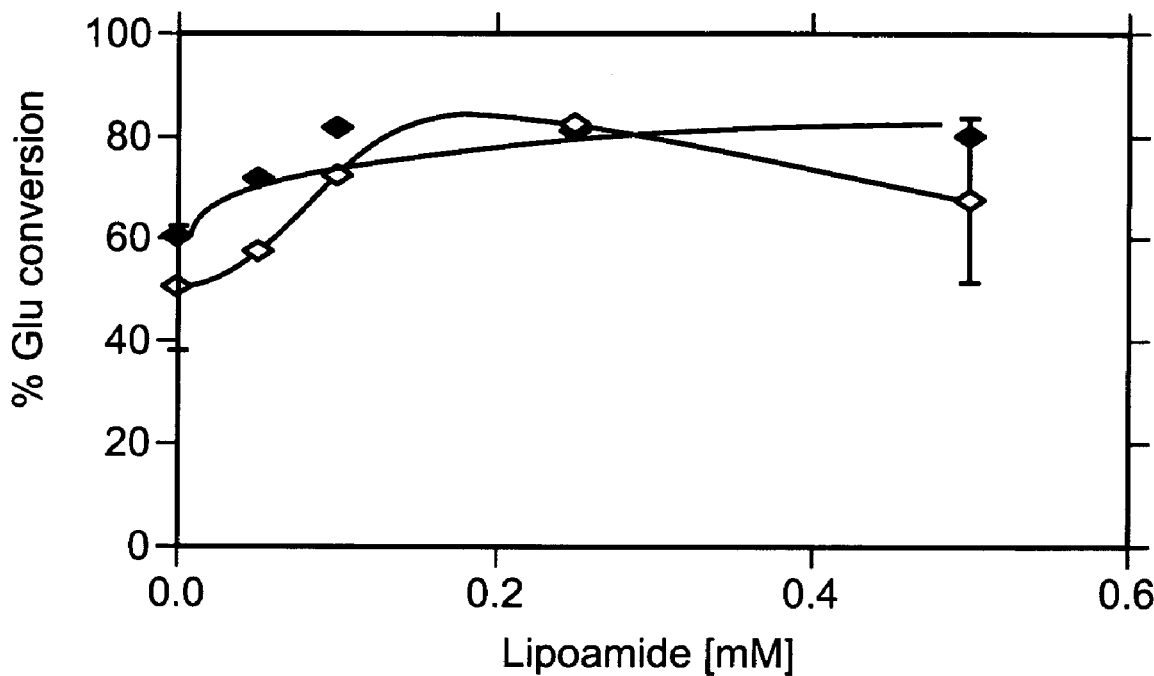
FIGS. 4A-B are graphs depicting the extent of glutamate conversion reached after 60 minutes following repeated additions of increasing concentrations of lipoamide (FIG. 4A) and thiaminepyrophosphate (FIG. 4B) to blood, in the presence of a mixture of 1 mM Pyr and 1 mM oxaloacetate. Blood was separated into cellular (filled diamonds) and plasma (open diamonds) fractions that were analyzed separately. Each point represents the average of at least two glutamate determinations.
Figure 4B:
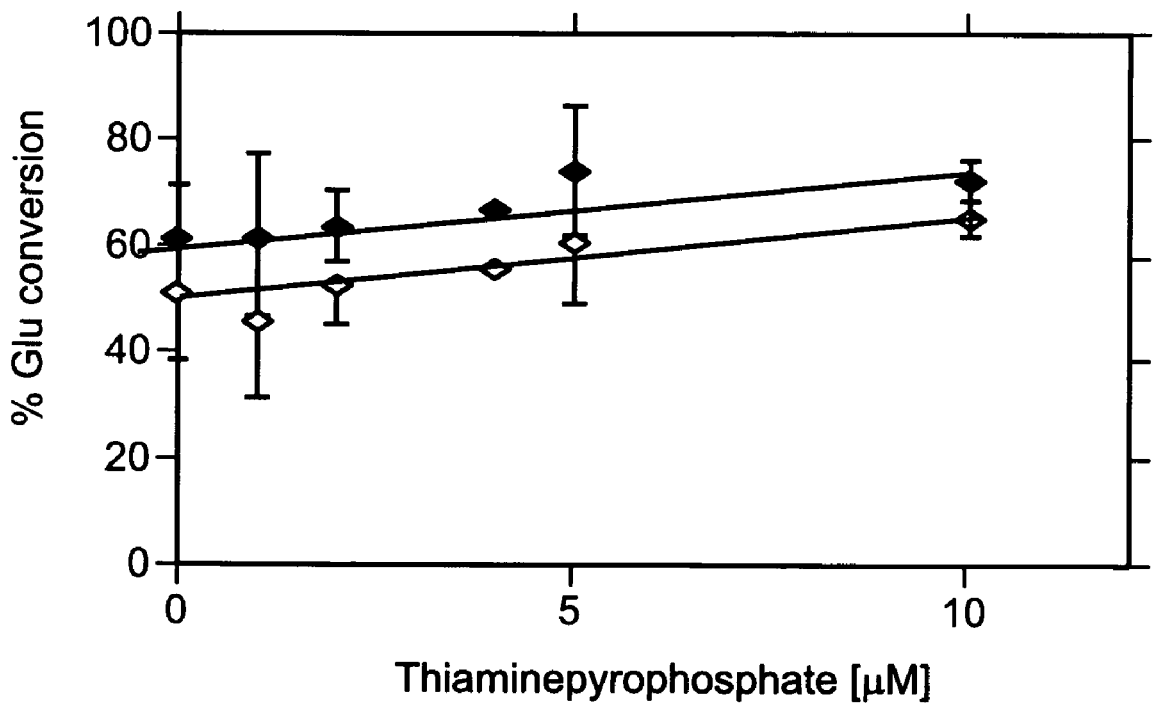

Results—In order to test the above hypothesis, 1 mM pyruvate and 1 mM oxaloacetate were added to blood samples in conjunction with the repeated additions of increasing concentrations of lipoamide (FIG. 4A) and thiamine pyrophosphate (FIG. 4B) and glutamate concentration was assayed over the course of 60 minutes. The addition of 2-ketoglutarate dehydrogenase cofactors demonstrably increased the conversion of glutamate by about 15-50%.

Figure 5A:
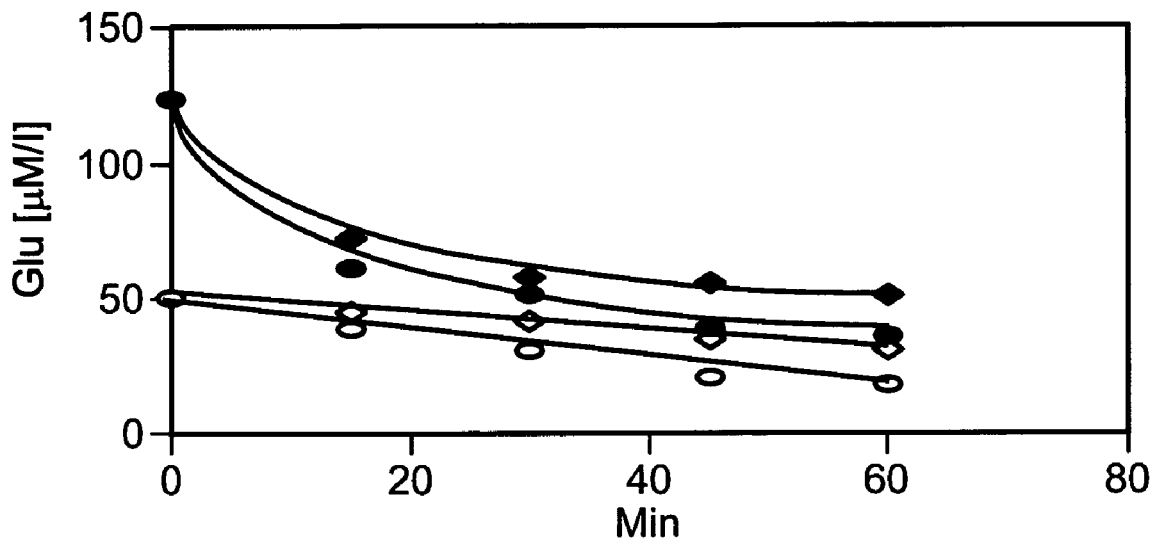
FIGS. 5A-B are graphs depicting the effects of 10 μM thiaminepyrophosphate (FIG. 5A) and 0.5 mM lipoamide (FIG. 5B) on the levels of glutamate conversion produced by a mixture of 1 mM pyruvate and 1 mM oxaloacetate. The cellular fraction was treated as follows, filled diamonds represent cells that were treated with oxaloacetate and pyruvate. Filled circles represent cells that were treated with oxaloacetate and pyruvate with an addition of 10 μM thiaminepyrophosphate (FIG. 5A) or 0.5 mM lipoamide (FIG. 5B). Plasma treated with oxaloacetate and pyruvate is represented by open diamonds. Open circles represent the addition of 10 μM thiaminepyrophosphate (FIG. 5A) or 0.5 mM lipoamide (FIG. 5B). Each point represents the average of at least two glutamate determinations.
Figure 5B:
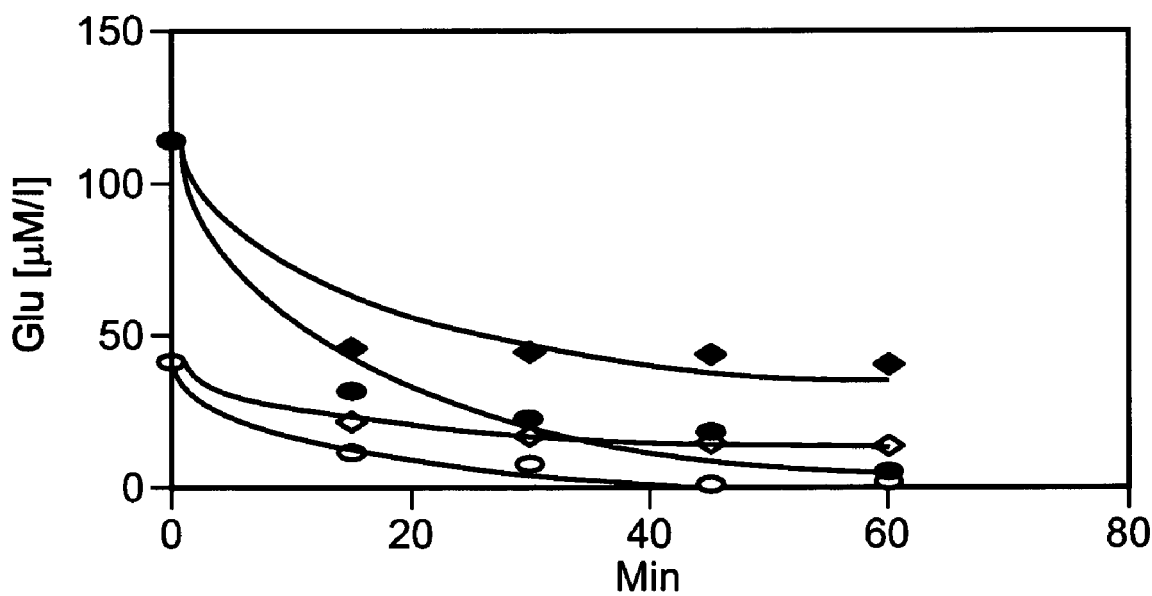

Glutamate conversion was a function of 2-ketoglutarate dehydrogenase cofactor concentration, yet these effects may also be evaluated as a function of time (FIGS. 5A-B). Both thiaminepyrophosphate (FIG. 5A) and lipoamide (FIG. 5B) dramatically increased the rate of glutamate conversion (in a range of 20-50%) in addition to the extent of conversion demonstrated previously. These data may be interpreted as illustrative of 2-ketoglutarate dehydrogenase activation facilitating GOT/GPT-mediated glutamate scavenging in line with the concept that the activation of the 2-ketoglutarate dehydrogenase facilitates the GOT/GPT-mediated glutamate degradation, these results suggest that the addition to blood of sub mM concentrations of Pyruvate and oxaloacetate (Example 3) in combination with either lipoamide or thiaminepyrophosphate is an additional/alternative means of decreasing plasma glutamate levels, for achieving therapeutic effect.

Example 5

The Effect of Glutamate Dehydrogenase Co-factors on Glutamate Conversion

Glutamate conversion is mediated by a process of oxidative deamination. This reaction is catalyzed by the enzyme glutamate dehydrogenase (GDH), which is unusual in its ability to utilize either cofactor, $NAD^+$ or $NADP^+$. The multimeric protein, GDH is also allosterically activated by ADP and Leucine. It was therefore essential to determine whether, and to what extent these cofactors mediated affected GDH mediated glutamate degradation.

Figure 6:
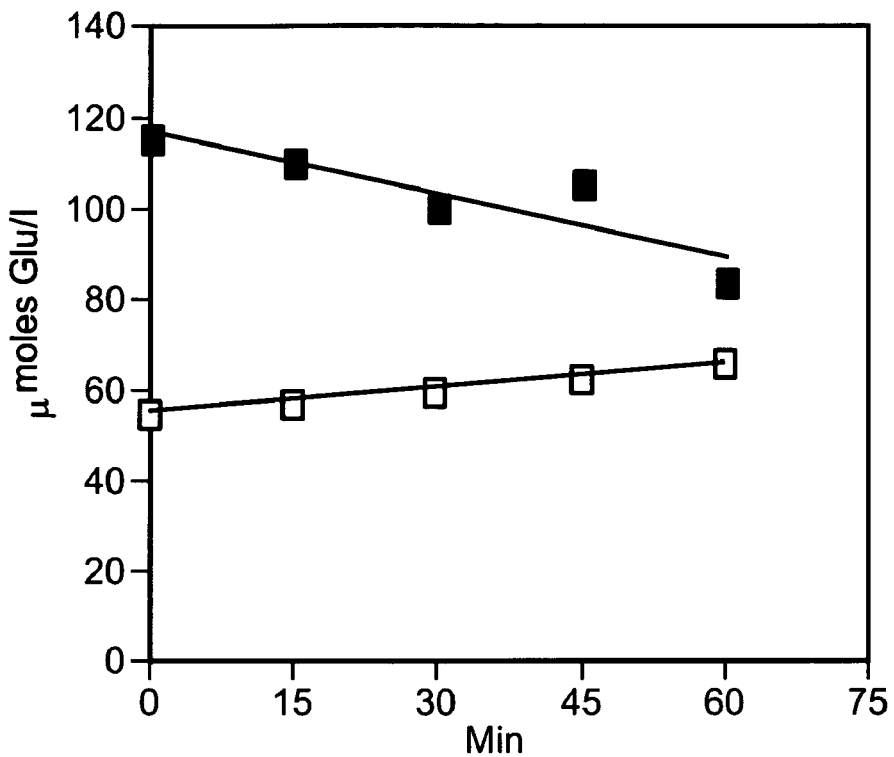
FIG. 6 is a graph depicting inverse effects of repeated addition of NAD to blood on blood cellular compartment (filled squares) (diminishing) and plasma glutamate (open squares) (increasing) levels. Each point represents the average of at least two glutamate determinations.

Results—Incubation of blood with NAD, Leu or ADP either separately or in combination, resulted in differential effects on glutamate concentrations in the two blood compartments, in vitro (FIG. 6). While a decrease in blood cell glutamate levels was observed following the addition of NAD, an increase in plasma glutamate levels was evident. While incubation with NAD, Leucine (Leu) or ADP either separately or in combination increased plasma glutamate levels, the addition of NAD alone or in combination with Leu and ADP resulted in a decrease in cellular glutamate. The addition of either Leu or ADP individually, however, did not significantly alter glutamate levels.

Although these results suggest a role for NAD as a putative in-vitro activator of GDH in the cellular compartment, the 2-ketoglutarate product was converted back into glutamate probably via the action of plasma GOT and/or GPT. Therefore activation of GDH is not a preferred means of decreasing plasma glutamate.

Example 6

In-Vivo Scavenging of Blood Glutamate by Activation of Endogenous Enzymes

Materials and Experimental Methods

Materials—Glutamate, sodium pyruvate, sodium oxaloacetate, NADH, lactate dehydrogenase and malate dehydrogenase were purchased from Sigma. Glutamate dehydrogenase was purchased from Boeringer.

Animals—Anesthesia of adult Sprague Dawley rats (200-250 grams in weight) was performed as described in Example 1.

Catheterization of the tail vein (for drug injections) and of the femoral vein (for blood aliquots withdrawals) was performed using PE10 polyethylene tubing linked to PE50 polyethylene tubing. All catheters were secured with 5-0 silk thread and flushed with heparin (3-5 µl of 182 U/ml). Body temperature was maintained with a lamp and rectal temperature was monitored. Rat pulse rate was monitored using a Periflux system 500 and a laser Doppler probe placed onto the skull.

Intravenous injections of the various compounds diluted in phosphate buffered saline (PBS) were carried out at a rate of 0.05 ml/minute for 30 min with a Pharmacia pump P-1. During injections and at several time points after the injections (in general, every 15 min), Glutamate concentration determination—Blood aliquots of 150 µl were retrieved from the rat femoral vein. Determination of glutamate concentration was effected as described in Example 1.

Glutamate analyses of in-vivo treated blood samples were carried out according to the fluorometric procedure of Graham and Aprison [(1996) Anal. Biochem. 15(3):487-97].Pyruvate concentration determination—Blood Pyruvate concentration was measured using the Sigma Diagnostics Pyruvate reagents according to manufacturer's instructions. In brief: the procedure utilizes lactate dehydrogenase which in the presence of excess NADH catalyzes almost complete conversion of pyruvate into lactate with a concomitant production of NAD. The reduction of absorbance at 340 nm due to the oxidation of NADH into NAD is the measure of the amount of pyruvate originally present.

Oxaloacetate concentration determination—Blood oxaloacetate concentration was measured using the same procedure as for pyruvate but using malate dehydrogenase which catalyses the conversion of oxaloacetate into malate along with the oxidation of NADH into NAD.

Example 7

In Vivo Conditions for Maximizing GOT and GPT Glutamate Degradation Effectiveness Examples 2-5 established the in vitro conditions under which the activation of blood resident enzymes i.e., glutamate pyruvate transaminase (GPT) and glutamate-oxaloacetate transaminase (GOT) with their respective co-substrates pyruvate and oxaloacetate, cause a decrease in blood glutamate concentration. The following experiments reveal optimal conditions facilitating reduction of blood glutamate levels in vivo.

Since a concentration of 1 mM pyruvate and/or Oxaloacetate was found to effectively reduce blood glutamate in vitro (see Example 2) an attempt to achieve similar in-vivo concentration of each of the co-factors was effected.

Taking into consideration that the rat blood volume is about 5.5 to 7 ml per 100 g body weight (Van Dongen et al. 1990; Waynforth and Flecknell, 1992), the effects of a single intravenous injection of a mixed solution in PBS of pyruvate and oxaloacetate, each at a dose of 30 µMoles (2 ml of a 15 mM solution) on rat glutamate levels was tested. However, no significant effects on blood glutamate were observed even when the intravenously injected doses were increased to 200 µMoles (data not shown) or when up to 1 mmole was administered either subcutaneously or intraperitoneally.

Figure 7:
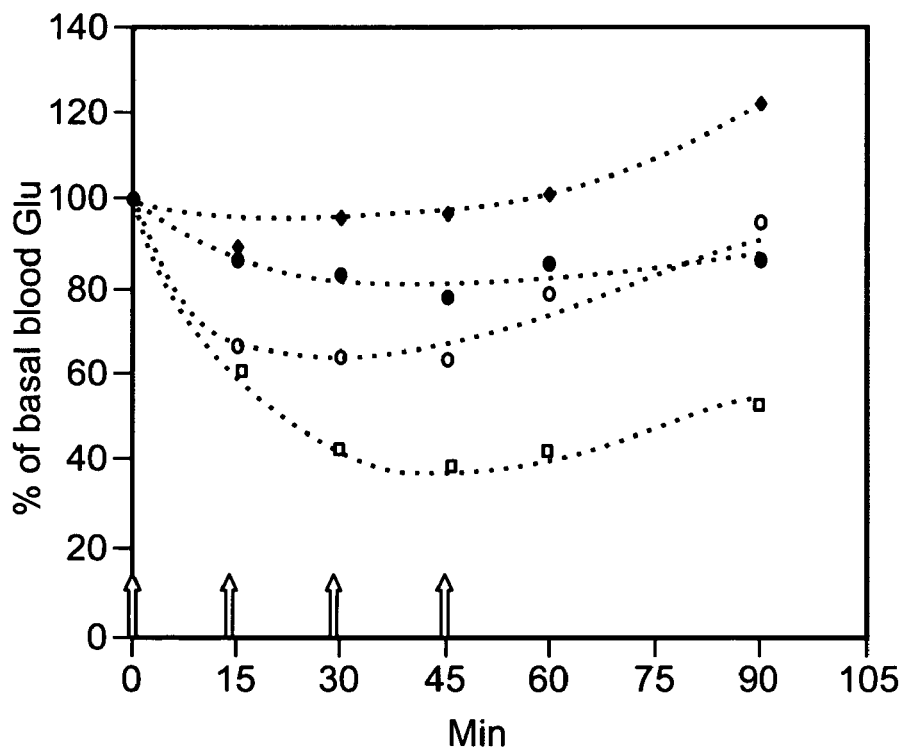
FIG. 7 graphically depicts blood glutamate levels in vivo (filled symbols) and in vitro (open symbols) following repeated administrations (every 15 minutes from t0 up to t=45 min; open arrows) of 200 μl of PBS containing pyruvate/oxaloacetate (30 μmoles each) in the presence (circles) or absence of NAD and ADP (black diamonds and open squares, respectively, 3 μmoles each). Averages of two glutamate level measurements are represented. One representative experiment out of 4 performed is shown.

As shown in FIG. 7, when four successive intravenous injections of pyruvate and oxaloacetate, each at a dose of 30 µmole, were performed (at 15 minute intervals), in the absence or presence of glutamate dehydrogenase (GDH) activators (3 μmoles each) including leucine, NAD and ADP, a 10-20% decrease in blood glutamate levels was observed. Under parallel in vitro conditions, a 40-60% decrease of blood glutamate levels took place. In both cases, the decrease was transient and an increase in blood glutamate levels took place soon after the third or fourth injection.

Example 8

Pharmacokinetics of Oxaloacetate and Pyruvate In Vivo

Since the previous example demonstrated that repeated injections were required for optimal effects mediated via administration of oxaloacetate and pyruvate, it was of interest to determine whether continuous supply via intravenous catheter would produce alternative or enhanced results.

Figure 8:
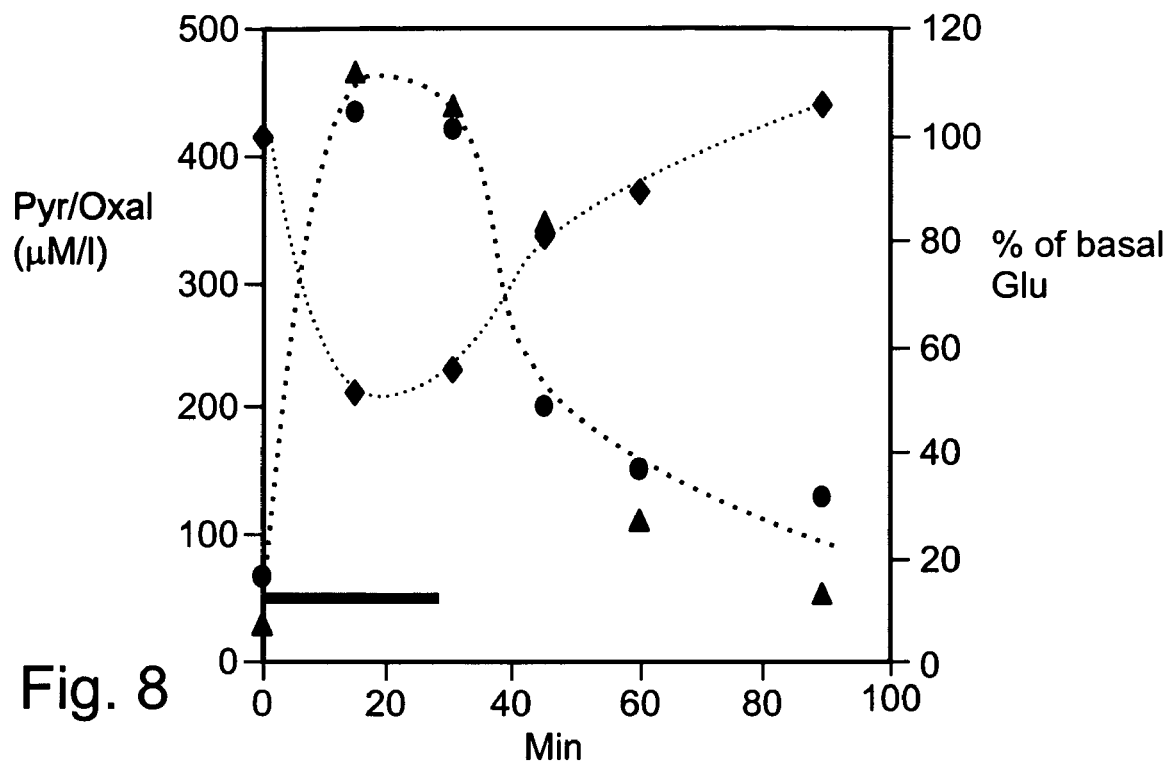
FIG. 8 graphically depicts diminished blood glutamate levels in vivo (blue diamonds) in response to intravenous administration of pyruvate (circles) and oxaloacetate (triangles) (50 μmoles each min) for a duration of 30 minutes (black bar). The blood levels of pyruvate (squares) and oxaloacetate (triangles) were monitored in parallel. Results are averages of two determinations.

Results—The effect on glutamate levels via pyruvate and oxaloacetate administration through an intravenous catheter at a rate of 50 μMoles/minute for a duration of 30 minutes was determined. Blood concentrations of glutamate, pyruvate and oxaloacetate were monitored in parallel. As shown in FIG. 8, a significant build up of both pyruvate and oxaloacetate took place following 15 minutes of treatment, which was accompanied by a marked decrease in blood glutamate. However, as soon as the administration of pyruvate and oxaloacetate was stopped, their blood concentration decreased and the glutamate level increased concomitantly.

Example 9

Figure 9:
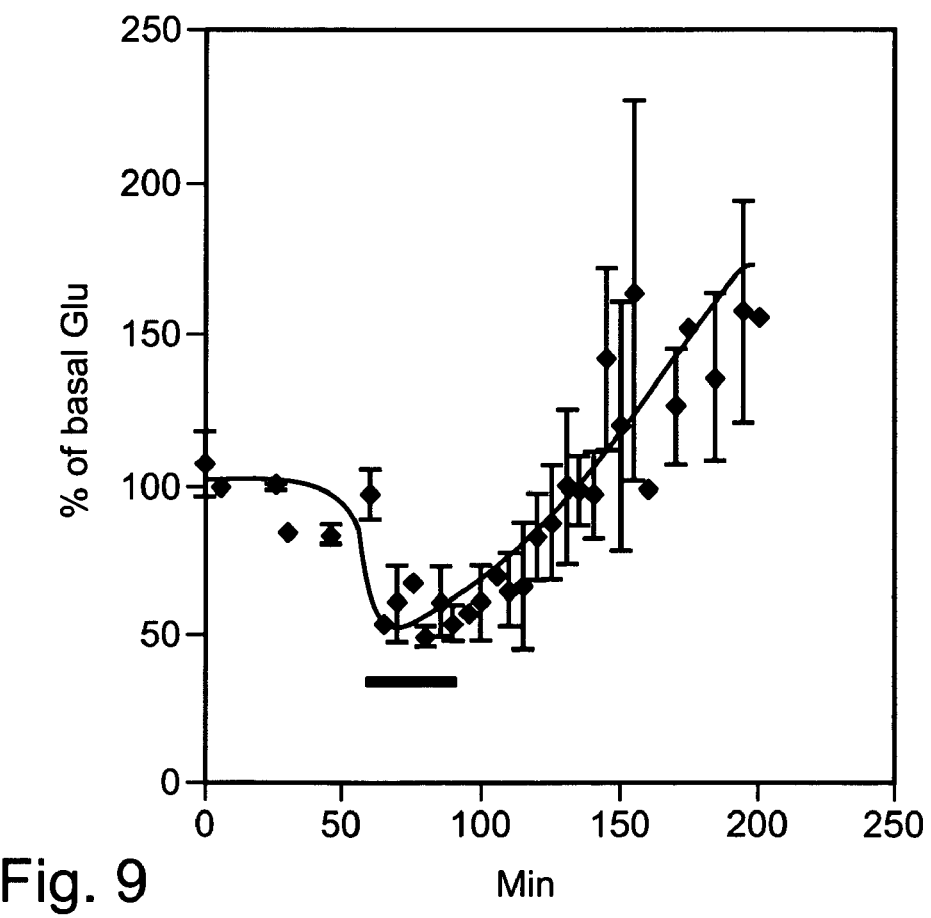
FIG. 9 depicts changing in vivo blood glutamate levels following intravenous administration of pyruvate and oxaloacetate (50 μmoles each/minute) for a duration of 30 minutes (black bar). The plot represents an average of two glutamate determinations from 7 experiments.

Increased Blood Glutamate Levels Following Long-course Exposure to Oxaloacetate And Pyruvate Previous examples indicated that short-course exposure to pyruvate/oxaloacetate resulted in a reversible decrease in blood glutamate levels. It was therefore of interest to determine whether longer exposure resulted in a similar result. Continuous monitoring of glutamate levels, as above, though over the course of approximately 200 minutes following the completion of pyruvate and oxaloacetate infusion, resulted in a clear increase in glutamate levels, above blood basal levels (FIG. 9). The dramatically enhanced glutamate levels found suggested that the increase was not only a function of GOT/GPT reaction reversal (as a result of the build-up of the enzymatic products, 2-ketoglutarate, alanine and aspartate) but rather attests to the existence of additional physiological compensatory processes. Administration of pyruvate and oxaloacetate under these circumstances did not result in any changes in rat pulse rate or rectal temperature yet did result in a diuretic effect, most likely a result of increased blood Na+ ion concentration since pyruvate and oxaloacetate were injected as sodium salts.

Example 10

Elimination of 2-ketoglutarate as a Means of Enhancing Glutamate Degradation In Vivo As described in Example 4 hereinabove, the in vitro addition of lipoamide or of thiaminepyrophosphate (two cofactors for the 2-ketoglutarate dehydrogenase enzyme) to blood limits the GOT and GPT reverse reactions. These reverse reactions are hindered by a decreased availability of 2-ketoglutarate due to its conversion to succinyl CoA. For effective therapeutic application, it was necessary to evaluate this phenomenon in vivo.

Figure 10:
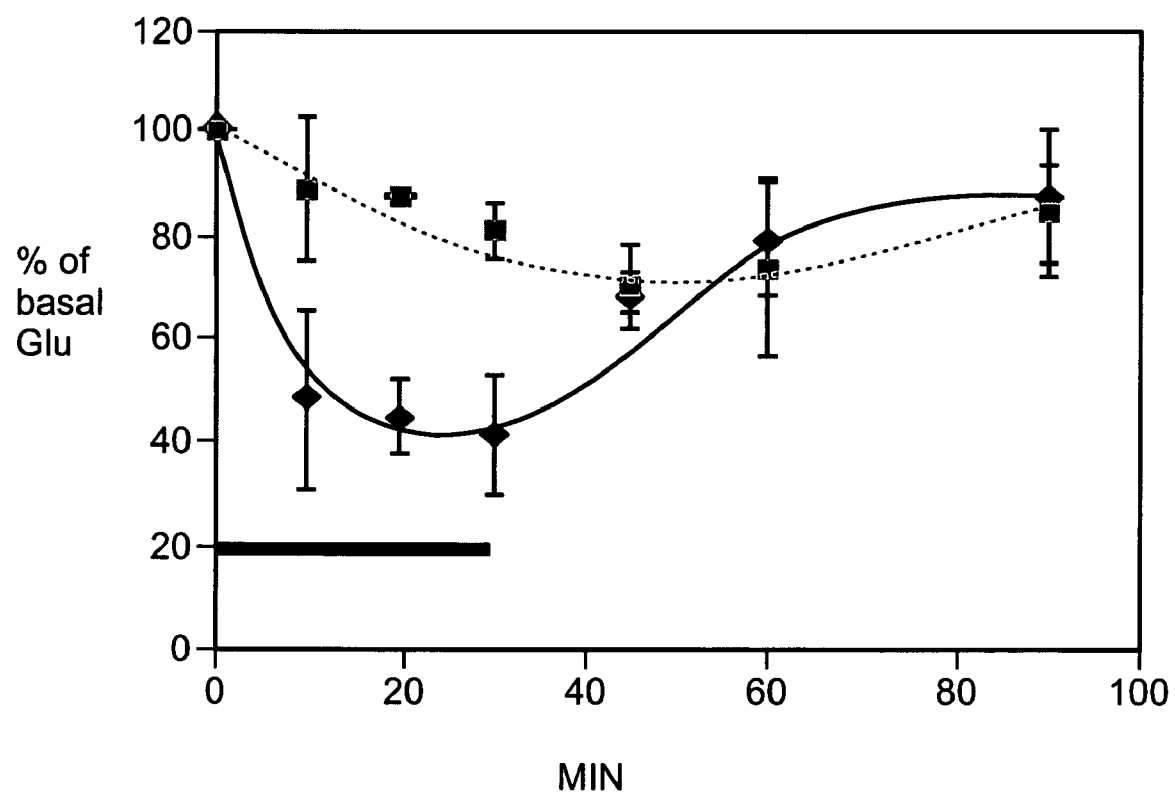
FIG. 10 depicts changing in vivo of blood glutamate levels following intravenous administration of a PBS solution containing: 150 mM pyruvate, 150 mM oxaloacetate and 1.5 mM lipoamide administered at a rate of 50 μl/min, for a duration of 30 minutes (black bar). The levels of glutamate in blood (circles), blood cell compartment (black diamonds) and plasma (grey squares) are presented as averages of two glutamate determinations. One representative experiment out of 2 performed is shown.

Results—To determine whether this result was consistent in vivo, rats were infused for 30 minutes with pyruvate and oxaloacetate (7.5 μmoles/minute) together with lipoamide (75 nmoles/minute) or thiaminepyrosphate (5 mmole/minute). In these experiments, glutamate levels were monitored in whole blood as well as in its plasma and cell fractions (FIG. 10). Analysis of glutamate levels in blood plasma and cell pools revealed that the initial glutamate conversion rate (defined as the % glutamate conversion in the first 15 minutes) in the cell pool (3.3%/minute) differed significantly from that in plasma (0.6%/minute). Moreover, though the extent (60%) and rate of glutamate conversion in the cell pool measured in vivo was similar to in vitro levels, the extent of glutamate conversion measured for plasma in vivo is about half that measured in vitro. Decreased plasma glutamate levels produced by the activation of GOT/GPT apparently stimulate compensatory mechanisms in peripheral organs for glutamate release, in an attempt to normalize circulating glutamate concentrations.

Example 11

Rates of Glutamate Uptake in Glutamate-depleted Blood Cells

The preceding examples demonstrated decreased glutamate levels, in vitro and in vivo, following activation of the blood resident enzymes glutamate-pyruvate transaminase (GPT) and glutamate-oxaloacetate transaminase (GOT) via the addition of the glutamate co-substrates pyruvate and oxaloacetate. Repeated circulating exposure to pyruvate and oxaloacetate results in a decrease in glutamate levels in the plasma, as well as in the blood cell compartment, which contains 80% of blood glutamate levels.

Because of these findings, it was reasoned that a blood exchange strategy resulting in reduced circulating glutamate levels may be effected via glutamate-depletion of the blood cell compartment. As a result, rapid, active influx of plasma glutamate would occur, in order to normalize the cell/plasma glutamate concentration ratio of 4.

Figure 11:
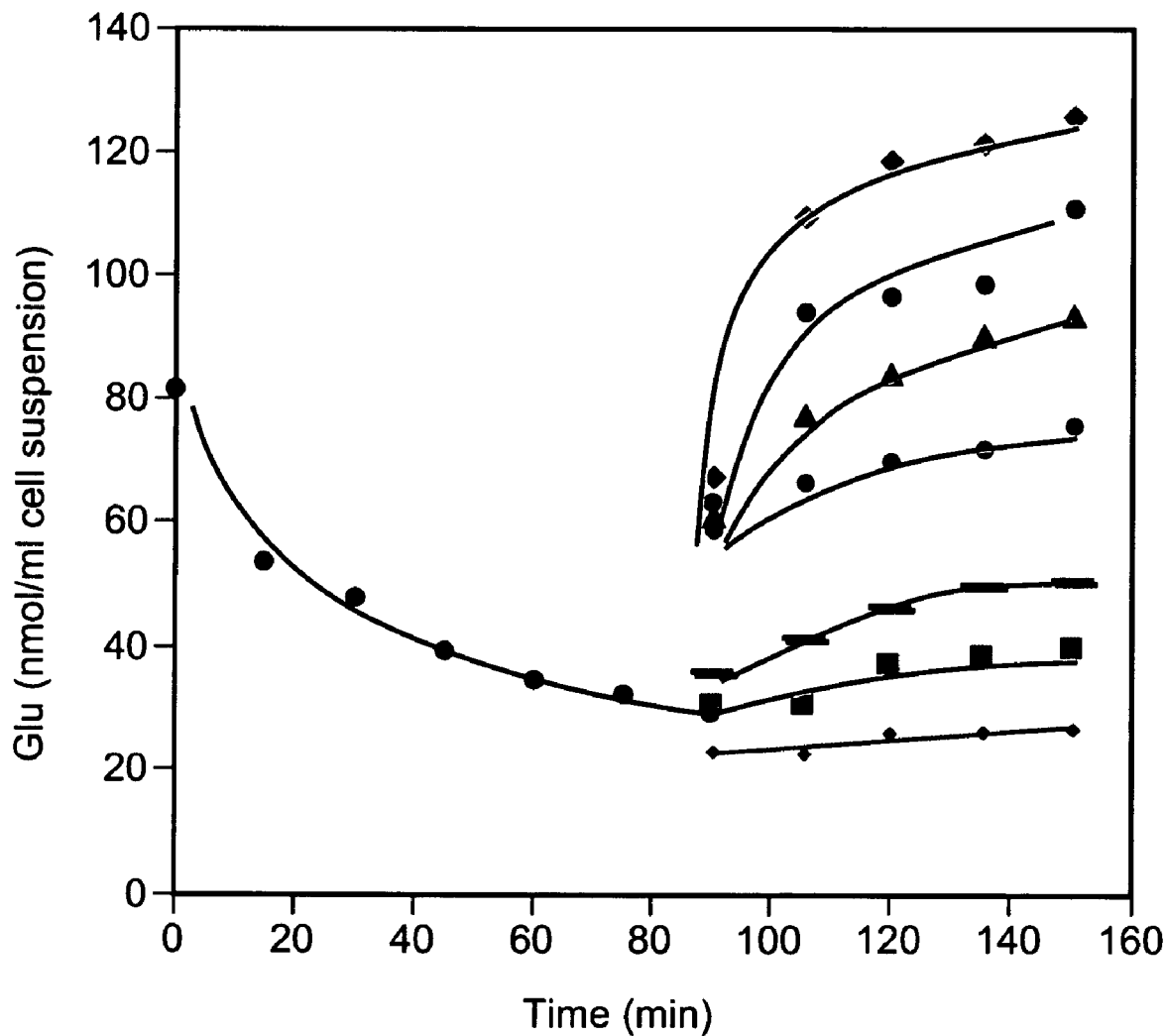
FIG. 11 illustrates glutamate uptake/adhesion to glutamate-depleted rat blood cells. Depicted are glutamate levels in the rat blood cell compartment, in-vitro, upon additions of pyruvate and oxaloacetate to a final concentration of 1 mM repeated every fifteen minutes for a total duration of 90 minutes (black circles). Cells were then washed and resuspended in Ringer Hepes buffer containing glutamate at various concentrations. The incorporation of glutamate in the blood cell compartment was monitored every fifteen minutes for a total duration of 60 minutes (from 90-150 minutes). Symbols are: blue filled diamonds: Ringer Hepes buffer; pink squares: 0.1 mM glutamate; black crosses: 0.2 mM glutamate; red circles: 0.4 mM glutamate; blue triangles: 0.6 mM glutamate; maroon diamonds: 0.8 mM glutamate; lavender diamonds: 1 mM glutamate. Each point represents the average of at least two glutamate determinations. One can observe two phases of glutamate uptake/adhesion to glutamate-depleted rat blood cells: an instantaneous phase and a slow developing phase.

Results—To verify this hypothesis, pyruvate/oxaloacetate were added in vitro, every fifteen minutes Over the course of 90 minutes, and glutamate levels in the blood cell compartment were ascertained, via methodology described in Example 1. Blood cell compartment glutamate depletion is evident throughout the 90 minute period (FIG. 11). The subsequent addition of glutamate concentrations ranging from 0.1 to 1 mM (monitored every fifteen minutes) over the course of 60 minutes results in a specific glutamate level increase in the blood cell compartment. This increase in glutamate occurs in two phases: one which is essentially instantaneous, and the other that ultimately saturates with time.

Erythrocytes appear to be the cellular constituent essential for glutamate mediated effects, since purified neutrophils, lymphocytes or platelets did not reveal any signs of glutamate uptake (data not shown).

Plotting the "instantaneous" cell glutamate increase as a function of glutamate concentration (FIG. 12) indicates that this process has an apparent Michaelian behavior, hence the saturation results. Analysis of the curve provides an apparent Km of 488±172 μM and a Bmax of 70±11 nmol glutamate/ml of cell suspension.

Figure 13:
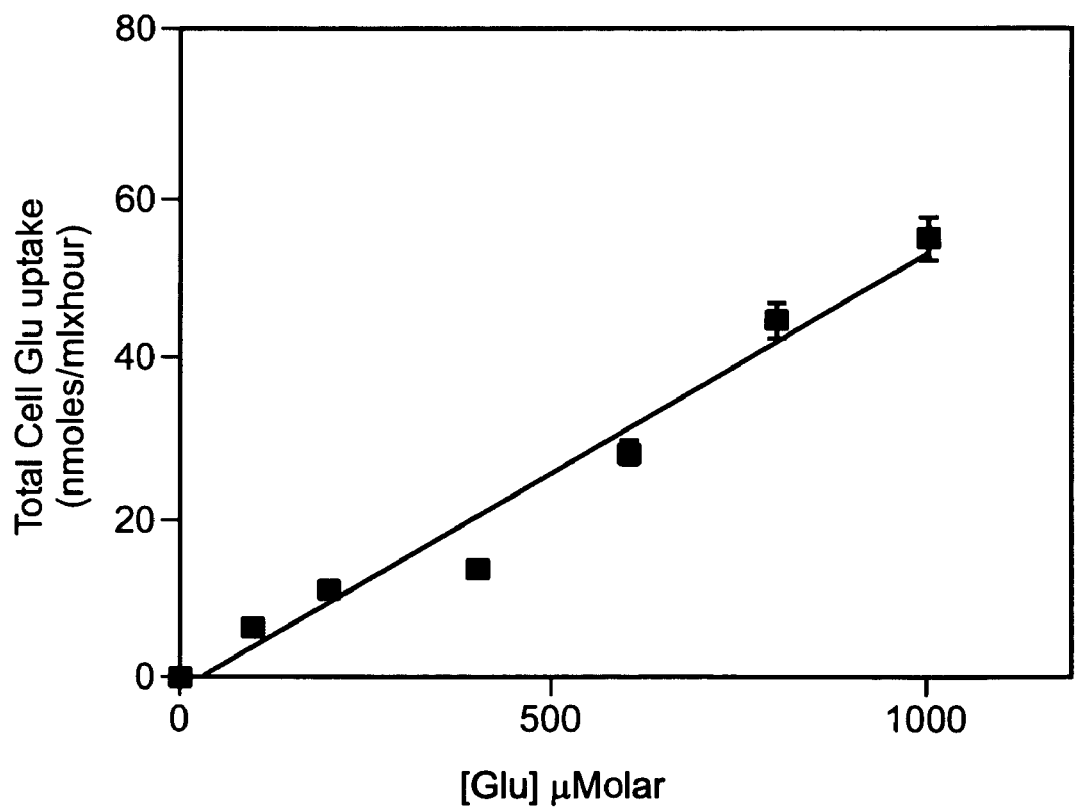
FIG. 13 shows the concentration dependence of the "slow" glutamate uptake/adhesion process to glutamate-depleted rat blood cells. Data was derived from FIG. 11. The process is linear and displays a correlation coefficient $R^2$=0.97.

Plotting of the total cellular compartment glutamate increase for the 60 minute course as a function of glutamate concentration, indicates a linear relationship between increasing glutamate concentrations versus time, reflective of the existence of a "slow" uptake process (FIG. 13). Lack of a saturation point when data is thus obtained may reflect the presence of a diffusive process.

Figure 12:
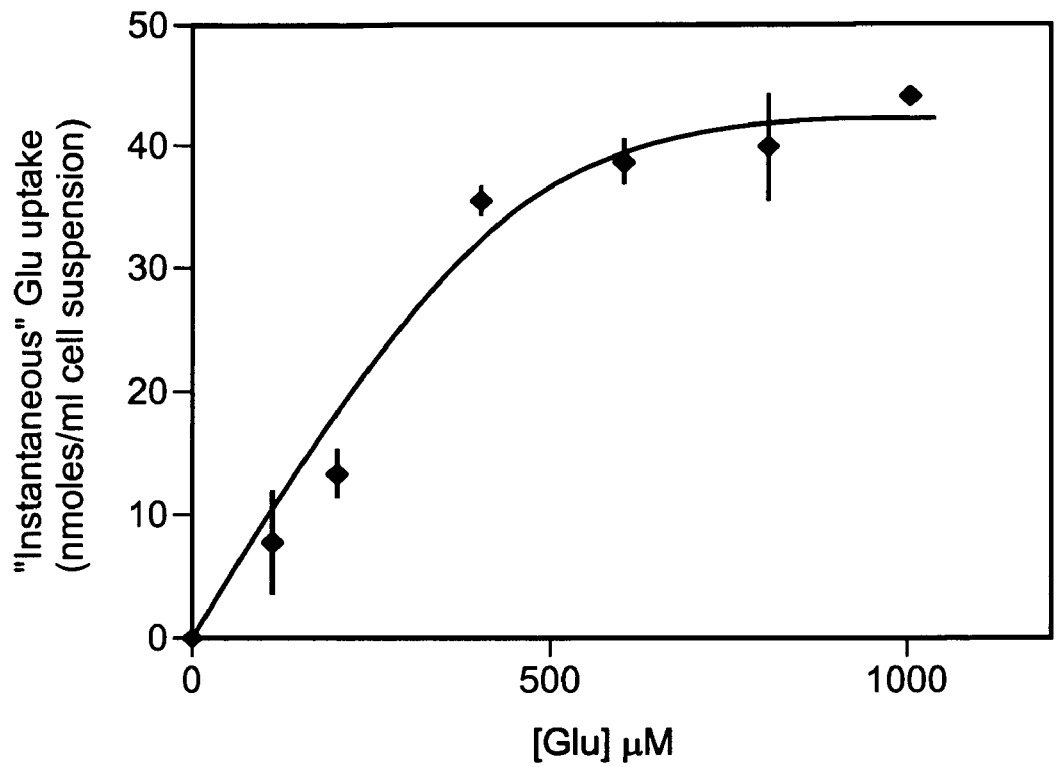
FIG. 12 illustrates the concentration dependence of the "instantaneous" glutamate uptake/adhesion to glutamate-depleted rat blood cells. Data was derived from FIG. 11. The process displays a Michaelian behavior with a Km=488±172 µM and a Bmax=70±11 nmol glutamate/ml of cell suspension.

As per the curves presented in FIGS. 12 and 13, for glutamate concentrations below 600 μM the capacity of the "instantaneous" process is about 2.4 times greater than the slow uptake process. Thus, the saturating "instantaneous" uptake process and the linear "slow" uptake process differ in terms of their glutamate uptake capacities, suggesting the existence of separate compartments for these processes.

Example 12

"Instantaneous" and "Slow" Increases in Blood Cell Glutamate Concentration

To further examine the nature of the "instantaneous" and "slow" increases in blood cell glutamate concentration (described in Example 10), blood cell compartment glutamate levels were assessed following an initial supply of glutamate in vitro, followed by exposure to glutamate free medium.

Figure 14:
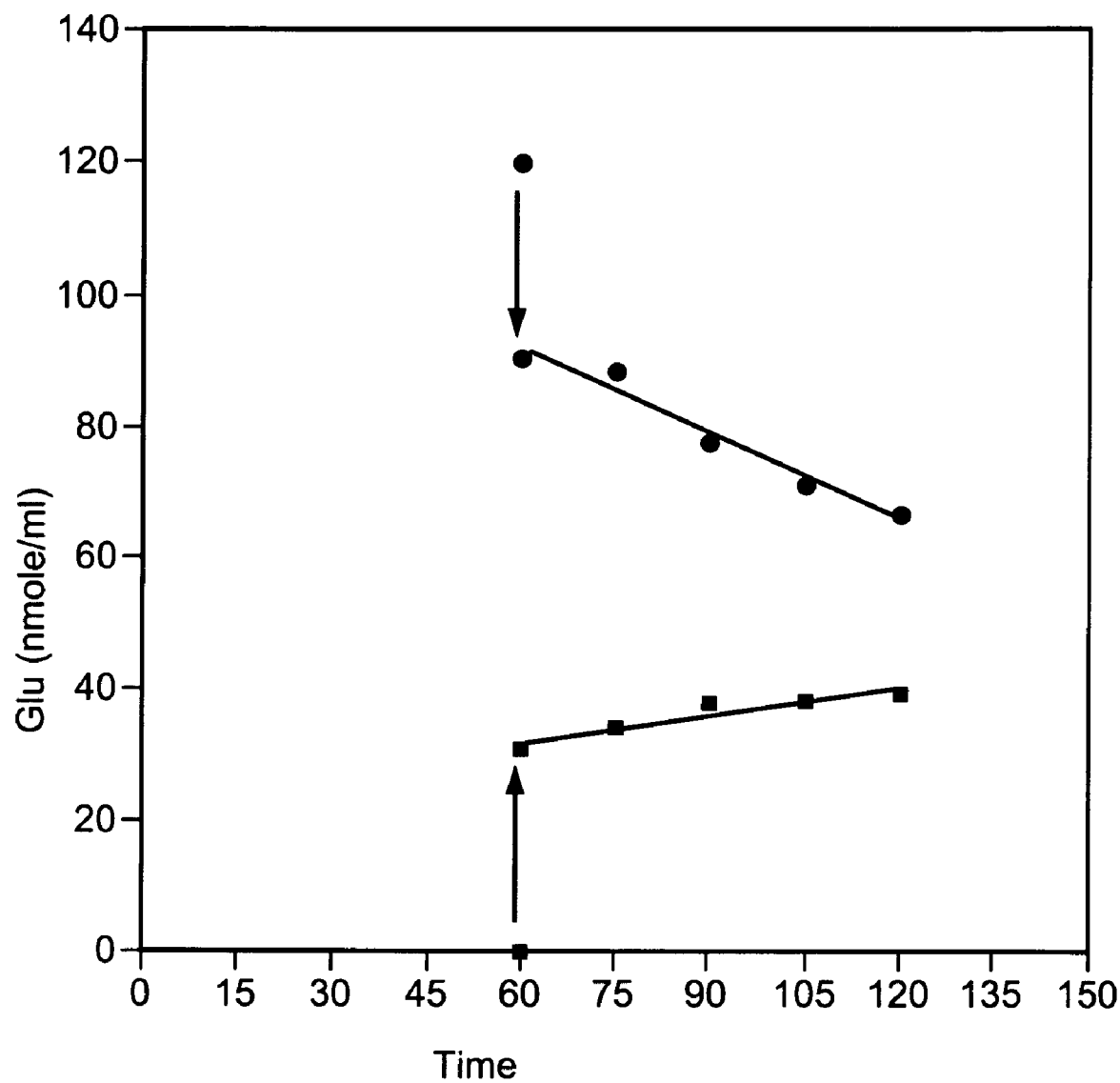
FIG. 14 displays the kinetics of glutamate release from glutamate-depleted rat blood cells loaded with 1 mM glutamate and placed in Ringer Hepes solution devoid of glutamate. Filled circles: progression of glutamate levels in the blood cell fraction. Filled squares: progression of glutamate levels in the extracellular solution. Arrows indicate the extent of the "instantaneous" glutamate release (downward arrows) from cells and of the "instantaneous" glutamate appearance in extracellular solution (upward arrows). Each point represents the average of at least two glutamate determinations.

Results—Blood cells were incubated for 60 minutes in 1 mM glutamate (as described in Example 10, hereinabove) and then were subsequently exposed to a glutamate free solution, whereupon cell and supernatant aliquots were assayed for glutamate concentration as a function of time. As can be seen in FIG. 14, the two populations are inversely related by exposure to glutamate-free conditions. Glutamate levels in the blood cell fraction decrease with time, while concurrently increasing in supernatants, though the decrease in glutamate from cells is more precipitous than its increase in supernatants, and therefore does not represent a mere diffusion effect, but in fact, is more likely a reflection of intracellular glutamate utilization.

In support of this interpretation, results from experiments carried out as above at 37° C. and at 20° C., revealed that the decrease in cell-associated glutamate was three times greater at 37° C. The higher temperature facilitates proper functioning of cellular pathways, and is therefore consistent with metabolic utilization of intracellular glutamate (data not shown).

Example 13

Cellular Uptake of Glutamate from Plasma In Vitro

Glutamate levels determined as above following depletion, in a glutamate free environment, measured "rebound" ability, the ability to adjust blood compartment glutamate levels. It was therefore of interest to determine the dynamics of glutamate concentrations in different blood compartments, as a result of subsequent exposure to glutamate levels in plasma.

Figure 15:
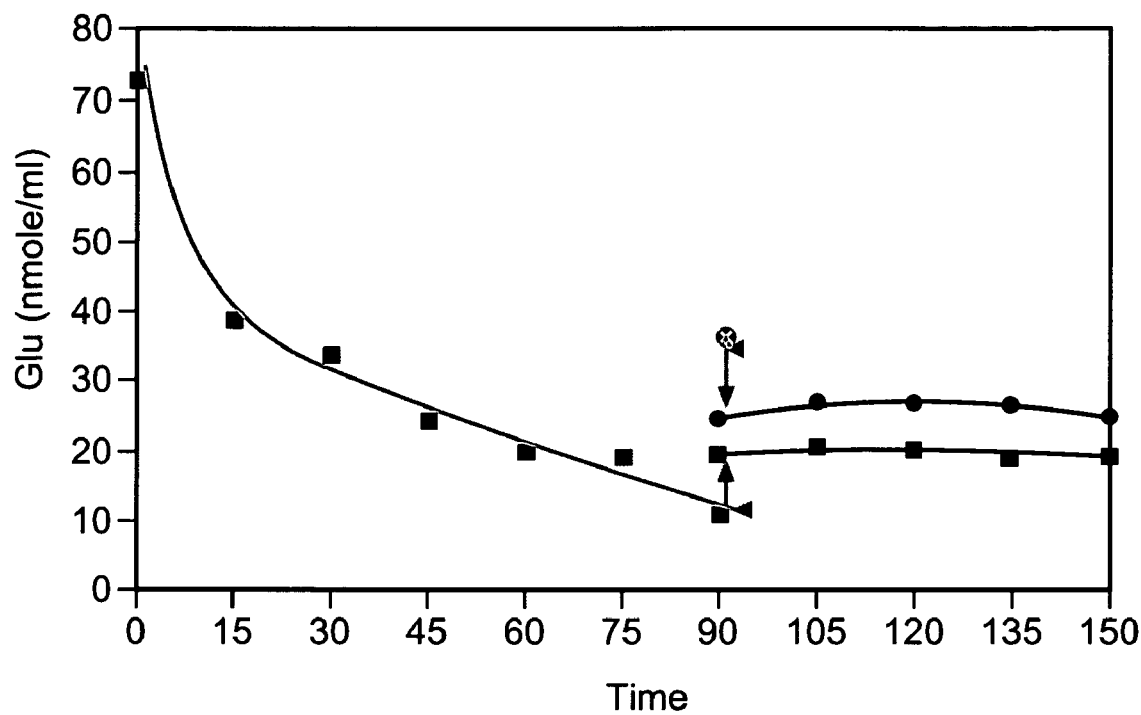
FIG. 15 illustrates plasma glutamate uptake/adhesion to glutamate-depleted rat blood cells. Progression of glutamate levels in the rat blood cell compartment in-vitro upon additions of pyruvate and oxaloacetate to a final concentration of 1 mM repeated every fifteen minutes for a total duration of 90 minutes (filled squares). Cells were then washed and resuspended in plasma. The levels of glutamate in the blood cell fraction (black squares) and plasma (black circles) were monitored every fifteen minutes for a total duration of 60 additional minutes. Each point represents the average of at least two glutamate determinations.

Results—These experiments determining glutamate concentration dynamics in differential blood compartments were conducted in vitro, and results are presented in FIG. 15. Glutamate-depleted blood cells respond with a roughly 30% instantaneous decrease in plasma glutamate levels, and a parallel glutamate blood cell level increase, sustained for 60 minutes. The "slow developing" glutamate uptake response in similarly treated cells is reduced when cells are exposed to plasma, consistent with the Km value estimated in FIG. 12. Thus glutamate levels in blood cells are somewhat restored by exposure to plasma, in contrast to a glutamate-free environment, where glutamate levels decline.

Example 14

Cellular Uptake of Glutamate from Plasma In Vivo

Materials and Experimental Methods
Animals—SPD rats weighing between 250-300 grams were used.
Donor blood processing—Donor rats were anaesthetized with 60 mg/kg Pentobarbital, and blood was withdrawn by surgical exposure of the chest cavity, followed by intracardiac collection into heparinized (0.8 mg/ml) tubes. Collected blood was then incubated at 37° C. with oxaloacetate and Pyruvate added every 10 minutes for a final concentration 1 mM, over the course of 40 minutes. Blood was then centrifuged at 4000 rpm for 10 minutes and the plasma withdrawn. The pellet was resuspended to the original blood volume into a 6% solution of hetastarch in 0.9% NaCl.

Blood exchange—Recipient rats were anaesthetized as above and transfusions were performed by placing a polyethylene cannula (PE 10) in the femoral vein for blood infusion and a polyethylene cannula (PE 10) in the femoral artery for blood withdrawal. Blood was transfused in at a rate 0.75 ml/min using a peristaltic pump while arterial blood was withdrawn at the same rate of 0.75 ml/min with the aid of an additional peristaltic pump.

Monitoring glutamate levels—Donor glutamate levels were monitored subsequent to blood withdrawal during in vitro incubation with oxaloacetate and pyruvate. Recipient glutamate levels were monitored via removal of 200 µl aliquots of blood from the femoral vein or the femoral artery. Aliquots were drawn twice prior to blood exchange, immediately following exchange, and 15, 30, 60 and 90 minutes post-exchange. The total blood exchange times' varied between 12-17 minutes.

Isovolemic haemodilution—Over the course 25 minutes each ml of blood removed was replaced by an equivalent volume of 6% Hetastarch. Glutamate levels in recipient rats were monitored in 100 µl aliquot's from each ml of blood removed. The remaining 900 µl were centrifuged at 4000 rpm for 10 minutes and the respective volumes of pellet and supernatant were measured and their ratio was defined as the haematocrit.

Figure 16:
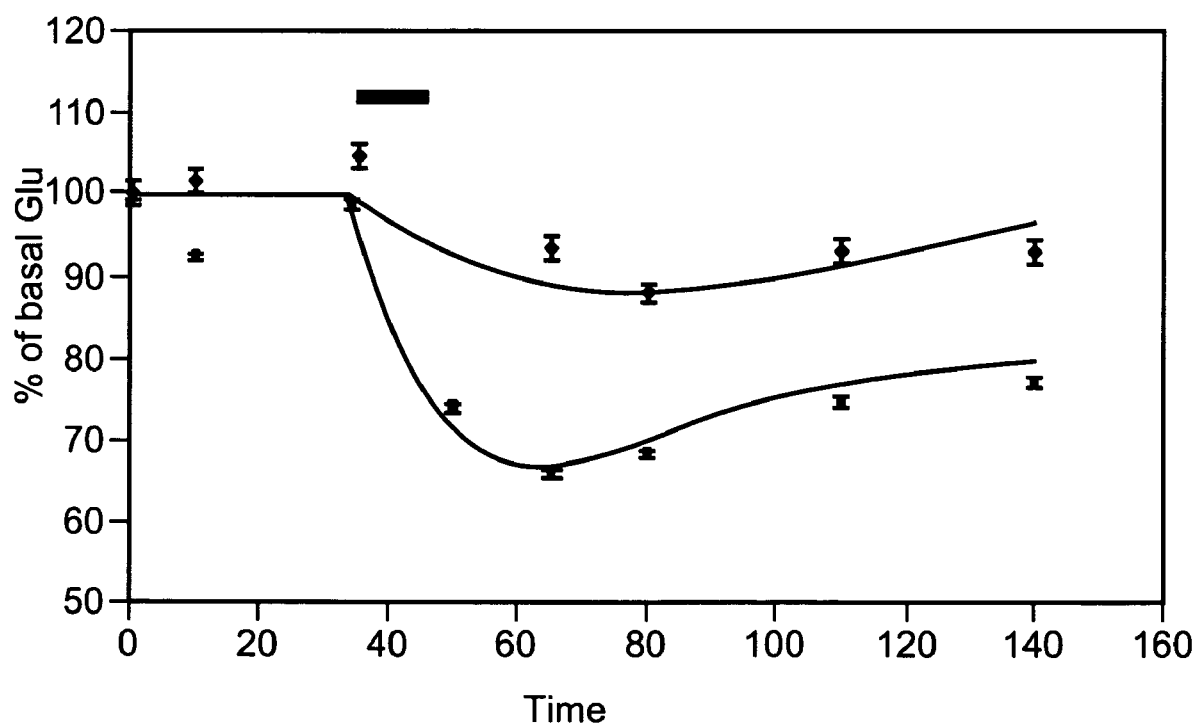
FIG. 16 illustrates progression of blood glutamate levels, in-vivo, following blood exchange. Blood (8.5 ml) was removed from a recipient rat and exchanged over 13 minutes (black bar) with 8.5 ml of glutamate-depleted blood cells suspended in 6% Hetastarch. Depletion of glutamate in the rat blood donor was achieved by incubation in-vitro with pyruvate and oxaloacetate at a final concentration of 1 mM added every fifteen minutes for a total duration of 60 minutes. The amount of blood exchanged corresponds to 40% of the total host blood volume. The levels of glutamate in the blood cell fraction (diamonds) and plasma fraction (squares) are presented. Symbols show averages of two glutamate determinations. One representative experiment out of 3 performed is shown.

Experimental Results—Because glutamate was found to be taken up from plasma specifically by glutamate depleted blood cells in vitro, and hence presents a feasible strategy for reducing plasma glutamate levels, it was important to evaluate this occurrence in vivo. Therefore, blood exchange experiments were conducted, in which blood was removed from a recipient rat and an equal volume of donor glutamate-depleted blood cells suspended in 6% Hetastarch (FIG. 16) was administered. Donor blood cell suspensions harboring 30% of the original glutamate levels and corresponding to 40% of the total host blood volume was exchanged (in an equivalent blood volume) for recipient blood, whereupon recipient glutamate levels both in the plasma and cell compartments of the recipient were monitored. Soon after termination of blood exchange, plasma glutamate concentration decreased. The decrease in glutamate plasma concentration can be attributed to "instantaneous" glutamate binding to red blood cells, and to dilution of the plasma itself, as a consequence of exchange with Hetastarch solution.

Thus diminished plasma glutamate levels recovered with slow kinetics, similar to that observed following pyruvate and oxaloacetate intravenous administration. The slow recovery is most likely a function of increased glutamate efflux from peripheral organs to blood, in response to decreased plasma glutamate concentration as a result of blood exchange or hemodilution.

Example 15

Effects of Haemodilution on Glutamate Levels

The preceding example revealed a change in glutamate concentrations in host cell compartments of up to 20%, as opposed to a 35% change in levels in plasma. It was hypothesized that glutamate concentration reduction was a result of rapid plasma glutamate binding to donor blood cells, as well as plasma glutamate dilution with the Hetastarch vehicle.

Figure 17:
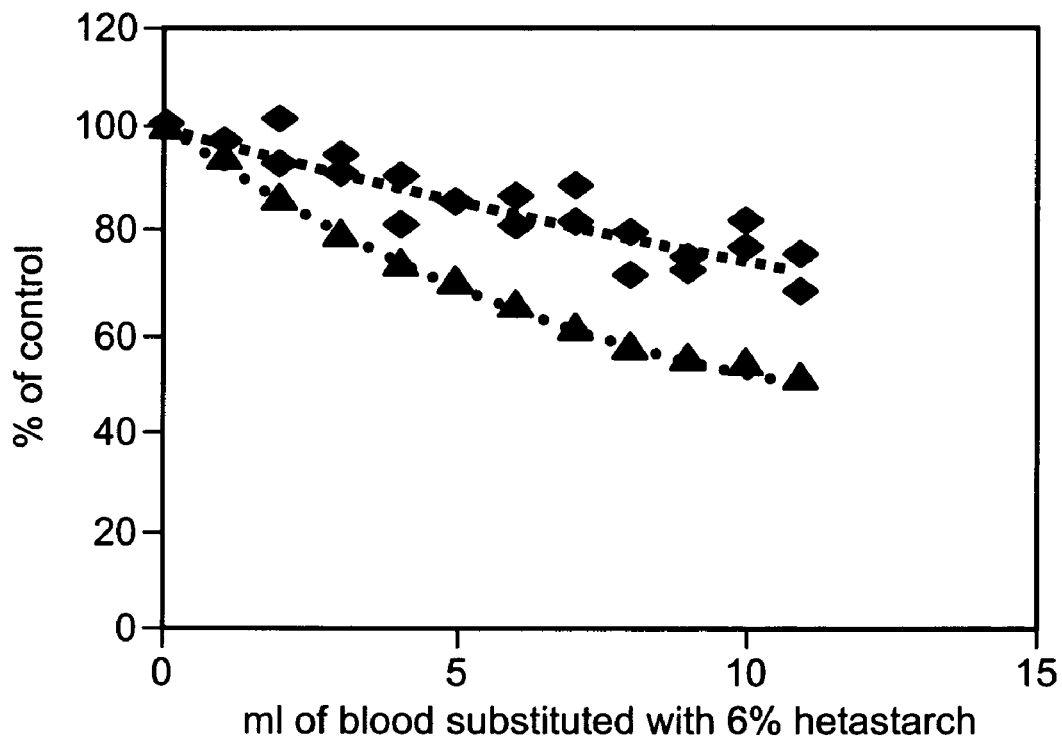
FIG. 17 depicts progression of blood glutamate levels in-vivo following an isovolemic hemodilution with 6% hetastatch. Blood aliquots of 1 ml were removed every 3 minutes from a recipient rat and exchanged with a 6% Hetastarch solution in PBS. Depletion of blood glutamate (diamonds) and the hematocrit (triangles) were monitored in each aliquot. One representative experiment out of 3 performed is shown.

Results—In order to confirm this hypothesis, recipient hematocrit levels, which represent the ratio of cell volume versus plasma volume, hence a function of plasma dilution, was assessed (FIG. 17). Blood glutamate concentration in rats subjected to isovolemic haemodilution, wherein each unit of blood removed is replaced with an equivalent volume of 6% Hetastarch, was conducted as well (FIG. 17). Interestingly, the change in hematocrit levels is much more pronounced than changes in absolute glutamate concentration in blood, suggestive of better compensatory mechanisms for increased glutamate efflux to blood from various organs, compensating for blood glutamate dilution.

Example 16

Efflux of Glutamate from Brain ISF/CSF to Blood

Materials and Experimental Methods

Materials—Glutamate, sodium pyruvate, sodium oxaloacetate, NADH, lactate dehydrogenase and malate dehydrogenase were purchased from Sigma (Sigma-Aldrich Corp., St Louis, Mo., USA). Glutamate dehydrogenase was purchased from Boehringer Mannheim (Roche diagnostics GmBH Mannheim, Germany). [$^3$H]Glu (42 Ci/mmole) was purchased from Amersham (Amersham Biosciences Inc, Piscataway, N.J., USA).

Intracerebroventricular injections—Sprague-Dawley rats (250-300 g) were anaesthetized via intraperitoneal urethane injection (0.125 grams/0.2 ml per 100 grams body weight). Catheterization of the tail vein (for drug injections) and of the femoral vein (for blood aliquot withdrawals) was performed using PE10 polyethylene tubing linked to PE50 polyethylene tubing. All catheters were secured with 5-0 silk thread and flushed with heparin (3-5 µl of 182 U/ml). A 27G steel cannula was implanted in the right lateral ventricle using the following stereotactic coordinates: 0.8 mm posterior to bregma; lateral 1.4 mm; depth: 4 mm from skull or 3.5 mm from dura. A [$^3$H] glutamate solution in phosphate buffered saline (PBS) was injected into the lateral ventricle through the implanted cannula using a Hamilton syringe (25 µl) connected to PE20 tube filled with solution. A total volume of 11 µl was injected within approximately 2 minutes.

For radioactivity determination, 50 µl blood samples were diluted in 500 µl H$_2$O and added to 16 ml of scintillation fluid. Measured cpms were corrected for quenching as determined by comparing the measured cpms of a set volume of [$^3$H] glutamate added to water or to diluted blood. Body temperature was maintained with a lamp and rectal temperature was monitored. Rat pulse rate was monitored using a Periflux system 500 and a laser Doppler probe placed onto the skull.

Intravenous injections of pyruvate and oxaloacetate diluted in phosphate buffered saline (PBS) were carried out at a rate of 0.05 ml/minute for 30 minutes with a Pharmacia pump P-1. During injections and at several time points after the injections (typically every 15 minutes), aliquots of 150 µl blood were removed from the femoral vein.

Measurement of glutamate concentration—Aliquots of 1 µl were removed at each time point and centrifuged at 1,300×g for 7 minutes. The volume of supernatant (plasma) was measured and an identical volume of 1M PCA (perchloric acid) was added to precipitate proteins. The mixture was left for 10 minutes on ice and centrifuged. The cell pellet (erythrocytes, lymphocytes, platelets) was lysed by osmotic shock upon resuspension in double distilled water up to a final volume of 150 µl and an identical volume of 1M PCA was added. Both plasma and cell PCA-precipitated fractions were centrifuged at 16,000×g for 10 min and the pellet was discarded.

Glutamate concentration was measured in the supernatant using the fluorometric method of Graham and Aprison (1966). A 20 µl aliquot from PCA supernatant was added to 480 µl HG buffer containing 15 U of glutamate dehydrogenase in 0.2 mM NAD, 0.3 M glycine, 2.4% hydrazine hydrate adjusted to pH 8.6 with 1N H$_2$SO$_4$. After incubation for 30-45 minutes at room temperature, the fluorescence was measured at 460 nm after excitation at 350 nm. A glutamate standard curve was established with concentrations ranging from 0-6 [M. All determinations were done in duplicates.

Results—In previous examples, intravenous pyruvate and oxaloacetate administration reduced recipient blood glutamate levels, yet these levels ultimately increased. It was hypothesized, as a result, that peripheral organs provide a source for glutamate efflux, enabling normalization of circulating glutamate concentrations. In order to test this hypothesis, glutamate efflux from brain interstitial fluid (ISF) or cererbrospinal fluid (CSF) to blood, following intravenous administration of pyruvate and oxaloacetate, was investigated.

In order to monitor the effects of reducing plasma glutamate on the levels of brain glutamate, one experimental system employed the use of radiolabelled glutamate injected into a lateral ventricle and the appearance of radioactivity in blood was monitored as a function of time, in animals subjected to depletion of circulating glutamate levels by oxaloacetate/pyruvate administration. Subsequent appearance of blood-associated radioactivity is hence a function of brain glutamate efflux.

Figure 18:
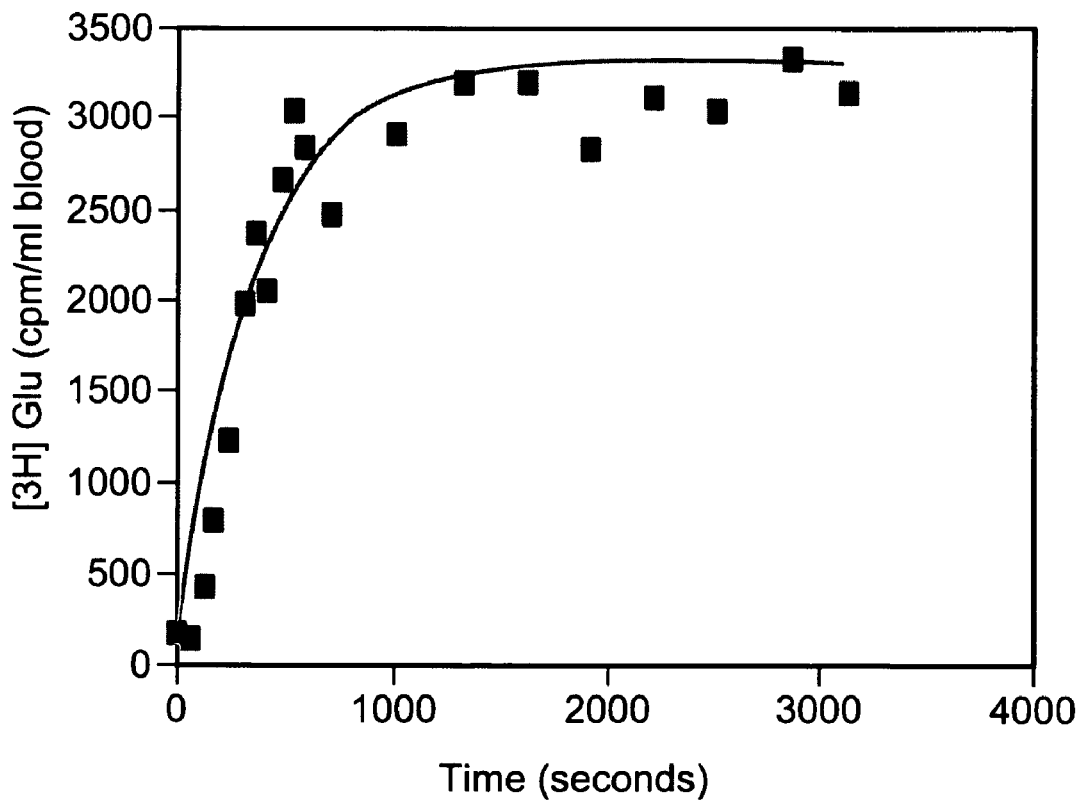
FIG. 18 illustrates changes in blood radio-labeled glutamate levels following the intracerebroventricular infusion of 11 µCi in 11 µL of [$^3$H]glutamate ([$^3$H]Glu). One representative experiment out of 8 performed is shown.

The amount of radio-labeled glutamate in the blood following intracerebroventricular injection is depicted in FIG. 18. Radio-labeled glutamate efflux into peripheral circulation is a function of time, and occurs primarily in two phases. In the first phase, the distribution phase, the radioactivity appears in the blood as soon as [$^3$H] glutamate is injected in the lateral ventricle and increases linearly up to 10 minutes, at a rate of 0.8%±0.1 (n=8) of the amount of radioactivity input in the brain per minute. This corresponds to a half-life of elimination of radioactivity from brain of 62.5±7 min. In the second phase, blood radioactivity remains constant for at least 40 minutes, likely as a function of an achieved steady state between the rate of [$^3$H] glutamate efflux from the brain to the blood and the rate of disappearance of [3H] glutamate from the blood.

Thus, following peripheral glutamate depletion by the administration of oxaloacetate/pyruvate, peripheral glutamate level normalization occurs via glutamate efflux from other organs, including the brain, as evidenced in this example by the presence of circulating radioactively labeled glutamate, previously restricted to the brain.

Example 17

Measurement of Glutamate Life Time in Blood

Assessing peripheral glutamate normalization following oxaloacetate/pyruvate administration is another means of determining factors involved in glutamate efflux from peripheral organs as a means of normalizing circulating glutamate concentration. Methods for establishing the rate of normalization may therefore provide clinical application when considering a course of therapy utilizing the protocol suggested herein.

Figure 19:
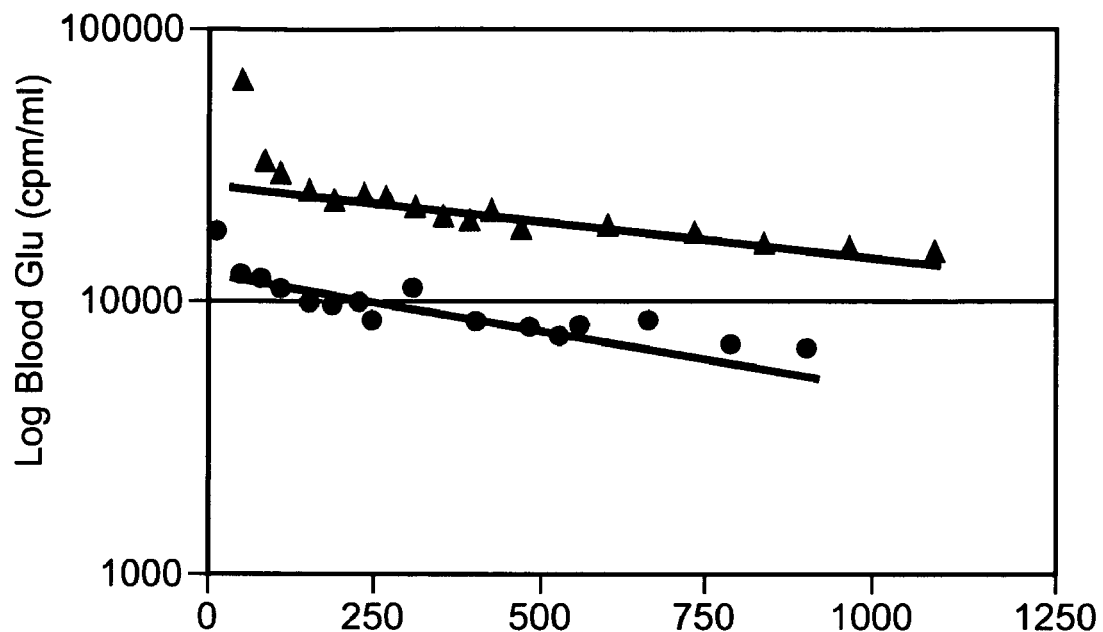
FIG. 19 shows changes in blood radio-labeled glutamate levels following the bolus intravenous injections of 1 µCi [$^{14}$C] glutamate in the absence (blue circles) or presence (red triangles) of 3.4 mM unlabeled glutamate. One representative experiment out of 3 performed is shown.

Results—Glutamate normalization may be accomplished by estimating the rate of disappearance of [$^{14}$C] glutamate from the blood, by methodology detailed in the preceding example. Administration of a bolus intravenous injections of 11 μCi radio-labeled glutamate in the absence or presence of non-radioactive glutamate was conducted and the presence of radioactivity in blood was monitored over time (FIG. 19).

The kinetics obtained for the appearance of [$^3$H] glutamate radioactivity levels in blood takes place in two phases: a fast phase terminating within less than 60 seconds and which corresponds most likely to the distribution phase and a slow one that corresponds to the elimination phase. Accordingly, one can calculate the elimination half-life of [$^3$H] glutamate in blood as being 19.3 minutes (and an elimination rate constant equal to ln2/19.3=0.035 min$^{-1}$) for a normal blood glutamate concentration of 209 μM. 30 (SD; n=34), and thus that 5.4 nmoles of glutamate/ml blood are eliminated per minute. The elimination half-life increased to 24.6 minutes when blood glutamate reached a concentration of 3.4 mM by intraperitoneal administration of 2 mMoles of glutamate. Under these conditions, 69 nmoles glutamate/ml blood were eliminated per minute.

Thus, the rate of glutamate elimination from blood increases by about 13 fold for a 16 fold increase of blood glutamate concentration suggesting that the enzymes and transporters involved in glutamate elimination are not yet saturated at 3.4 mM. The fact that non-radioactive glutamate slows down the elimination half life of [3H] glutamate is suggestive that blood radioactivity corresponds mainly to non-degraded [$^3$H] glutamate and that glutamate and [$^3$H] glutamate compete for the same transport sites in organs that display an avid glutamate uptake from blood such as muscle, kidney, intestine and lung (Hediger and Welbourne, 1999). In line with the above, Hoyosa et al (1999) have indeed observed that L-glutamate in the brain interstitial fluid is transported across the blood brain barrier in an intact form.

Example 18

Brain to Blood Glutamate Efflux Following Treatment with Oxaloacetate and Pyruvate Another means of verifying the above hypothesis, that peripheral organs provide a source for glutamate efflux, enabling normalization of circulating glutamate concentrations, may be effected by direct measurement of an organ's potential for glutamate mobilization.

Results—In order to further corroborate the proposed hypothesis, monitoring intracerebroventricular injection of radio-labeled glutamate (11 μCi of [$^3$H]Glu) was performed and the percentage of glutamate absorption was measured, prior to and following intravenous administration of pyruvate and oxaloacetate.

Figure 20:
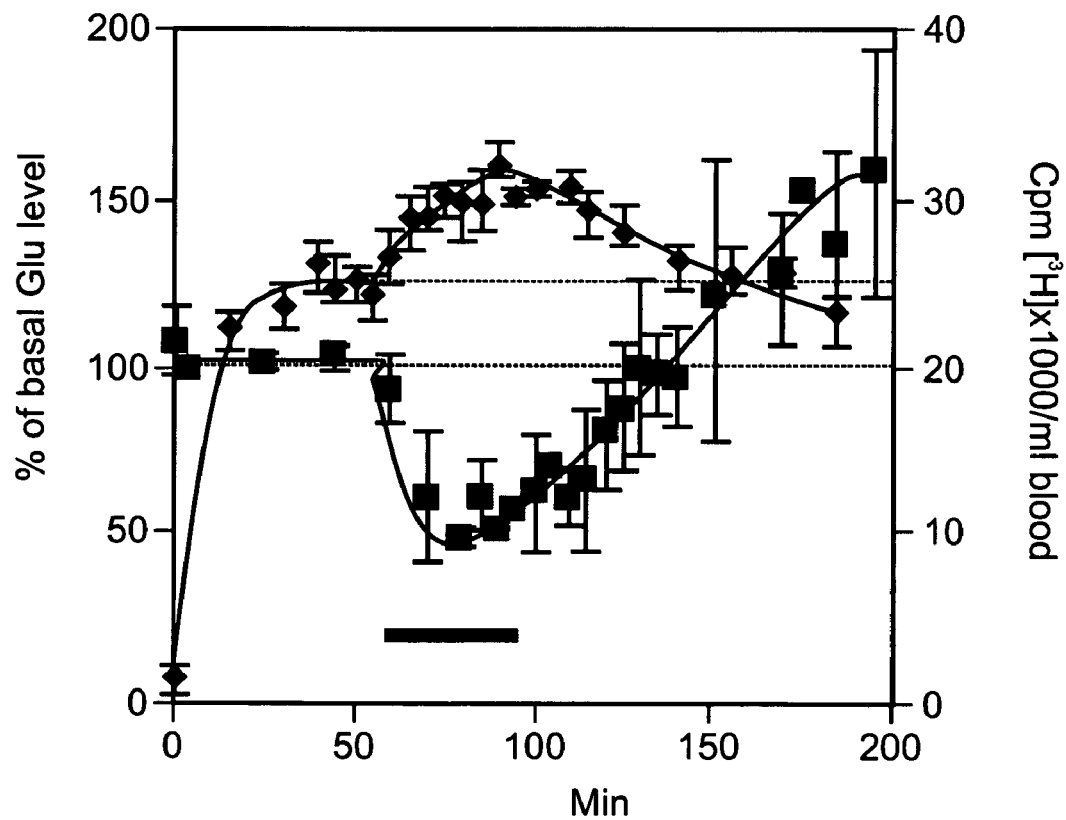
FIG. 20 illustrates the impact of blood glutamate scavenging on the brain-to-blood [$^3$H]Glu efflux by monitoring evolution of blood radioactivity (diamonds) and blood Glu levels (squares) following the intracerebroventricular infusion of 11 µCi of [$^3$H]Glu and its modulation by the intravenous administration of pyruvate and oxaloacetate. The injection of oxaloacetate was started 55 minutes following injection of pyruvate; both compounds were provided at a rate of 50 µMoles/min each for a duration of 30 min (black bar). This regimen causes the build up of a blood concentration of 0.45 mM for both pyruvate and oxaloacetate (see FIG. 8). Each point represents the average of three independent experiments± standard deviation (SD). An unpaired two-tailed Student's t test performed for the steady state [$^3$H]Glu levels reached before and during the infusion of pyruvate and oxaloacetate shows a p value of 0.002. The broken lines show the steady state levels reached before the intravenous administration of pyruvate and oxaloacetate.

As is shown in FIG. 20, changes of blood radioactivity originating from brain displays an almost mirror image to that of blood Glu. While the latter decreases by about 50% during the administration of pyruvate and oxaloacetate and then increases, the blood radioactivity increases by about 40% and then decreases.

It is apparent, therefore, that diminished levels of glutamate in the blood caused [$^3$H] glutamate efflux from brain to the blood as a means or achieving normalization of blood glutamate levels.

As a result of these studies, brain glutamate levels (a reflection of [$^3$H] glutamate concentration, determined from FIG. 19) can be plotted as a function of time (FIG. 21), and brain-specific glutamate efflux can be calculated, according to equation I:

$$C_t = C_0 - (R_t - R_{(t-Dt)}xe^{-K(t-Dt)}) \quad (I)$$

where $C_t$=amount of [$^3$H] glutamate remaining in the brain at time t; $C_0$=amount of t3H] glutamate in brain at time t=0; $R_t$=amount of [$^3$H] glutamate in blood at time t; $R_{(t-Dt)}$=amount of [$^3$H] glutamate remaining in blood from time t-Dt; K=elimination rate constant of [$^3$H] glutamate in blood (=ln2/elimination half life of [$^3$H] glutamate in blood); thus, $(R_t - R(t-Dt)xe-K(t-Dt))$=net release of [$^3$H] glutamate from the brain during the time interval of Dt.

Figure 21:
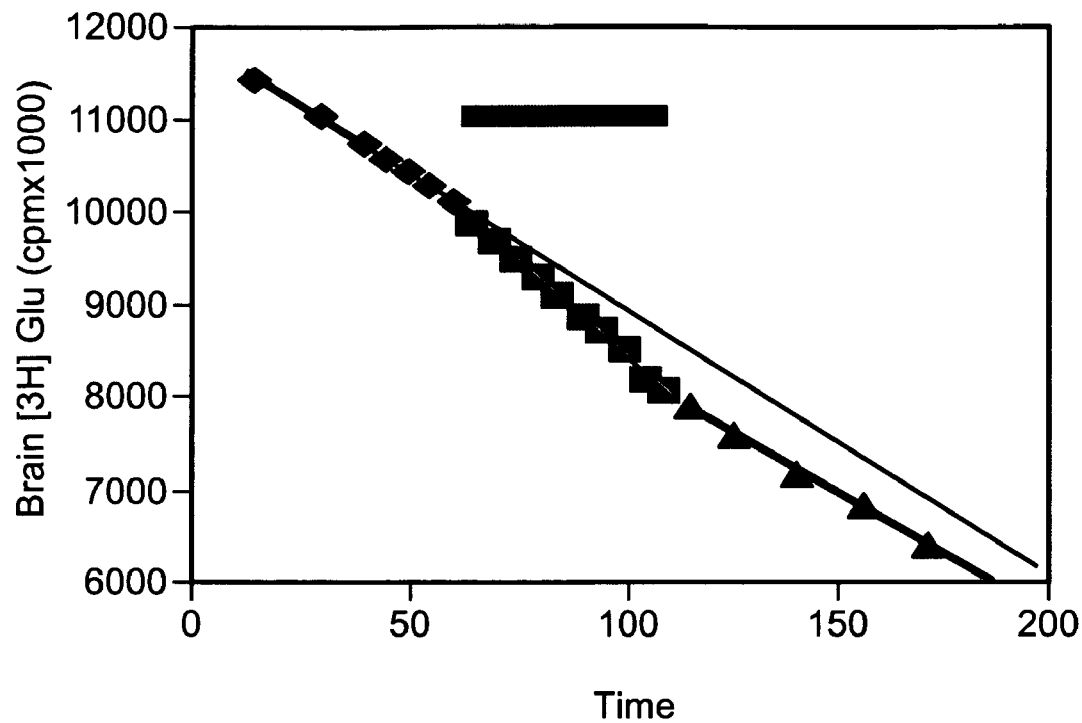
FIG. 21 illustrates the evolution with time of the [$^3$H] glutamate levels in brain following intracerebroventricular infusion. The parameter on the ordinate represents $C_t$ i.e. the amount of [$^3$H]glutamate remaining in brain at time t calculated according to the relation I on the basis of the data presented in FIG. 19. Green, $C_t$=153; Blue, $C_t$=201; Red, $C_t$=199.

It is apparent from FIG. 21 that following the first 10 minutes, the level of brain [$^3$H] glutamate decreases in three phases. Immediately prior to and following administration of pyruvate and oxaloacetate, the residence half-lives of [3H] glutamate in the brain correspond to 201 minutes and 199 minutes, respectively. During administration of the GPT/GOT substrates the residence half-life of [$^3$H] glutamate in the brain corresponds to 153 minutes. Thus, administration of the GPT/GOT substrates, causing a decrease in circulating glutamate levels, results in a decrease in [$^3$H] glutamate residence time in the brain, thus supportive of an accelerated brain to blood glutamate efflux.

Figure 22:
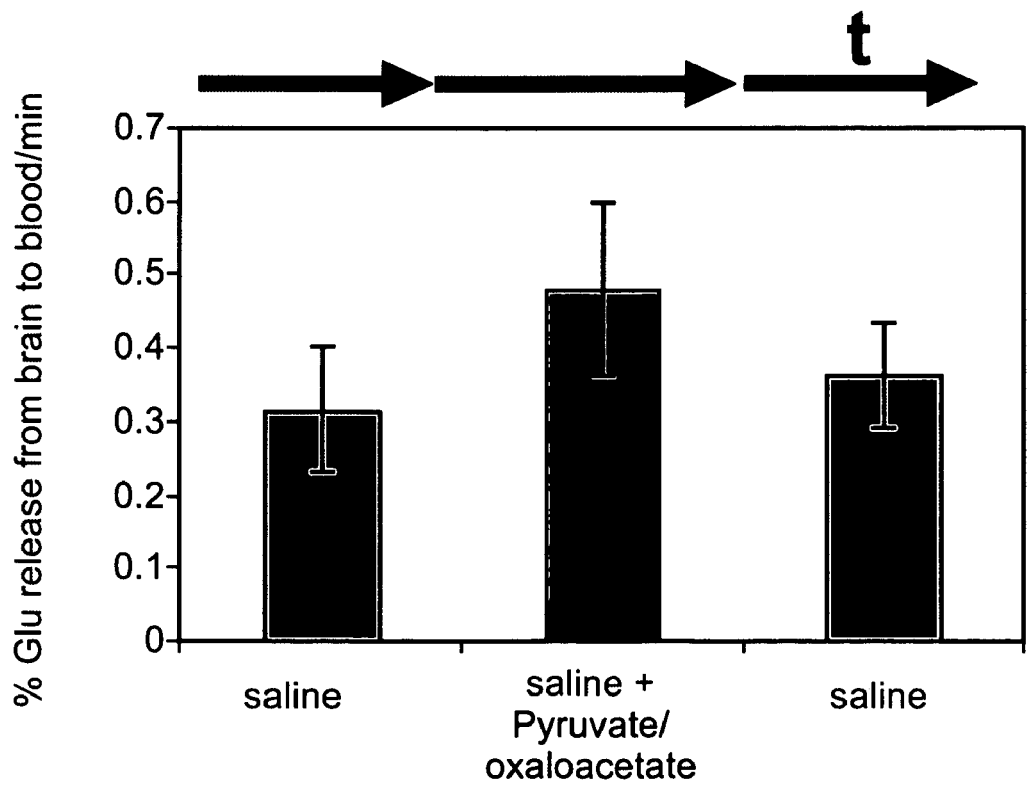
FIG. 22 is a histogram illustrating the percentage of glutamate released from brain to blood per min prior to (left column) concomitant with (middle column) and following (right column) intravenous administration of pyruvate and oxaloacetate. This analysis summarizes the results provided in FIGS. 20-21.
Figure 23:
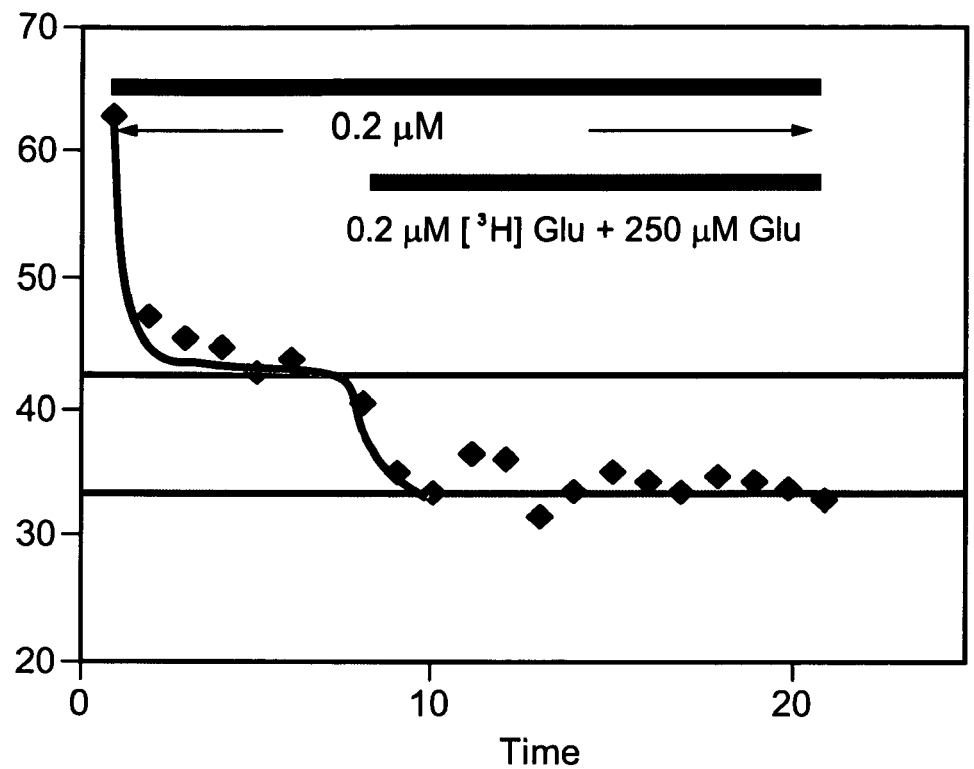
FIG. 23 depicts ventriculo-cisternal perfusion of [$^3$H] glutamate and the percentage of [$^3$H]glutamate absorbed. The latter was calculated as (1−R)×100 where R is the ratio of the radioactivity input per unit volume to that of the output collected at the cisterna magna. The perfusion was started with a 0.2 µM [$^3$H]glutamate solution in artificial CSF and switched after 8 minutes to one containing 0.2 µM [$^3$H]glutamate together with 250 µM of unlabeled glutamate. The flow rate was 26 µl/minute. One representative experiment out of 3 performed is shown.

An alternative means of assessing the efflux of glutamate from the brain to the blood is by calculating a fractional rate of [$^3$H] glutamate release (F) via equation $$F = (R_t - R_{(t-Dt)}xe^{-K(t-Dt)})/C_{(t-Dt)} \quad (II)$$

where $C_{(t-Dt)}$=amount of [$^3$H] glutamate remaining in the brain at time t-Dt This fractional rate, or F value, may be obtained prior to, during and following pyruvate and oxaloacetate administration (FIG. 22). Consistent with data obtained from efflux calculation, F values obtained indicated a markedly enhanced rate of glutamate release (50%) by the intravenous administration of pyruvate and oxaloacetate, which, upon its removal, indicates a rate returning to that prior to substrate administration. Rate increases are abolished when [$^3$H] glutamate is injected in a solution containing non-radioactive glutamate (5 mM), indicating that the brain to blood efflux of glutamate is saturable (data not shown).

Thus in addition to verification of glutamate efflux from the brain to peripheral circulation, in response to diminished plasma glutamate levels, a rate of efflux can be determined, for accurate assessment of glutamate efflux.

Example 19

Measuring Glutamate Efflux from Brain to Blood Via Perfusion Model

Materials and Experimental Methods

Ventriculo-cisternal perfusion—Perfusion was accomplished according to the procedure described by Davson et al (1982) J. Neurobiol. 13:293-318. Briefly, Cannulas (27G) were placed in the two lateral ventricles. Cannulas implanted in the lateral ventricles were connected to PE10 polyethylene tubing attached to 5 ml syringes driven by a Harvard apparatus infusion pump. The pump was set to release 26 μl/minute of [$^3$H] glutamate in artificial cererbro-spinal fluid (CSF) (122 mM NaCl, 25 mM NaHCO$_3$; 3 mM KCl; 1.4 mM CaCl$_2$; 1.2 mM MgCl$_2$ 0.4 mM K$_2$HPO$_4$; 10 mM HEPES, 10 mM glucose, pH 7.42). Each syringe contained 4 ml of artificial CSF, 0.2 μM [$^3$H] glutamate and, When needed various amounts of non-radioactive glutamate.

Results—Another means of verifying whether reducing blood glutamate levels effects changes in brain glutamate concentration is via experiments utilizing [$^3$H] glutamate ventriculo-cisternal perfusion for measuring radio-labeled glutamate elimination from perfused fluid. In this paradigm, a [$^3$H]Glu containing solution is continuously perfused through cannulas implanted in the lateral ventricles and is collected as it emerges from a cannula implanted in the cisterna magna. The ratio [R] of the radioactivity input per unit volume to that of the output, provides an index of the percentage of [$^3$H]Glu absorbed from the perfused fluid. The absorption is due to the diffusion of [$^3$H]Glu into the brain cerebrospinal and interstitial fluids and to its uptake into cellular compartments via the Glu transporters present on the choroid plexus epithelial cells and those associated with the antiluminal membranes of brain capillary endothelial cells.

Figure 24:
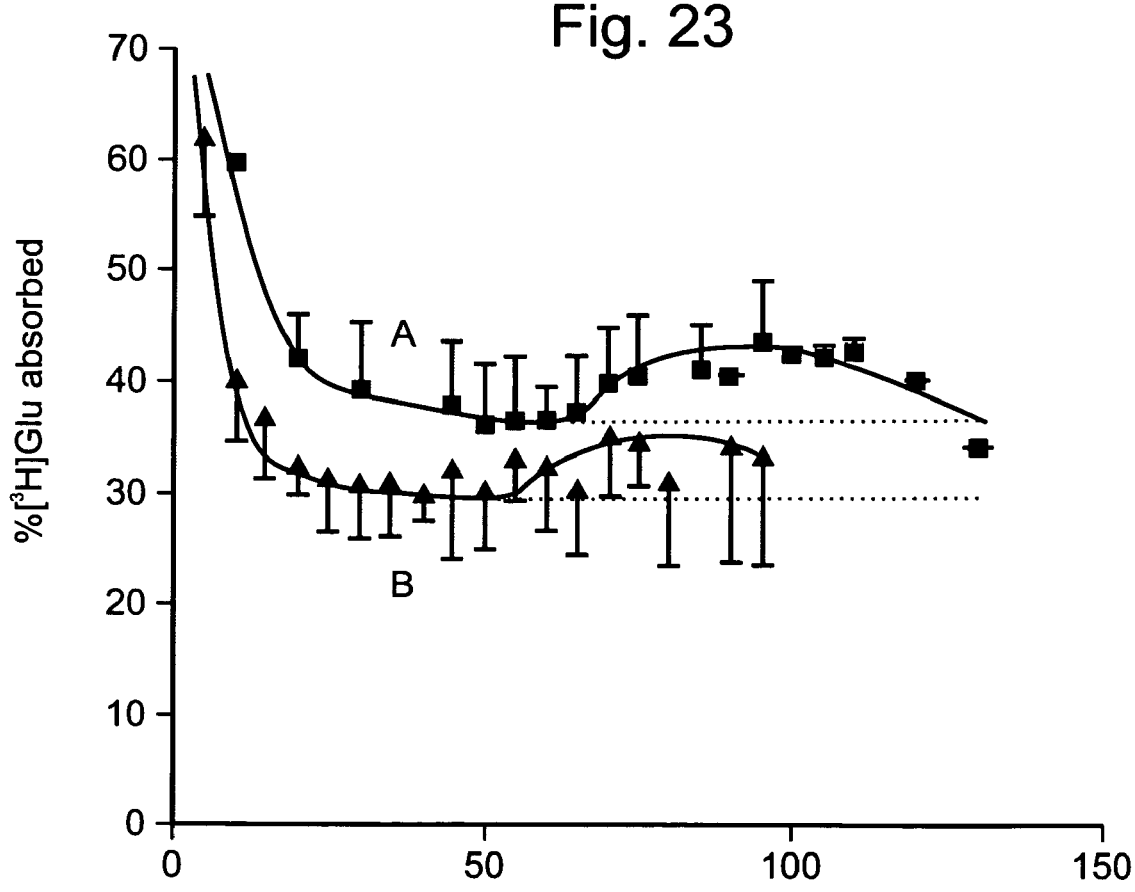
FIG. 24 illustrates the impact of blood glutamate scavenging on the brain [$^3$H]Glu absorption by performing ventriculo-cisternal perfusion of [$^3$H]Glu and monitoring the evolution of the percentage of [$^3$H]Glu absorbed. The percentage was calculated as (1−R)×100 where R is the ratio of the radioactivity input per unit volume to that of the output collected at the cisterna magna. Graph A—Perfusion of a 30 µM [$^3$H]Glu solution in artificial CSF containing 0.2 µCi [$^3$H]Glu/ml (squares). After 60 min, an intravenous infusion of pyruvate and oxaloacetate was started at a rate of 50 Moles/min for a duration of 50 min. A student t test performed for the steady state values reached before and during the infusion of pyruvate and oxaloacetate shows a p value of 0.008. Graph B—Perfusion of a 250 µM [$^3$H]Glu solution in artificial CSF containing 0.2 µCi [$^3$H]Glu/ml (triangles). The perfusion was carried out at a flow rate of 26 μl/min. After 55 min, an intravenous infusion of pyruvate and oxaloacetate was started at a rate of 50 μMoles/min for a duration of 50 min. Under these conditions an average of 50±10% reduction of blood Glu is achieved (FIG. 9). Each point represents the average of three independent experiments±standard deviation (SD). A Student's t test performed for the steady state values reached before and during the infusion of pyruvate and oxaloacetate shows a p value of 0.58. The broken lines show the steady state levels reached before the intravenous administration of pyruvate and oxaloacetate

FIG. 24 illustrates that ventriculo-cisternal perfusion of a 30 µM Glu solution containing 0.2 µCi [$^3$H]Glu/ml leads to a steady state absorption of about 36±5% which increases to 43.7±3% (p=0.035) upon the intravenous administration of pyruvate and oxaloacetate and decreases back towards the basal steady state absorption level upon completion of the infusion of pyruvate and oxaloacetate. Thus, the absorption of radioactive Glu from the perfusion fluid increases while the blood Glu levels decrease. When the perfusion is performed with a solution containing 250 µM Glu solution and 0.2 µCi [$^3$H]Glu µ/ml, the absorption of [$^3$H]Glu decreases to a steady state of 30.8±0.5% because of the competition for the brain absorption sites by unlabeled Glu. Upon intravenous injection of pyruvate and oxaloacetate, the absorption of radioactive Glu from the perfusion fluid slightly increases to an apparent steady state of 33.8±0.9% as some of the competing unlabeled Glu is pumped into blood thereby decreasing competition with [$^3$H]Glu for uptake by the various Glu transporters.

Though the extent of glutamate absorption from perfusion fluid by individual transporters is unknown, it is anticipated that transporter absorption would increase if brain-to-blood glutamate efflux were accelerated.

Thus, an additional means of assessing normalization responses to reduced circulating glutamate levels exists, that of measuring absorption of radio-labeled glutamate from perfused brain ventricles. A proposed mechanism whereby brain to blood efflux may be accomplished, via direct brain transporter uptake is supported by the present finding that in perfused brain, the addition of oxaloacetate/pyruvate stimulated an increase radio-labeled absorption from the perfusion fluid, as a means of mobilizing glutamate from the brain, ultimately to the peripheral circulation.

Example 20

Brain Glutamate Efflux from ISF/CSF to Blood and Potential Mechanism of Action

Materials and Experimental methods

CSF collection—Cannula (27G) were placed the cisterna magna connected to PE10 tubing with its outlet kept 17.5 cm below the aural line. Following lateral ventricle infusion, fluid emerging from the cisterna was collected as a function of time. Remaining methodologies is as described in Example 19, and previous Examples.

Figure 25:
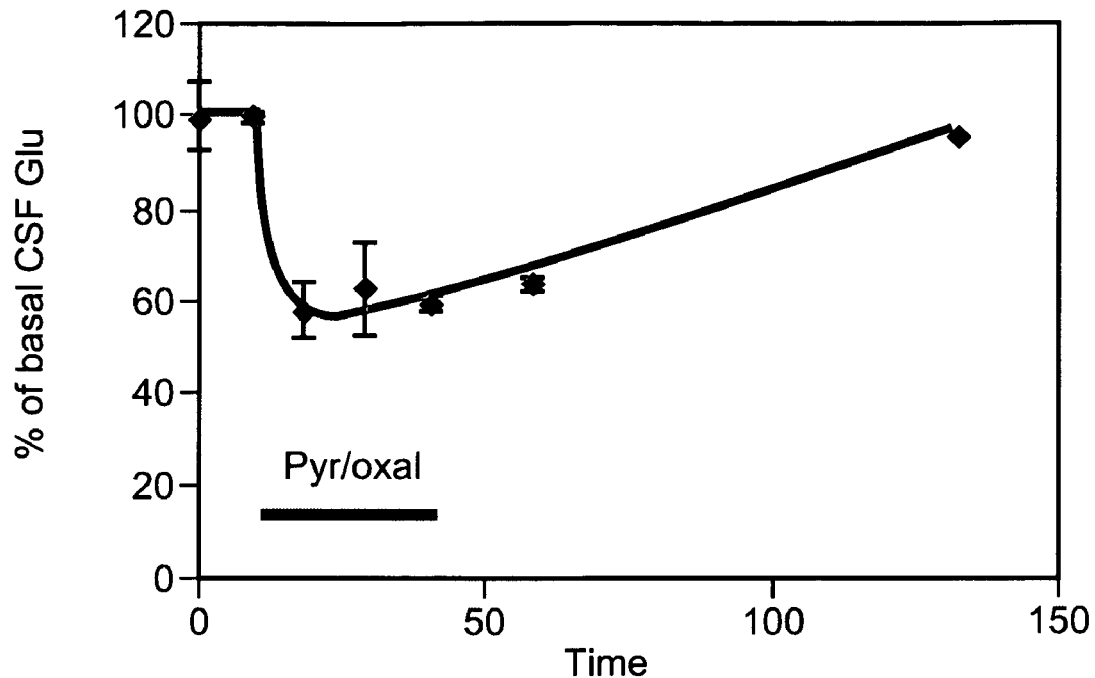
FIG. 25 shows changes in CSF glutamate levels following reduction of blood glutamate levels. The latter was achieved by an intravenous infusion of pyruvate and oxaloacetate at a rate of 50 μmoles/min for a duration of 30 min (bar). Under these conditions an average of 50±10% reduction of blood glutamate is achieved (see FIG. 9). One representative experiment out of 5 performed is shown.

Results—Yet another means of verifying whether reducing blood glutamate levels effects changes in brain glutamate concentration is via experiments monitoring the level of radio-labeled glutamate levels in the cerebrospinal fluid (CSF) following pyruvate/oxaloacetate administration, reducing plasma glutamate (FIG. 25). Intravenous administration of the GOT/GPT co-substrates dramatically reduced ISF/CSF glutamate, as determined by assaying CSF aliquots collected from cannulas implanted within the cisterna magna, prior to, during and following intravenous administration of pyruvate and oxaloacetate. The CSF glutamate levels were determined by methods as described in Kato et al. (1973) Anal. Biochem. 53:86-97 Under experimental conditions causing a 50% decrease in blood glutamate levels (FIG. 24), a parallel decrease is observed in glutamate CSF levels.

Thus additional direct evidence is provided attesting to an efflux of glutamate within the CSF to the blood, in response to reduced circulating glutamate levels, as a result of administration of the GOT/GPT co-substrates.

Figure 26:
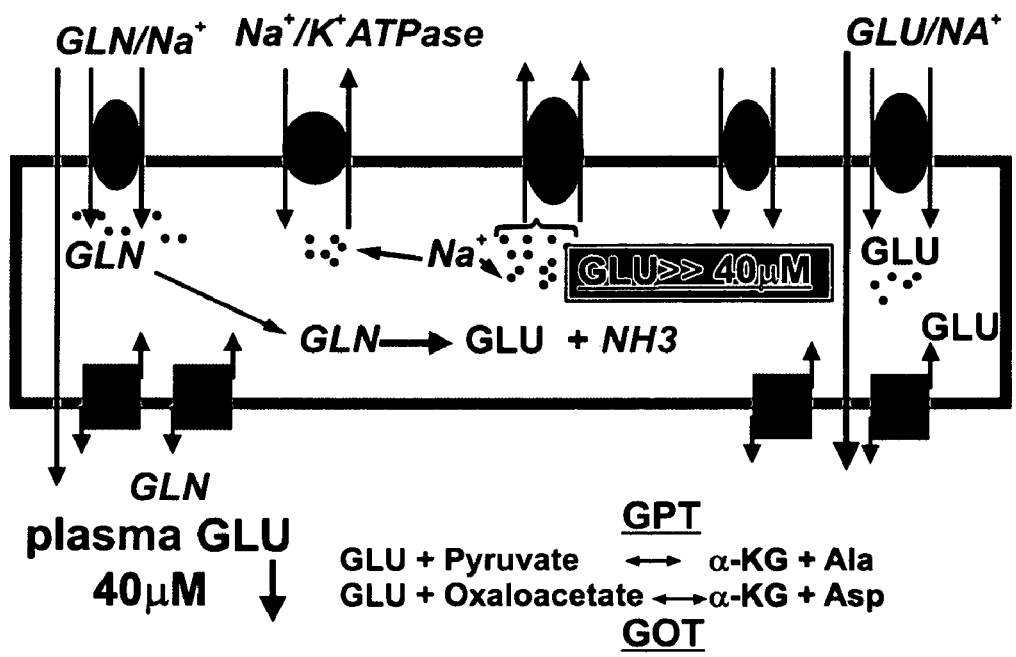
FIG. 26 is a proposed mechanism for the accelerated brain to blood glutamate efflux resulting from a decrease in blood glutamate levels. Pyruvate and oxaloacetate administered intravenously activate the blood-resident enzymes GPT and GOT respectively to decrease glutamate and produce α-ketoglutarate (α-KG), alanine and aspartate. As a result, the glutamate chemical gradient between endothelial cells and plasma is increased and the intraendothelial cell glutamate, increased as a result of antiluminal membrane glutamate transporter uptake and by glutaminase action, traffics into the plasma by facilitated diffusion. The decrease in intraendothelial glutamate concentration prevents Na+ ion (black circles) dependent "reverse pumping" of the glutamate transporters (that normally transport some glutamate into brain) increasing thereby the net glutamate efflux from the brain to the blood.

Though the exact mechanism by which pyruvate and oxaloacetate cause an enhanced brain to blood Glu efflux is unknown, one may be readily proposed, in lieu of the present experimental evidence (FIG. 26). In partial agreement with models proposed by Lee et. al. (2001) J. Neurosci. 21:RC171 and O'Kane et al. (1999) J. Biol. Chem. 274:31891-5, $Na^+$-dependent glutamate and glutamine transporters are present at the antiluminal membrane (brain facing) of brain capillary endothelial cells while facilitative systems for these amino acids are located on the luminal membrane (blood facing). Driven by a large $Na^+$ gradient, the transporters take up and concentrate glutamate and glutamine from the brain ISF within endothelial cells. A phosphate-dependent glutaminase present within the endothelial cells hydrolyzes glutamine into glutamate and ammonia, thereby creating a greater intracellular glutamate concentration than that present in plasma. The facilitative glutamate carriers at the luminal membrane then facilitate glutamate trafficking from endothelial cells to plasma, down an electrochemical gradient.

There is, however, an additional process whereby glutamate transporters saturated with intracellular glutamate, are activated by intracellular Na+ ions and allow reverse mobilization of glutamate and $Na^+$ ions to the ISF. This "reverse pumping" process functioning in concert with the action of Na+/K+ ATPases prevent the accumulation of intracellular Na+ ions. The reduction of blood glutamate levels increases the glutamate gradient, accelerating glutamate endothelial cell efflux to plasma. As the glutamate transporters cease being saturated with intraendothelial cell glutamate, the "reverse pumping" process is greatly diminished and the net glutamate influx from ISF to endothelial cells is increased.

Example 21

Conversion of Diethyloxaloacetate to Oxaloacetate And its Effects on Glutamate Levels The previous examples have illustrated the feasibility of utilizing oxaloacetate/pyruvate administration in a clinical setting, as a means of lowering in vivo organ glutamate concentration, by virtue of glutamate efflux from the desired organs to peripheral circulation, as a consequence of oxaloacetate/pyruvate-mediated circulatory glutamate reduction.

Oxaloacetic acid is a di-carboxylic ketoacid readily soluble in water. The acidity of oxaloacetic acid, however, necessitates full titration of its carboxyl moieties with sodium hydroxide in order to obtain solutions at neutral pH. Thus, at least two sodium ions are needed per molecule of oxaloacetic acid. Since oxaloacetate putatively exerts its therapeutic effect at relatively high concentrations, the accompanying sodium ions represent a possibly unacceptable electrolyte load for safe clinical application.

The use of an oxaloacetate prodrug, which following in vivo administration, is converted to oxaloacetate, may obviate this problem. Thus the commercially available oxaloacetate diethylester (FIG. 27B) was considered in this context. Conversion of oxaloacetate diethylester into oxaloacetate following incubation with tissue homogenates derived from rat liver, colon, ileum, jejunum and duodenum was investigated. Conversion of oxaloacetate diethylester to oxaloacetate is presumably via the action of specific esterases present in the various tissue homogenates, and hence reflects the in vivo fate of oxaloacetate diethylester following injection.

Results—Conversion of diethyloxaloacetate into oxaloacetate was determined in rat blood samples. FIG. 29B shows that while basal levels of blood oxaloacetate decreased by 40% along a duration of 24 hours, a significant increase of 240% was evident following incubation in the presence of 10 mM diethyloxaloacetate.

Figure 28:
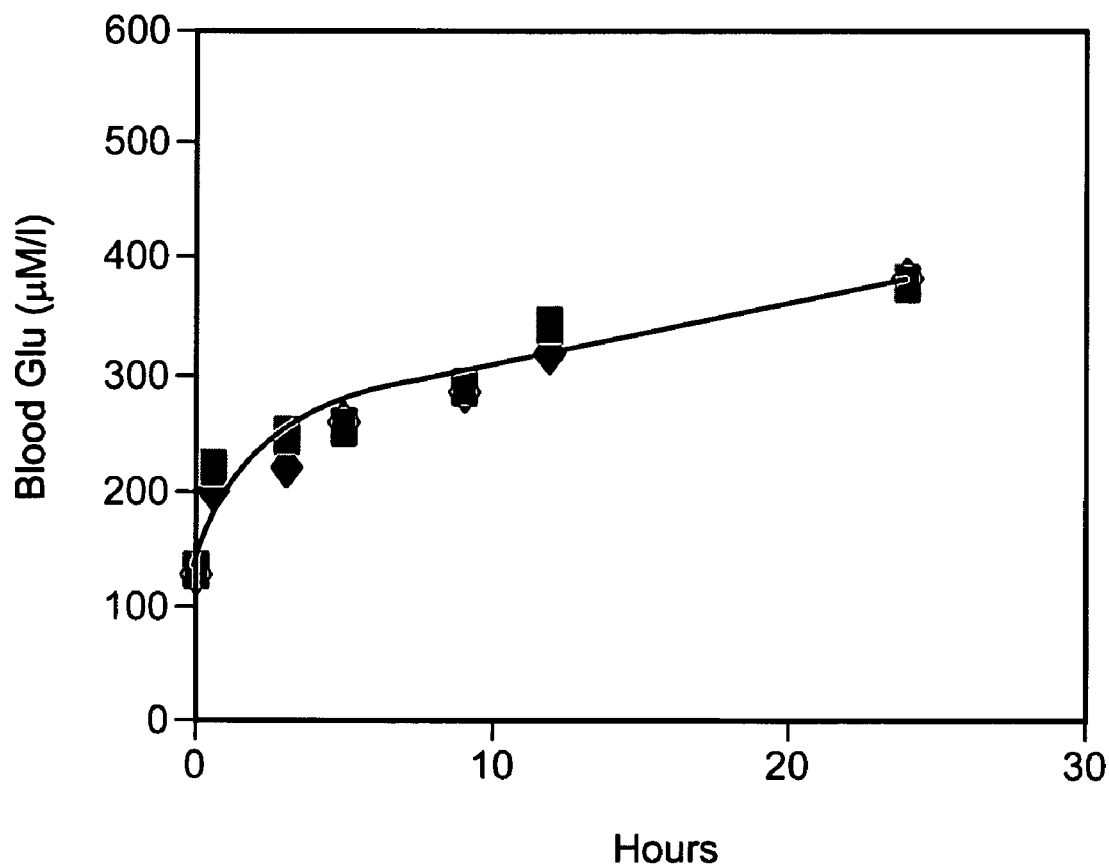
FIG. 28 shows the evolution of the blood glutamate concentration upon incubation in vitro for 24 hours at 37° C. in the presence of 10 mM diethyloxaloacetate.
Figure 30:
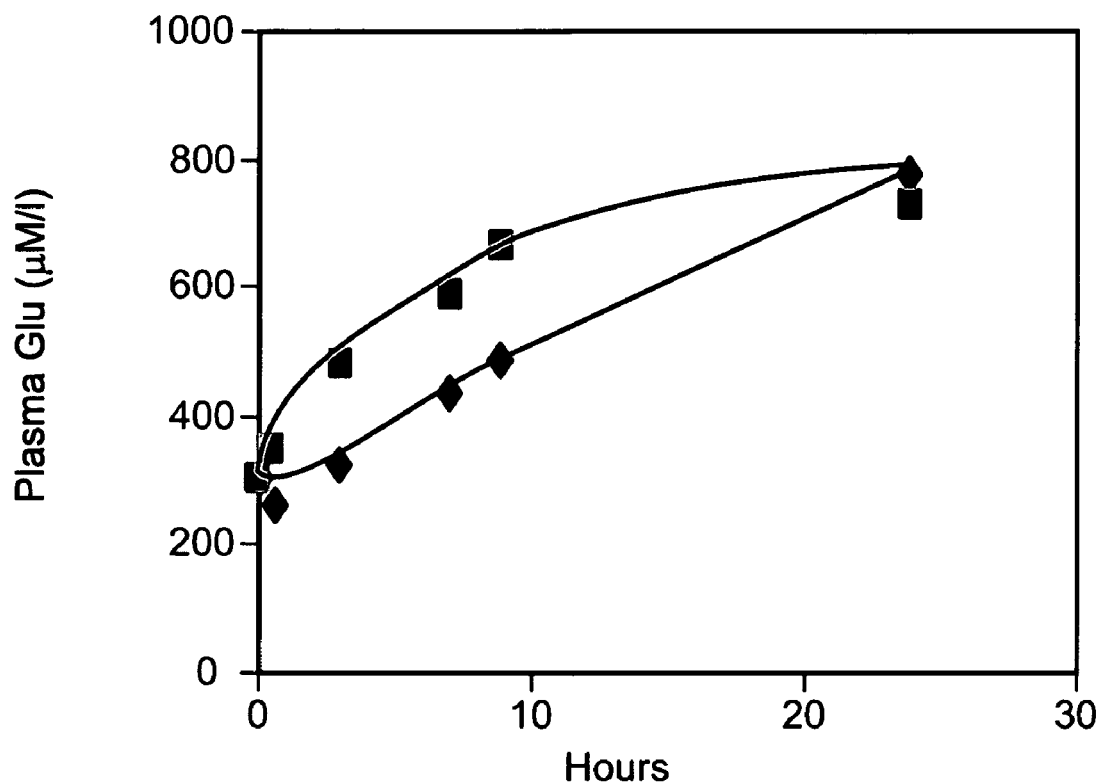
FIG. 30 depicts the increase in concentration of glutamate following in vitro incubation of rat blood plasma for 24 hours in the absence (diamonds) or presence (squares) of 10 mM diethyloxaloacetate.
Figure 31:
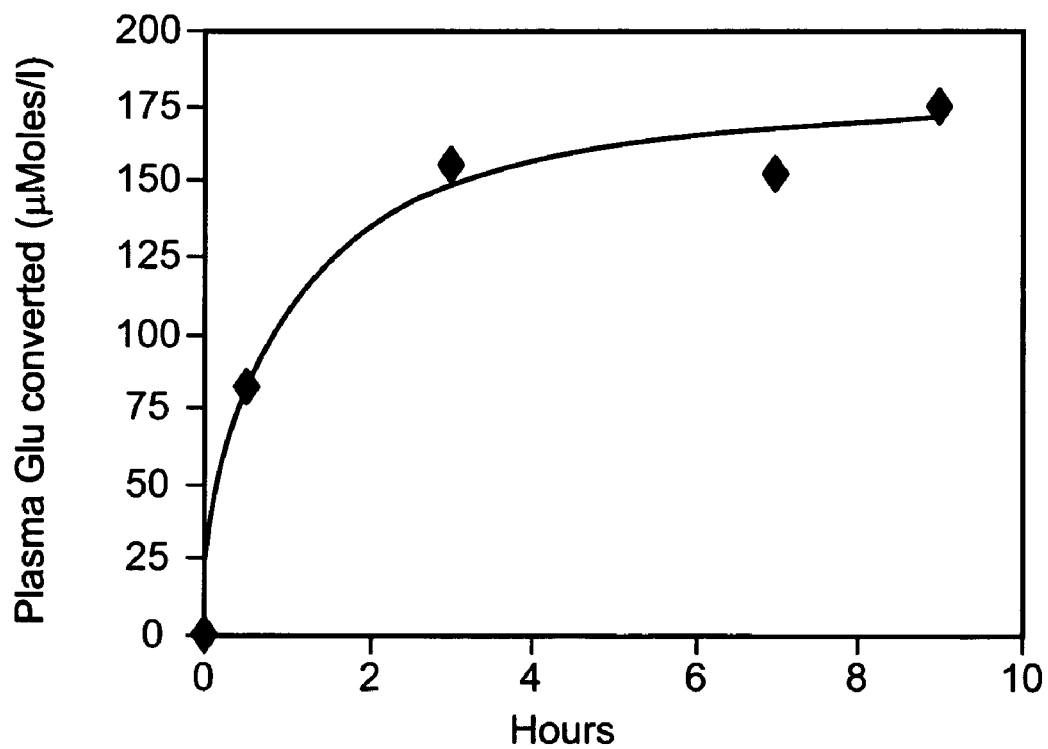
FIG. 31 depicts the levels of glutamate converted into 2-ketoglutarate following in vitro incubation of rat blood plasma in the presence of 10 mM diethyloxaloacetate for the indicated time intervals.

Thereafter, the effect of diethyloxaloacetate on Glutamate levels was assessed. Glutamate levels were determined in rat blood samples upon incubation in the absence or presence of 10 mM diethyloxaloacetate. As shown in FIG. 28, although glutamate blood levels constantly increased, addition of diethyloxaloacetate did not affect glutamate blood levels. Interestingly, glutamate levels in rat blood plasma were significantly affected by the presence of diethyloxaloacetate. FIG. 30 shows a significant increase in plasma glutamate following 9 hours incubation with diethyloxaloacetate. FIG. 31 represents the amount of plasma glutamate converted probably into α-ketoglutarate following the activation of GOT as a function of time by the presence of 10 mM diethyloxaloacetate.

Figure 29A:
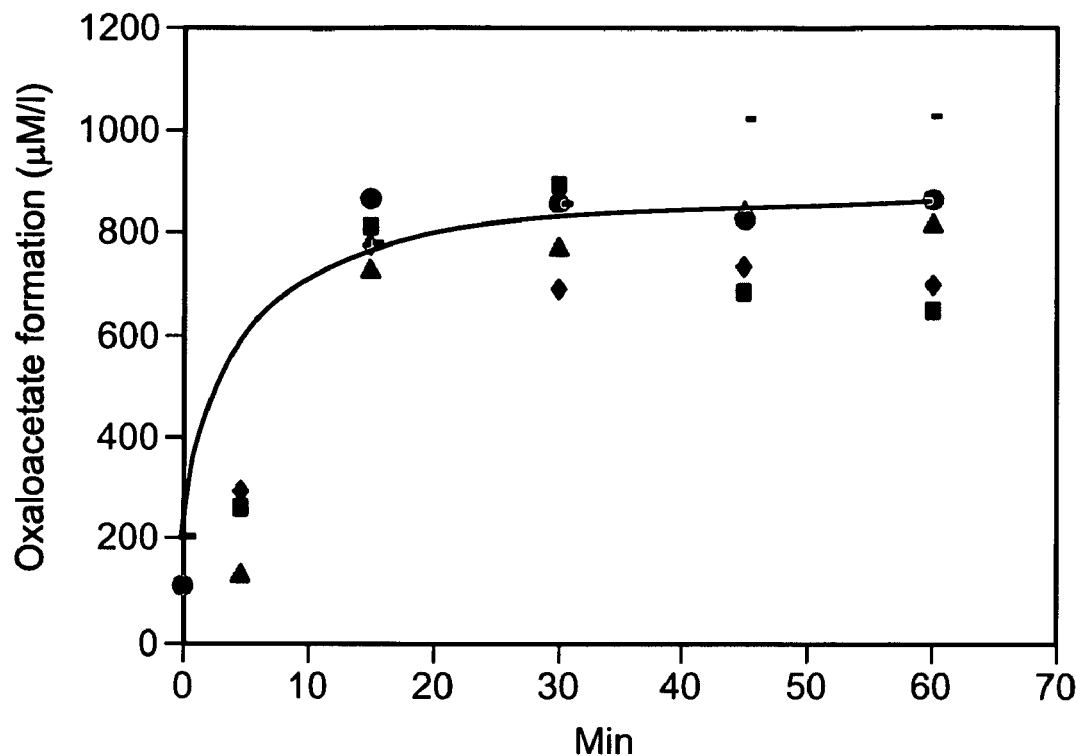
FIG. 29A depicts the increase in concentration of oxaloacetate following the incubation of 10 mM diethyloxaloacetate for one-hour at 37° C. in different rat tissue homogenates. Circles—duodenum; Squares—jejunum; Triangles—ileum; Diamonds—colon; Dashes—liver.
Figure 29B:
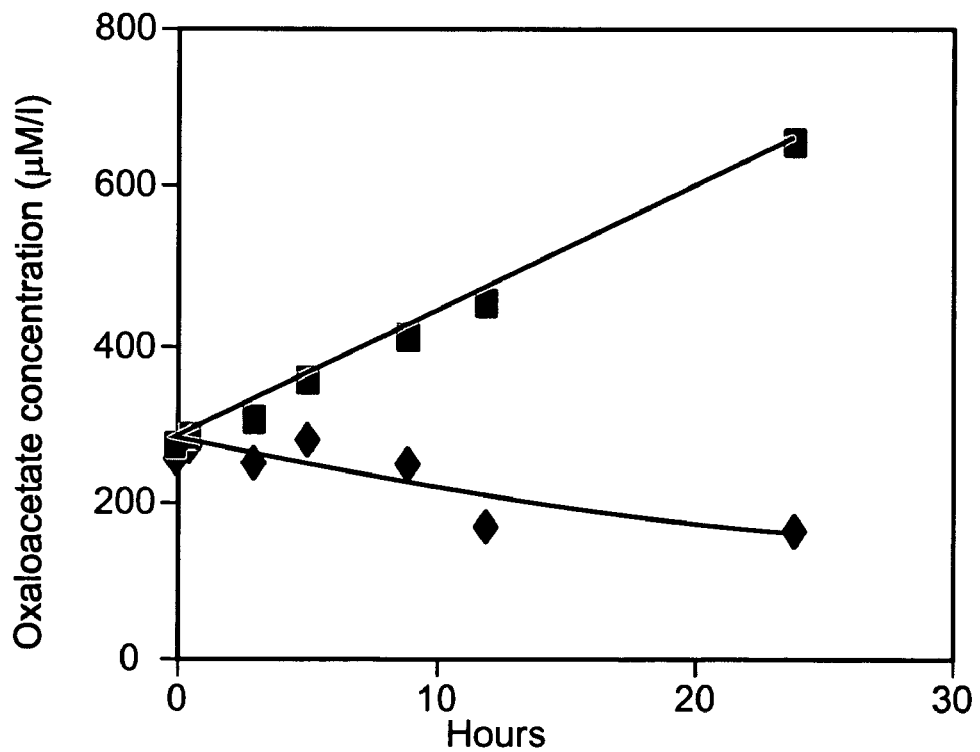
FIG. 29B depicts the increase in concentration of oxaloacetate following the in vitro incubation of 10 mM diethyloxaloacetate for 24 hours at 37° C. in rat blood (Squares). Control samples in the absence of diethyloxaloacetate are indicated by diamonds.

Incubation of liver and sections of rat gut mucosa with 10 mM diethyloxaloacetate revealed a 400% increase in basal oxaloacetate levels within 15 minutes, indicating that diethyloxaloacetate is a substrate for liver and gut esterases and is converted in vivo to oxaloacetate (FIG. 29A).

Thus diethyloxaloacetate subjected to plasma esterases is converted in oxaloacetate, which then functions as a co-substrate for plasma glutamate-oxaloacetate transaminase, decreasing plasma glutamate levels further indicative of diethyloxaloacetate (or other artificially modified derivatives of oxaloacetate that can be converted in vivo into oxaloacetate) as a viable, therapeutic oxaloacetate prodrug with enormous clinical application.

Example 22

Input of Pyruvate and Oxaloacetate Analogues to Glutamate Conversion in Rat Blood Plasma Numerous co-factors are available for the transamination reaction mediated by glutamate modifying enzymes (e.g., GOT, GPT).

A number of glutamate modifying enzymes were tested for their ability to enhance glutamate conversion in rat blood plasma. Table 1 below summarizes the results obtained with 1 mM of each co-substrate.

TABLE 1

| Compound | % of remaining Glutamate |
| --- | --- |
| α-Ketobutyrate | 97 |
| Succinic semialdehyde | 78 |
| Glyoxalate | 74 |
| α-Isocaproate | 83 |
| β-Hydroxypyruvate | 74 |

TABLE 1-continued

| Compound | % of remaining Glutamate |
| --- | --- |
| β-Phenylpyruvate | 76 |
| Pyruvate | 59 |
| Oxaloacetate | 34 |
| Pyruvate + Oxaloacetate | 24 |
| Pyruvate + α-Ketobutyrate | 52 |
| Oxaloacetate + α-Ketobutyrate | 20 |

Figure 33:
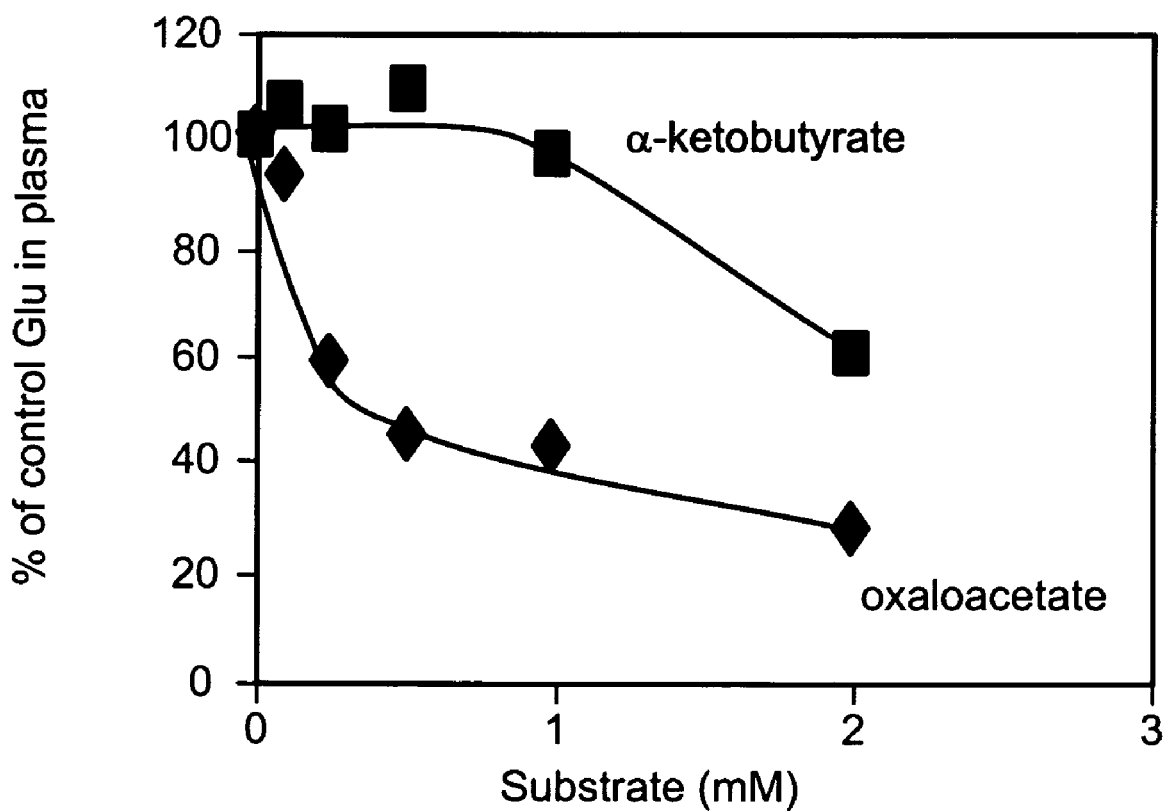
FIG. 33 is a graph depicting the in vitro blood glutamate levels following repeated administrations (every 15 minutes from t=0 up to t=45 min) of α-ketobutyrate (closed squares) or oxaloacetate (closed diamonds) each at 1 mM.

As is evident from Table 1, none of the co-factors tested mediated higher Glutamate degradation than pyruvate or oxaloacetate at the same concentration of 1 mM. These results were further substantiated in a dose response experiment. FIG. 33 shows that while 0.5 mM oxaloacetate mediated a significant decrease in plasma glutamate levels (i.e., 40%), identical concentration of α-Ketobutyrate had no effect on glutamate in rat plasma. However, higher concentration (i.e 2 mM) of α-Ketobutyrate could support glutamate degradation of 40% as compared to basal glutamate levels in rat plasma.

Figure 34:
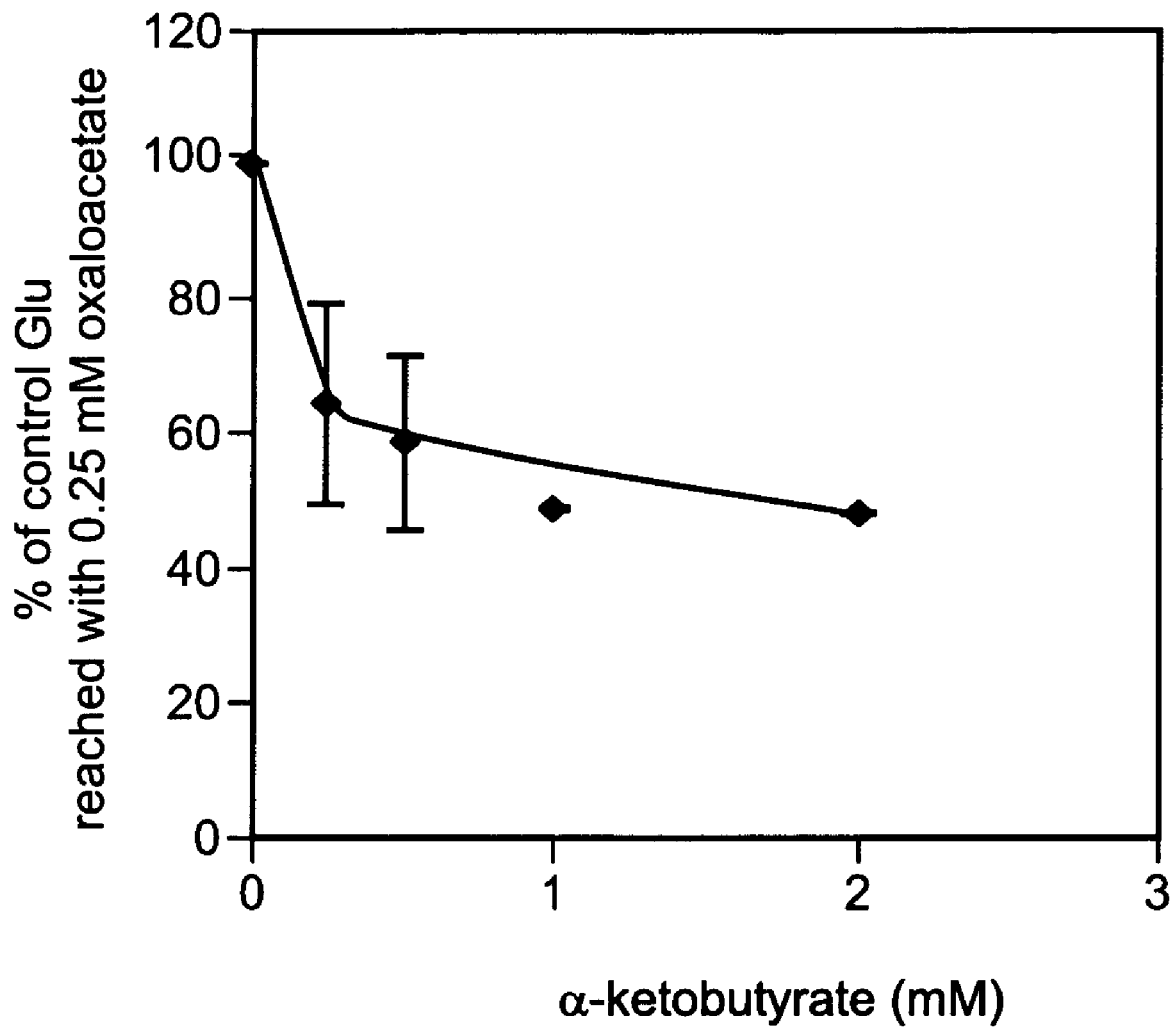
FIG. 34 is a graph depicting the in vitro blood glutamate levels in the presence of 0.25 mM oxaloacetate and the indicated concentrations of α-ketobutyrate. Note that the effect of α-ketobutyrate was normalized to the level of blood glutamate that was achieved in the presence of 0.25 mM oxaloacetate alone.

An additional dose response experiment was effected to determine an additive contribution of α-Ketobutyrate to oxaloacetate mediated glutamate conversion. As shown in FIG. 34, α-Ketobutyrate mediated an enhanced conversion of glutamate in the presence of 0.25 mM oxaloacetate.

These results suggest that a smaller concentration of oxaloacetate may be used in conjunction with as much as 0.5 mM α-Ketobutyrate to optimally reduce Glutamate levels, while avoiding the toxic effects of the first.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent, patent application was specifically and individually indicated to be incorporated herein by reference. In addition, citation or identification of any reference in this application shall not be construed as an admission that such reference is available as prior art to the present invention.

What is claimed is:

1. A method of reducing extracellular brain glutamate levels in a subject in need thereof, the method comprising intravenously administering to the subject a therapeutically effective amount of a glutamate modifying enzyme, thereby enhancing brain to blood glutamate efflux, thereby reducing extracellular brain glutamate levels.

2. The method of claim 1, wherein said glutamate modifying enzyme is a naturally occurring enzyme.

3. The method of claim 1, wherein said at least one glutamate modifying enzyme is selected from the group consisting of a transaminase, a dehydrogenase, a decarboxylase, a ligase, an aminomutase , a racemase and a transferase.

4. The method of claim 3, wherein said transaminase is selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, (s)-3-amino-2-methylpropionate transaminase, 4-hydroxyglutamate transaminase, diiodotyrosine transaminase, thyroid-hormone transaminase, tryptophan transaminase, diamine transaminase, cysteine transaminase, L-Lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, and udp-2-acetamido-4-amino-2,4,6-trideoxyglucose transaminase.

5. The method of claim 1, further comprising administering to the subject at least one co-factor of a glutamate modifying enzyme.

6. The method of claim 5, wherein said co-factor is selected from the group consisting of oxaloacetate, pyruvate, $NAD^+$, $NADP^+$, 2-oxohexanedioic acid, 2-oxo-3-sulfopropionate, 2-oxo-3-sulfinopropionic acid, 2-oxo-3-phenylpropionic acid, 3-indole-2-oxopropionic acid, 3-(4-hydroxyphenyl)-2-oxopropionic acid, 4-methylsulfonyl-2-oxobutyric acid, 3-hydroxy-2-oxopropionic acid, 5-oxopentanoate, 6-oxohexanoate, glyoxalate, 4-oxobutanoate, α-ketoisocaproate, α-ketoisovalerate, α-keto-β-methylvalerate, succinic semialdehyde-(-4-oxobutyrate), pyridoxal phosphate, pyridoxal phosphate precursors and 3-oxoisobutanoate.

7. The method of claim 1, wherein said glutamate modifying enzyme is an artificially modified glutamate modifying enzyme incapable of converting a glutamate metabolite into glutamate.

8. The method of claim 7, wherein said artificially modified glutamate modifying enzyme is an artificially modified human GOT.

9. The method of claim 1, further comprising administering to the subject a co-factor of said glutamate modifying enzyme, said glutamate modifying enzyme being artificially modified glutamate modifying enzyme incapable of converting modified glutamate into glutamate.

10. The method of claim 9, wherein said co-factor is selected from the group consisting of lipoic acid, lipoic acid precursor, pyridoxal phosphate, pyridoxal phosphate precursor, thiamine pyrophosphate and thiamine pyrophosphate precursor.

11. The method of claim 1, wherein said administering is effected at a concentration of said enzyme not exceeding 1 g/Kg body weight/hour.

12. The method of claim 1, wherein said glutamate modifying enzyme is a glutamate oxaloacetate transaminase.

13. The method of claim 12, further comprising administering oxaloacetate.

14. A method of reducing extracellular brain glutamate levels, the method comprising intravenously administering to a subject in need thereof a therapeutically effective amount of a glutamate modifying enzyme and a co-factor thereof, thereby enhancing brain to blood glutamate efflux, thereby reducing extracellular brain glutamate levels.

15. The method of claim 14, wherein said glutamate modifying enzyme is glutamate oxaloacetate transaminase and said co-factor is oxaloacetate.

16. The method of claim 14, wherein said glutamate modifying enzyme is a naturally occurring enzyme.

17. The method of claim 14, wherein said glutamate modifying enzyme is an artificially modified glutamate modifying enzyme incapable of converting a glutamate metabolite into glutamate.

* * * * *